United States Patent [19]

Fujita et al.

[11] Patent Number: 6,149,838

[45] Date of Patent: Nov. 21, 2000

[54] CONJUGATED NITRILE DERIVATIVE, LIQUID CRYSTAL COMPOSITION, AND LIQUID CRYSTAL DISPLAY ELEMENTS

[75] Inventors: Atsuko Fujita; Norio Tamura; Shuichi Matsui; Kazutoshi Miyazawa; Hiroyuki Takeuchi; Yasuhiro Kubo; Fusayuki Takeshita; Etsuo Nakagawa, all of Chiba, Japan

[73] Assignee: Chisso Corporation, Osaka, Japan

[21] Appl. No.: 09/319,025

[22] PCT Filed: Nov. 27, 1997

[86] PCT No.: PCT/JP97/04328

§ 371 Date: May 28, 1999

§ 102(e) Date: May 28, 1999

[87] PCT Pub. No.: WO98/23583

PCT Pub. Date: Jun. 4, 1998

[30] Foreign Application Priority Data

Nov. 28, 1996 [JP] Japan ..................................... 8-332771
Dec. 10, 1996 [JP] Japan ..................................... 8-346636

[51] Int. Cl.$^7$ .......................... C09K 19/34; C09K 19/30; C09K 19/12
[52] U.S. Cl. ............................. 252/299.61; 252/299.63; 252/299.66
[58] Field of Search ...................... 252/299.61, 299.63, 252/299.66

[56] References Cited

U.S. PATENT DOCUMENTS

| | | | |
|---|---|---|---|
| 5,154,851 | 10/1992 | Goto et al. | 252/299.63 |
| 5,370,819 | 12/1994 | Fujita et al. | 252/299.01 |
| 5,635,108 | 6/1997 | Fujita et al. | 252/299.63 |
| 5,658,489 | 8/1997 | Higashi et al. | 252/299.01 |
| 5,725,797 | 3/1998 | Asakura et al. | 252/299.61 |
| 6,015,508 | 1/2000 | Ohnishi et al. | 252/299.63 |

FOREIGN PATENT DOCUMENTS

| | | |
|---|---|---|
| 57-70851 | 5/1982 | Japan . |
| 59-139353 | 8/1984 | Japan . |
| 60-19756 | 1/1985 | Japan . |
| 60-169455 | 9/1985 | Japan . |
| 6-239825 | 8/1994 | Japan . |
| 7-330636 | 12/1995 | Japan . |
| 8-283226 | 10/1996 | Japan . |

OTHER PUBLICATIONS

Coates et al., "Effect of Light on the Liquid Crystal Transition Temperatures of 4–(4–n–Pentylphenyl)vinyl Cyanide", J.C.S. Chem. Comm., 1975, pp. 514–515.

*Primary Examiner*—C. H. Kelly
*Attorney, Agent, or Firm*—Wenderoth, Lind & Ponack, L.L.P.

[57] ABSTRACT

Liquid crystalline compounds having a wide temperature range of liquid crystal phase, a high dielectric anisotropy, and a high optical anisotropy; and liquid crystal compositions and display devices containing the composition. The liquid crystalline compounds are conjugated nitrile derivatives expressed by the formula (1)

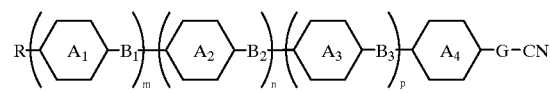

(1)

wherein R represents an alkyl group or a fluoroalkyl group each having 1 to 10 carbon atoms, halogen atom, or cyano group provided that in the alkyl or fluoroalkyl group, one or not-adjacent two or more methylene or fluoromethylene groups may be replaced by oxygen atom or 1,2-ethenylene group; $A_1$, $A_2$, $A_3$ and $A_4$ represent 1,4-cyclohexylene group, 1,4-phenylene in which one or two hydrogen atoms on the ring may be replaced by fluorine atom, 1,3-dioxane-2,5-diyl, or pyrimidine-2,5-diyl; $B_1$, $B_2$, and $B_3$ independently represent a covalent bond, 1,2-ethylene group, 1,2-ethenylene group, 1,2-ethynylene group, carbonyloxy group, methylenoxy group, or 1,4-butylene group; m, n, and p are 0 or 1; and G represents a group expressed by the formula

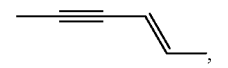

,

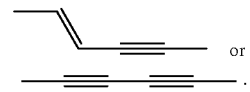 or

.

45 Claims, No Drawings

CONJUGATED NITRILE DERIVATIVE, LIQUID CRYSTAL COMPOSITION, AND LIQUID CRYSTAL DISPLAY ELEMENTS

This application is a 371 application of International Application No. PCT/JP97/04328 filed Nov. 27, 1997.

TECHNICAL FIELD

The present invention relates to liquid crystalline compounds and liquid crystal compositions. More specifically, the invention relates to conjugated nitrile derivatives of liquid crystalline compounds preferable as component of liquid crystal compositions; liquid crystal compositions comprising the nitrile derivative; and liquid crystal display devices fabricated by using the liquid crystal composition.

BACKGROUND ART

Liquid crystal display devices utilize optical (refractive) anisotropy and dielectric anisotropy of liquid crystalline compounds. Viewing from the aspect of display mode, display devices of twisted nematic (TN) type, super twisted nematic (STN) type, dynamic scattering (DS) type, guest, host (GH) type, or DAP type organized according to their electrooptical effect are known. From the aspect of driving mode, display devices of static driving mode, time shearing addressing mode, active matrix driving mode, or two-frequency addressing scheme are known. Liquid crystal substances used for the display devices are required to exhibit a liquid crystal phase in a wide temperature range and to be stable against heat, light, moisture, air, electric field, and electromagnetic radiation.

However, since it is impossible to satisfy all of such requirements by a single compound at present, it is a current situation that several, or in some cases more than twenty liquid crystalline compounds are mixed and used as liquid crystal compositions. Accordingly, the liquid crystalline compounds have come to be required to exhibit excellent miscibility each other. Recently in particular, since display devices are used in many instances in sever environments such as at cryogenic temperatures, improvement of the compounds in the miscibility at low temperatures has come to be required.

With the increase of demand for display devices of high quality, requests for liquid crystal composition having an improved response speed to the change in electric field, and steepness have been increased. In order to fulfil the requirements, it is required to use liquid crystal materials having a low viscosity and a large dielectric anisotropy value as component of liquid crystal compositions.

In order to increase the response speed of liquid crystal compositions, it is effective to make the thickness (d) of liquid crystal cells small (thin) in addition to satisfying the requirements described above. In this case, however, it is necessary to increase optical anisotropy value ($\Delta n$) (to use liquid crystalline compounds having a large $\Delta n$ as component) for the reason described below. That is, excellent display contrast and wide visual angle are found as other characteristics required of display devices. In order to achieve this end, it is necessary to maintain the product of $\Delta n$ and d ($\Delta n \cdot d$) at a certain value, and thus, when d is made small according to the measures described above, it is necessary to increase $\Delta n$.

For originating liquid crystalline compounds having a large $\Delta n$, it is sufficient, for instance, to introduce ethynylene group into a liquid crystal molecule, and it is known by means of the compounds expressed by the formula (13) (Japanese Patent Publication No. Hei 3-29051) and compounds expressed by one of the formulas (14) to (16) (DE 4027458 and WO 90-13610) that the compounds can be changed into ones having a large value even in dielectric anisotropy ($\Delta \epsilon$) by altering the ethynylene group into the one having an electron attractive group, for example, CN, Cl, $CHF_2$, or $CF_3$ as substituent.

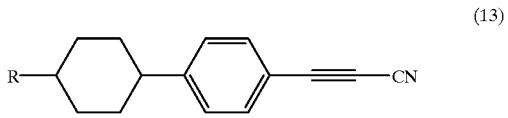

(13)

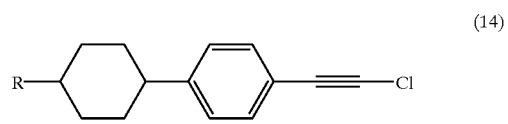

(14)

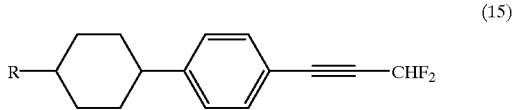

(15)

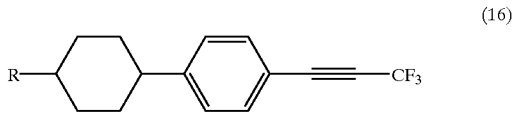

(16)

wherein R represents an alkyl group.

However, as to the compounds expressed by the formula (13), their electric properties are not disclosed at all in the Japanese Patent Publication No. Hei 3-29051. Compounds expressed by one of the formulas (14) to (16) are narrow in the temperature range of liquid crystal phase, and they can not be said to exhibit a sufficiently large value of either $\Delta n$ and $\Delta \epsilon$ besides.

An object of the present invention is to solve the defects in the conventional technology. Another object of the present invention is to provide conjugated nitrile derivatives, novel liquid crystalline compounds having a sufficiently large $\Delta n$ and a large $\Delta \epsilon$, being excellent in miscibility with other liquid crystalline compounds, having a low viscosity, and being chemically and physically stable; to provide liquid crystal compositions comprising the nitrile derivative; and to provide liquid crystal display devices fabricated by using the liquid crystal composition.

DISCLOSURE OF THE INVENTION

As a result of diligent investigations by the present inventors to achieve the objects described above, compounds of a novel structure having improved characteristics compared with known liquid crystalline compounds have been found, leading to the accomplishment of the present invention.

Summary of the present invention is as follows:

(1) A conjugated nitrile derivative expressed by the general formula (1)

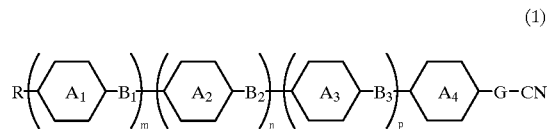

(1)

wherein rings $A_1$, $A_2$, $A_3$, and $A_4$ independently represent 1,4-cyclohexylene, 1,4-phenylene in which one or two hydrogen atoms on the ring may be replaced by fluorine atom, 1,3-dioxane-2,5-diyl, or pyrimidine-2,5-diyl; $B_1$, $B_2$, and $B_3$ independently pepresent a covalent bond, 1,2-ethylene, 1,2-ethenylene, 1,2-ethynylene, oxymethylene, methylenoxy, carbonyloxy, or 1,4-butylene group; G represents the formula (2), (3), or (4)

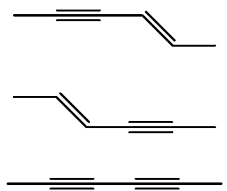

(2)

(3)

(4)

R represents an alkyl group having 1 to 10 carbon atoms, a fluoroalkyl group having 1 to 10 carbon atoms, a halogen atom, or cyano group provided that in the alkyl group or fluoroalkyl group, one or not-adjacent two or more methylene groups or fluoromethylene groups may be replaced by oxygen atom or 1,2-ethenylene group; m, n, and p are independently 0 or 1; and each element which constitutes the compound may be selected from its isotopes.

(2) The conjugated nitrile derivative recited in paragraph (1) above wherein m=n=p=0.

(3) The conjugated nitrile derivative recited in paragraph (1) above wherein m=n=0, and p=1.

(4) The conjugated nitrile derivative recited in paragraph (1) above wherein m=0, and n=p=1.

(5) The conjugated nitrile derivative recited in paragraph (1) above wherein m=n=p=1.

(6) The conjugated nitrile derivative recited in paragraph (3) above wherein G is the group expressed by the formula (2).

(7) The conjugated nitrile derivative recited in paragraph (6) above wherein $A_4$ is 1,4-cyclohexylene.

(8) The conjugated nitrile derivative recited in paragraph (6) above wherein $A_4$ is 1,4-phenylene ring in which one or two hydrogen atoms on the ring may be replaced by fluorine atom.

(9) The conjugated nitrile derivative recited in paragraph (7) above wherein $A_3$ is 1,4-cyclohexylene, and $B_3$ is a covalent bond.

(10) The conjugated nitrile derivative recited in paragraph (3) above wherein G is the group expressed by the formula (3).

(11) The conjugated nitrile derivative recited in paragraph (10) above wherein $A_4$ is 1,4-cyclohexylene.

(12) The conjugated nitrile derivative recited in paragraph (10) above wherein $A_4$ is 1,4-phenylene ring in which one or two hydrogen atoms on the ring may be replaced by fluorine atom.

(13) The conjugated nitrile derivative recited in paragraph (11) above wherein $A_3$ is 1,4-cyclohexylene, and $B_3$ is a covalent bond.

(14) The conjugated nitrile derivative recited in paragraph (12) above wherein $A_3$ is 1,4-cyclohexylene, and $B_3$ is a covalent bond.

(15) The conjugated nitrile derivative recited in paragraph (3) above wherein G is the group expressed by the formula (4).

(16) The conjugated nitrile derivative recited in paragraph (15) above wherein $A_4$ is 1,4-cyclohexylene.

(17) The conjugated nitrile derivative recited in paragraph (15) above wherein $A_4$ is 1,4-phenylene ring in which one or two hydrogen atoms on the ring may be replaced by fluorine atom.

(18) The conjugated nitrile derivative recited in paragraph (16) above wherein $A_3$ is 1,4-cyclohexylene, and $B_3$ is a covalent bond.

(19) The conjugated nitrile derivative recited in paragraph (17) above wherein $A_3$ is 1,4-cyclohexylene, and $B_3$ is a covalent bond.

(20) The conjugated nitrile derivative recited in paragraph (4) above wherein G is the group expressed by the formula (2).

(21) The conjugated nitrile derivative recited in paragraph (20) above wherein $A_4$ is 1,4-cyclohexylene.

(22) The conjugated nitrile derivative recited in paragraph (20) above wherein $A_4$ is 1,4-phenylene ring in which one or two hydrogen atoms on the ring may be replaced by fluorine atom.

(23) The conjugated nitrile derivative recited in paragraph (4) above wherein G is the group expressed by the formula (3).

(24) The conjugated nitrile derivative recited in paragraph (23) above wherein $A_4$ is 1,4-cyclohexylene.

(25) The conjugated nitrile derivative recited in paragraph (23) above wherein $A_4$ is 1,4-phenylene ring in which one or two hydrogen atoms on the ring may be replaced by fluorine atom.

(26) The conjugated nitrile derivative recited in paragraph (4) above wherein G is the group expressed by the formula (4).

(27) The conjugated nitrile derivative recited in paragraph (26) above wherein $A_4$ is 1,4-cyclohexylene.

(28) The conjugated nitrile derivative recited in paragraph (26) above wherein $A_4$ is 1,4-phenylene ring in which one or two hydrogen atoms on the ring may be replaced by fluorine atom.

(29) The conjugated nitrile derivative recited in paragraph (5) wherein G is the group expressed by the formula (2).

(30) The conjugated nitrile derivative recited in paragraph (29) above wherein $A_4$ is 1,4-cyclohexylene.

(31) The conjugated nitrile derivative recited in paragraph (29) above wherein $A_4$ is 1,4-phenylene ring in which one or two hydrogen atoms on the ring may be replaced by fluorine atom.

(32) The conjugated nitrile derivative recited in paragraph (5) above wherein G is the group expressed by the formula (3).

(33) The conjugated nitrile derivative recited in paragraph (32) above wherein $A_4$ is 1,4-cyclohexylene.

(34) The conjugated nitrile derivative recited in paragraph (32) above wherein $A_4$ is 1,4-phenylene ring in which one or two hydrogen atoms on the ring may be replaced by fluorine atom.

(35) The conjugated nitrile derivative recited in paragraph (5) above wherein G is the group expressed by the formula (4).

(36) The conjugated nitrile derivative recited in paragraph (35) above wherein $A_4$ is 1,4-cyclohexylene.

(37) The conjugated nitrile derivative recited in paragraph (35) above wherein $A_4$ is 1,4-phenylene ring in which one or two hydrogen atoms on the ring may be replaced by fluorine atom.

(38) A liquid crystal composition comprising at least one conjugated nitrile derivative recited in any one of paragraphs (1) through (37) above.

(39) A liquid crystal composition, comprising, as a first component, at least one conjugated nitrile derivative recited in any one of paragraphs (1) through (37) above, and comprising, as a second component, at least one compound selected from the group consisting of the compounds expressed by any one of the general formulas (5), (6), and (7)

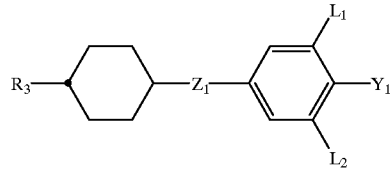
(5)

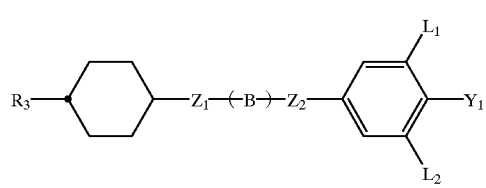
(6)

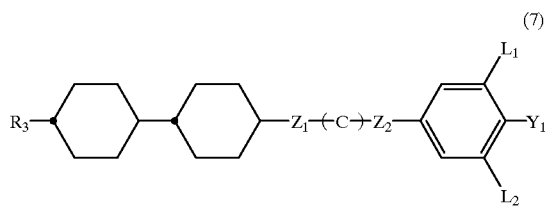
(7)

wherein $R_3$, $Y_1$, $L_1$, $L_2$, $Z_1$, and $Z_2$ may be the same or different from one another among the formulas; $R_3$ represents an alkyl group having 1 to 10 carbon atoms in which alkyl group, one or not-adjacent two or more methylene groups may be replaced by oxygen atom or —CH=CH—, and any hydrogen atom may be replaced by fluorine atom; $Y_1$ represents fluorine atom, chlorine atom, $OCF_3$, $OCF_2H$, $CF_3$, $CF_2H$, $CFH_2$, $OCF_2CF_2H$, or $OCF_2CFHCF_3$; $L_1$ and $L_2$ independently represent hydrogen atom or fluorine atom; $Z_1$ and $Z_2$ independently represent 1,2-ethylene group, 1,4-butylene group, —COO—, —$CF_2O$—, —$OCF_2$—, —CH=CH—, or a covalent bond; ring B represents trans-1,4-cyclohexylene or 1,3-dioxane-2,5-diyl, or 1,4-phenylene in which hydrogen atom on the ring may be replaced by fluorine atom; ring C represents trans-1,4-cyclohexylene, or 1,4-phenylene in which hydrogen atom on the ring may be replaced by fluorine atom; and each element which constitutes the compounds of each of the general formulas may be selected from its isotopes.

(40) A liquid crystal composition, comprising, as a first component, at least one conjugated nitrile derivative recited in any one of paragraphs (1) through (37) above, and comprising, as a second component, at least one compound selected from the group consisting of the compounds expressed by the general formula (8) or (9)

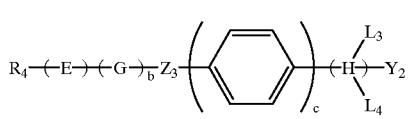
(8)

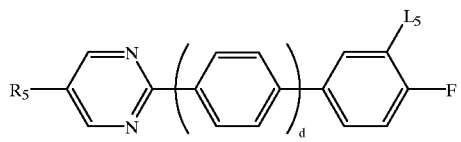
(9)

wherein $R_4$ and $R_5$ independently represent an alkyl group having 1 to 10 carbon atoms in which alkyl group, one or not-adjacent two or more methylene groups may be replaced by oxygen atom or —CH=CH—, and any hydrogen atom may be replaced by fluorine atom; $Y_2$ represents —CN group or —C≡C—CN; ring E represents trans-1,4-cyclohexylene, 1,4-phenylene, 1,3-dioxane-2,5-diyl, or pyrimidine-2,5-diyl; ring G represents trans-1,4-cyclohexylene, 1,4-phenylene in which hydrogen atom on the ring may be replaced by fluorine atom, or pyrimidine-2,5-diyl; ring H represents trans-1,4-cyclohexylene or 1,4-phenylene; $Z_3$ represents 1,2-ethylene group, —COO—, or a covalent bond; $L_3$, $L_4$, and $L_5$ independently represent hydrogen atom or fluorine atom; b, c, and d are independently 0 or 1; and each element which constitutes the compounds of each of the general formulas may be selected from its isotopes.

(41) A liquid crystal composition, comprising, as a first component, at least one conjugated nitrile derivative recited in any one of paragraphs (1) through (37) above, comprising, as a second component, at least one compound selected from the group consisting of the compounds expressed by any one of the general formulas (5), (6), and (7) described above, and comprising, as a third component, at least one compound selected from the group consisting of the compounds expressed by any one of the general formulas (10), (11), and (12)

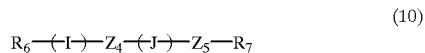
(10)

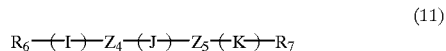
(11)

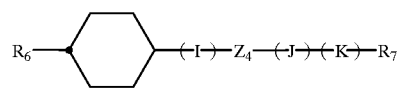
(12)

wherein $R_6$, $R_7$, I, J, and K may be the same or different from one another among the formulas; $R_6$ and $R_7$ independently represent an alkyl group having 1 to 10 carbon atoms in which alkyl group, one or not-adjacent two or more methylene groups may be replaced by oxygen atom or —CH=CH—, and any hydrogen atom may be replaced by fluorine atom; I, J, and K independently represent trans-1,4-cyclohexylene or pyrimidine-2,5-diyl, or 1,4-phenylene in which hydrogen atom on the ring may be replaced by fluorine atom; $Z_4$ and $Z_5$ independently represent —C≡C—, —COO—, —$CH_2CH_2$—, —CH=CH—, or a covalent bond; and each element which constitutes the compounds of each of the general formulas may be selected from its isotopes.

(42) A liquid crystal composition, comprising, as a first component, at least one conjugated nitrile derivative recited in any one of paragraphs (1) through (37) above, comprising, as a second component, at least one compound selected from the group consisting of the compounds expressed by the general formula (8) or (9) described above, and comprising, as a third component, at least one compound selected from the group consisting of the compounds expressed by any one of the general formulas (10), (11), and (12) described above.

(43) A liquid crystal composition, comprising, as a first component, at least one conjugated nitrile derivative recited in any one of paragraphs (1) through (37) above, comprising, as a part of a second component, at least one compound selected from the group consisting of the compounds expressed by any one of the general formulas (5), (6), and (7) described above, comprising, as another part of the second component, at least one compound selected from the group consisting of the compounds expressed by the general formula (8) or (9) described above, and comprising, as a third component, at least one compound selected from the group consisting of the compounds expressed by any one of the general formulas (10), (11), and (12) described above.

(44) A liquid crystal composition recited in any one of paragraphs (38) to (43) above wherein the liquid crystal composition further comprises an optically active compound.

(45) A liquid crystal display device fabricated by using the liquid crystal composition recited in any one of paragraphs (38) to (44) above.

As described above, the conjugated nitrile derivatives, the liquid crystalline compounds of the present invention are expressed by the general formula (1). Among them, a group of the compounds expressed by one of the formulas (1-a) to (1-n) can particularly be mentioned as preferable examples.

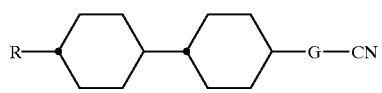
(1-a)

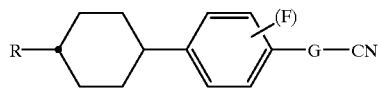
(1-b)

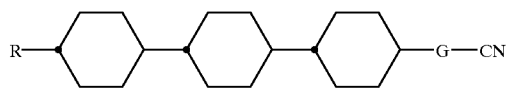
(1-c)

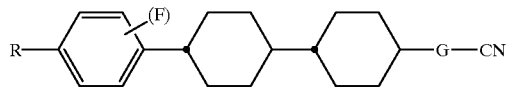
(1-d)

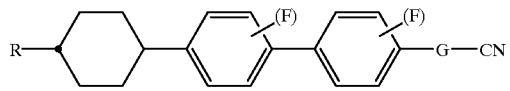
(1-e)

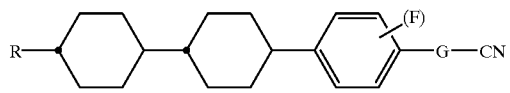
(1-f)

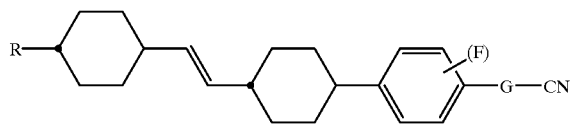
(1-g)

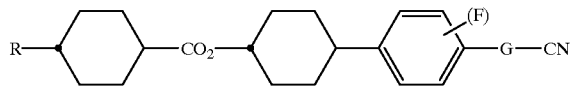
(1-h)

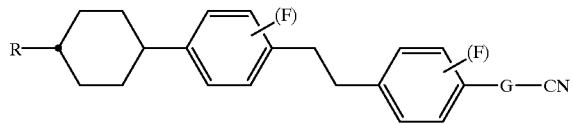
(1-i)

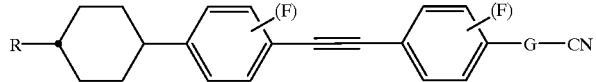
(1-j)

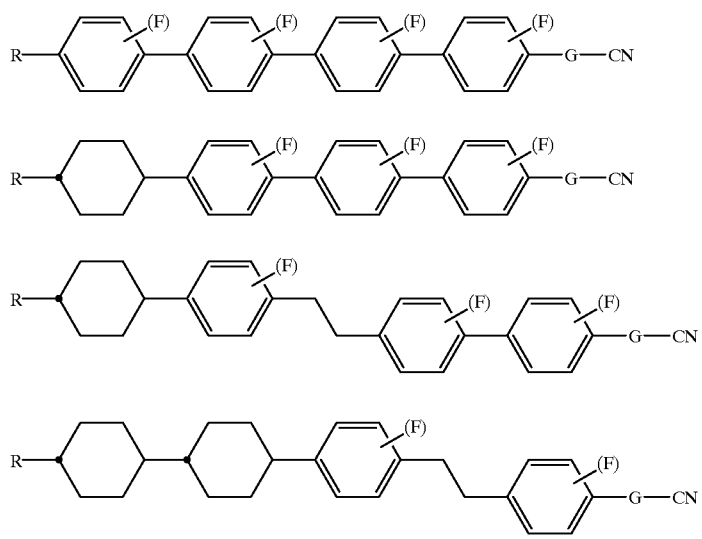

wherein R and G have the same meaning as described above.

Any of these compounds of the present invention exhibit a large Δn. Besides, they are low in viscosity, excellent in miscibility with other liquid crystalline compounds, and chemically and physically stable. Since particularly the compounds expressed by one of the formulas (1-k) to (1-n) further have a high clearing point, they can be used as component when liquid crystal compositions having a high upper limit temperature of liquid crystal are produced.

Since the compounds expressed by one of the formulas (1-e) to (1-n), particularly the compounds expressed by the formula (1-e), (1-j), (1-k), (1-l), or (1-m) have an extremely large Δn, they are remarkably useful.

All liquid crystalline compounds of the present invention expressed by the general formula (1) do not necessarily exhibit a liquid crystal phase. However, since any of the compounds is excellent in miscibility with other liquid crystalline compounds, and does not considerably lower or narrow the temperature range of nematic phase of other liquid crystalline compounds when mixed with them, it is useful as component of liquid crystal compositions even if it does not exhibit a liquid crystal phase by itself.

Liquid crystal compositions of the present invention comprise, as a first component, at least one liquid crystalline compound expressed by the general formula (1).

It is necessary to develop excellent characteristics that the content of the compound is 0.1 to 99.9% by weight based on the amount of the liquid crystal composition.

While the liquid crystal compositions of the present invention may be composed only of the first component described above, compositions in which at least one compound selected from the group consisting of the compounds expressed by one of the general formulas (5), (6), and (7) described above (the compounds are hereinafter referred to as second component A) and/or at least one compound selected from the group consisting of the compounds expressed by the general formula (8) or (9) described above (the compounds are hereinafter referred to as second component B) are mixed as a second component in addition to the first component; or compositions in which at least one compound selected from the group consisting of the compounds expressed by one of the general formulas (10), (11), and (12) described above are additionally mixed as a third component to the first and second components are preferable. Further, an optically active compound, and known compounds for the purpose of adjusting threshold voltage, temperature range of liquid crystal phase, Δn, Δε, and viscosity can be mixed as other components to the compositions.

Among the second component A, compounds expressed by one of the formulas (5-1) to (5-9) can be mentioned as preferable examples of the compounds included in the general formula (5), compounds expressed by one of the formulas (6-1) to (6-69) can be mentioned as preferable examples of the compounds included in the general formula (6), and compounds expressed by one of the formulas (7-1) to (7-24) can be mentioned as preferable examples of the compounds included in the general formula (7), respectively.

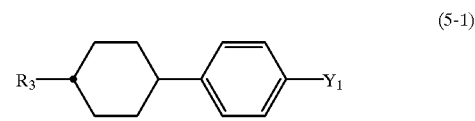

(5-1)

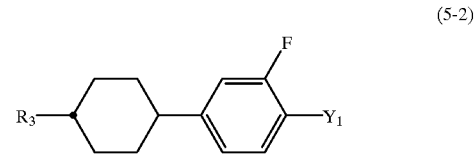

(5-2)

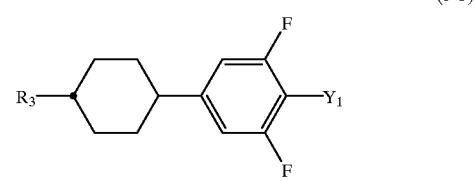

(5-3)

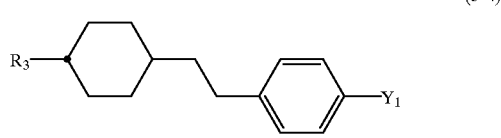

(5-4)

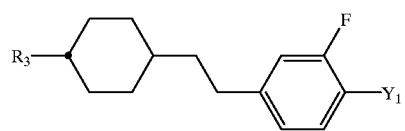 (5-5)
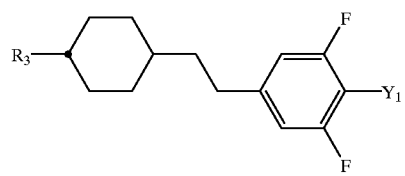 (5-6)
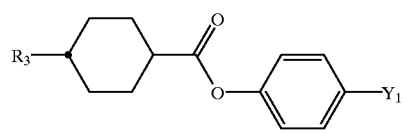 (5-7)
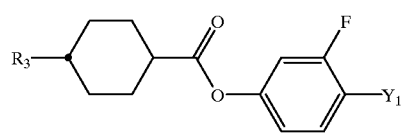 (5-8)
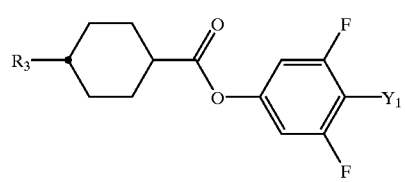 (5-9)
 (6-1)
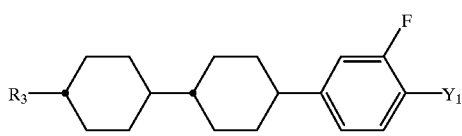 (6-2)
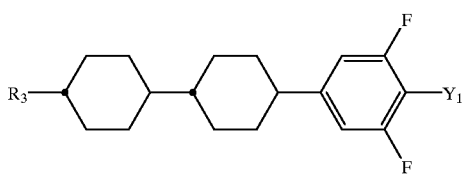 (6-3)
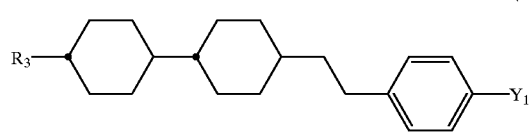 (6-4)
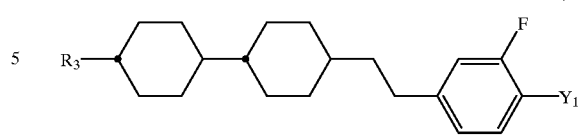 (6-5)
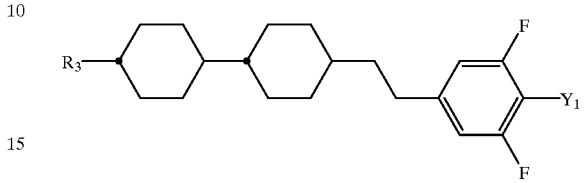 (6-6)
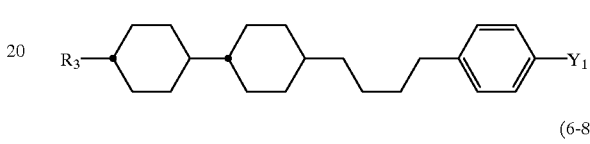 (6-7)
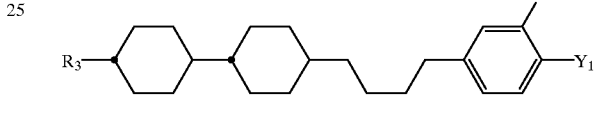 (6-8)
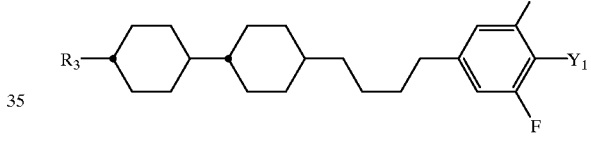 (6-9)
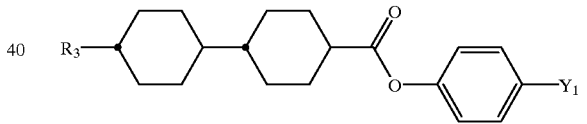 (6-10)
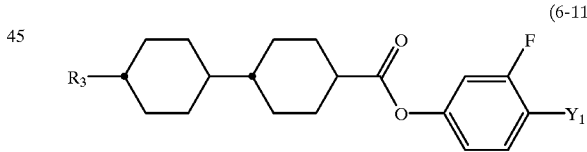 (6-11)
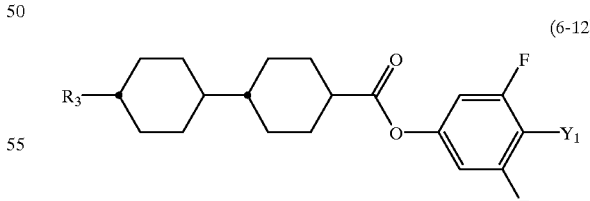 (6-12)
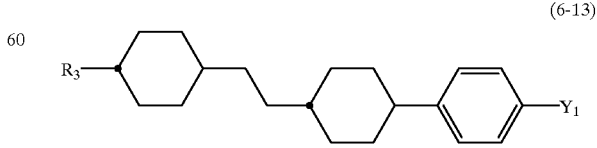 (6-13)

(6-14) 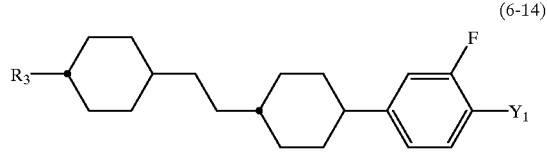
(6-15) 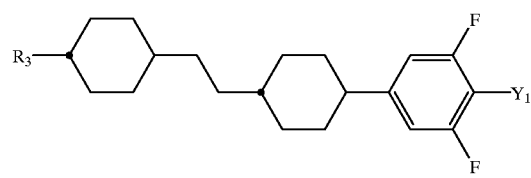
(6-16) 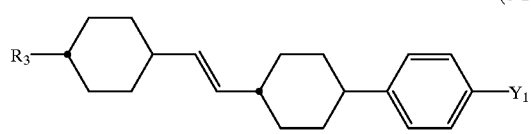
(6-17) 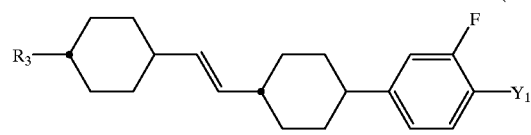
(6-18) 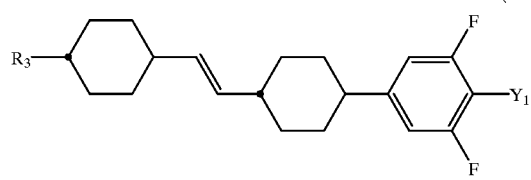
(6-19) 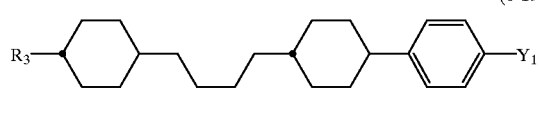
(6-20) 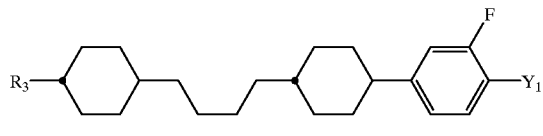
(6-21) 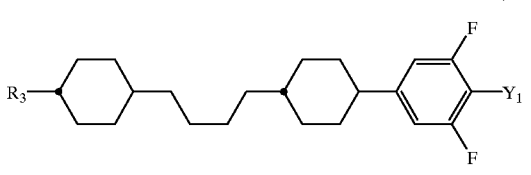
(6-22) 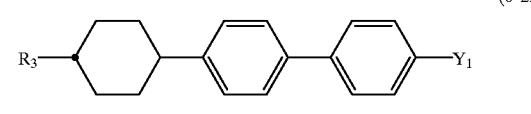
(6-23) 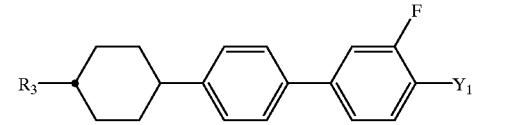
(6-24) 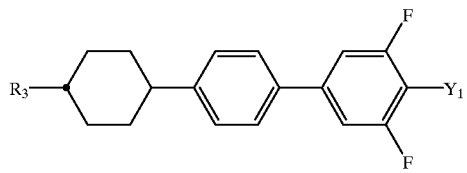
(6-25) 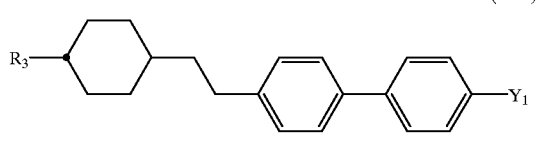
(6-26) 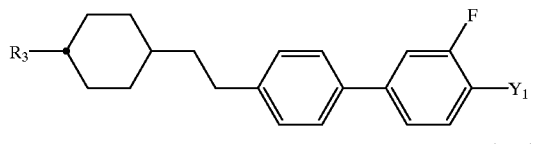
(6-27) 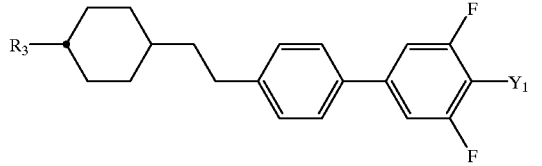
(6-28) 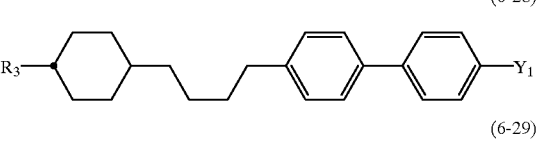
(6-29) 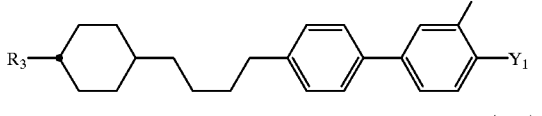
(6-30) 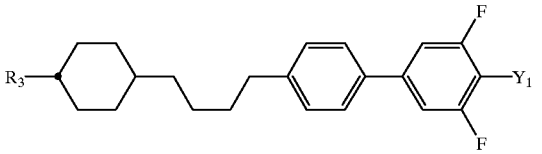
(6-31) 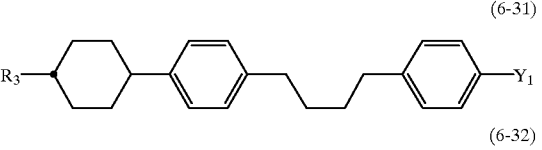
(6-32) 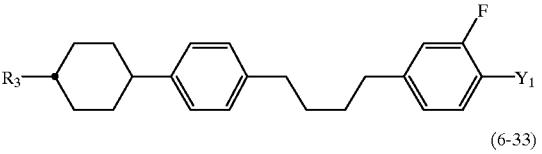
(6-33) 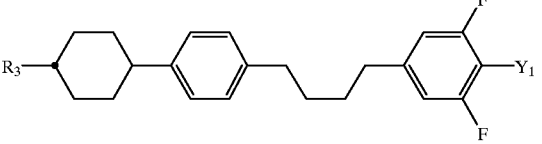

(6-34) 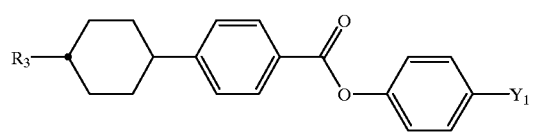
(6-35) 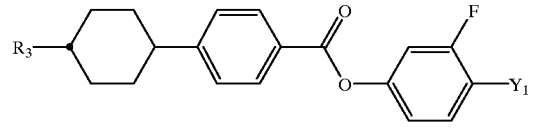
(6-36) 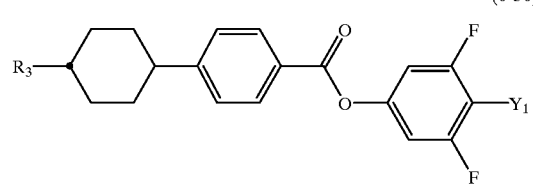
(6-37) 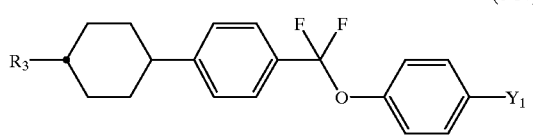
(6-38) 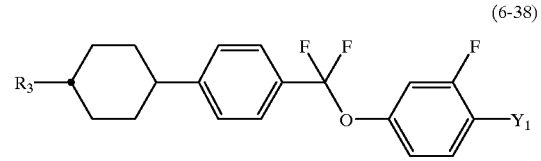
(6-39) 
(6-40) 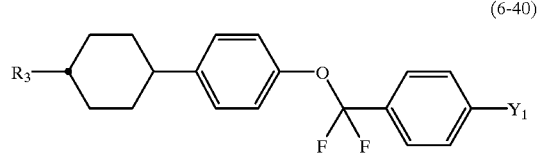
(6-41) 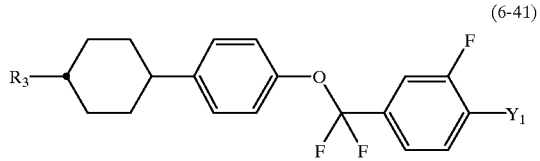
(6-42) 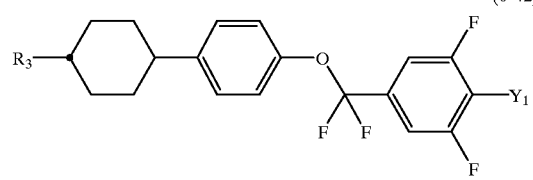
(6-43) 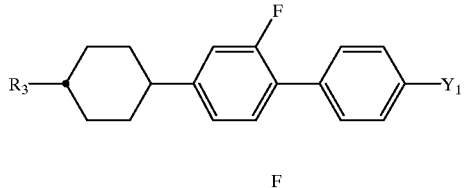
(6-44) 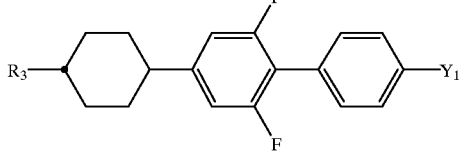
(6-45) 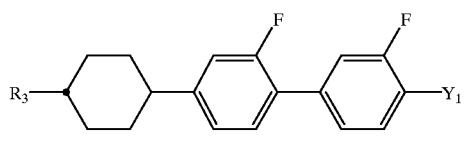
(6-46) 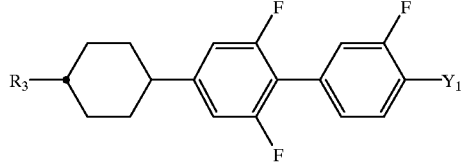
(6-47) 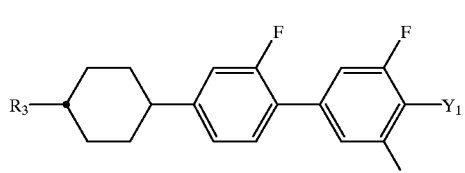
(6-48) 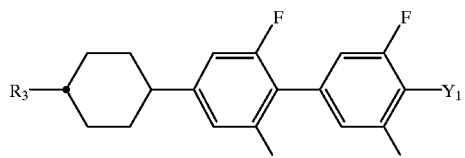
(6-49) 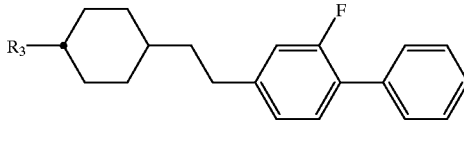
(6-50) 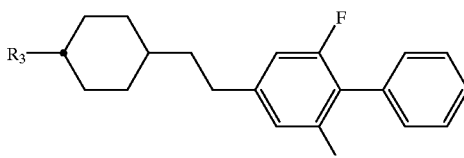
(6-51) 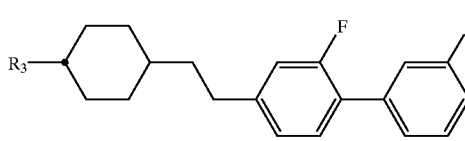

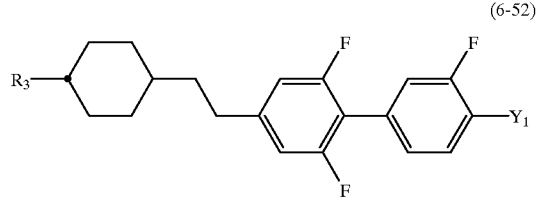 (6-52)
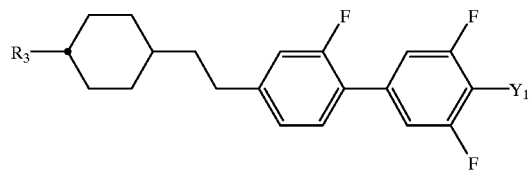 (6-53)
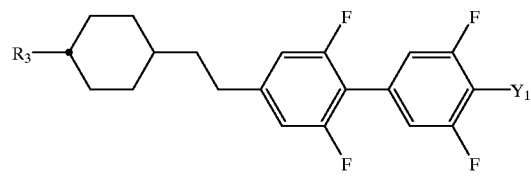 (6-54)
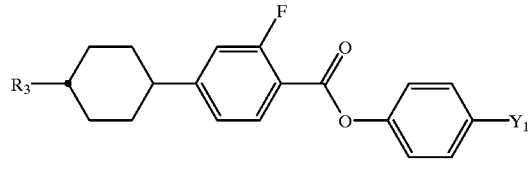 (6-55)
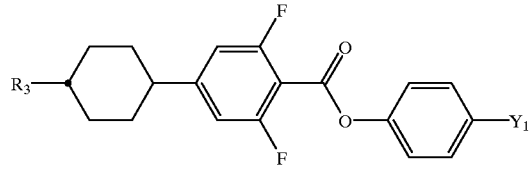 (6-56)
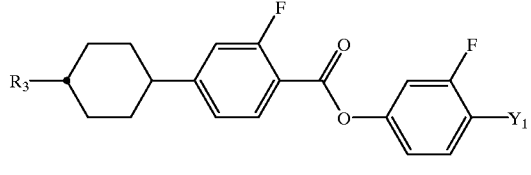 (6-57)
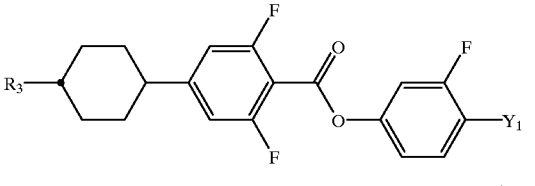 (6-58)
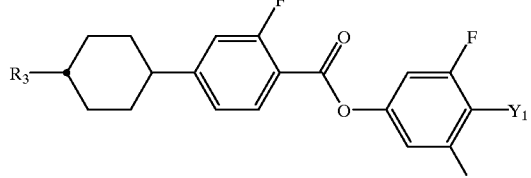 (6-59)
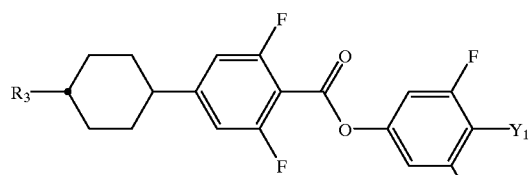 (6-60)
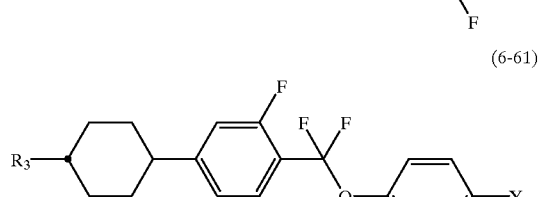 (6-61)
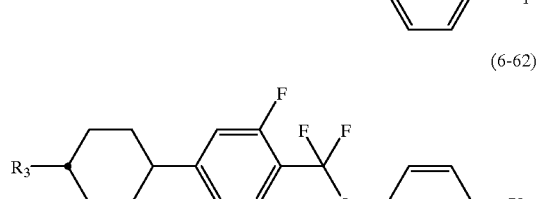 (6-62)
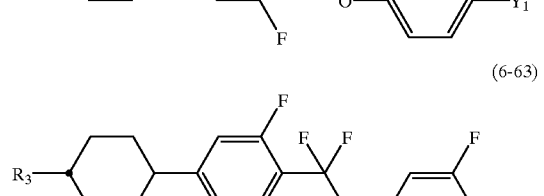 (6-63)
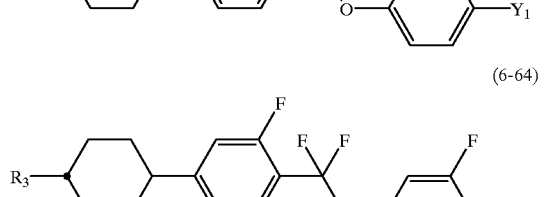 (6-64)
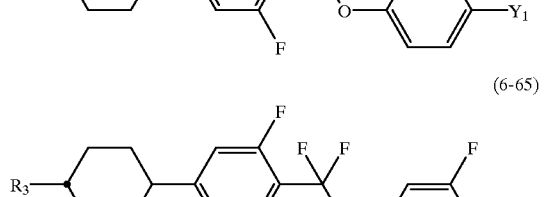 (6-65)
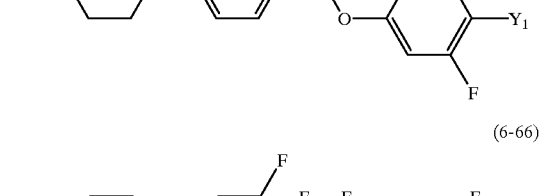 (6-66)
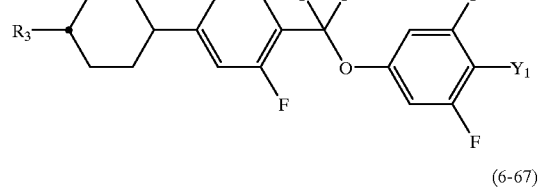 (6-67)
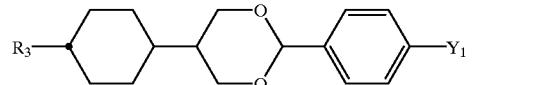

(6-68)
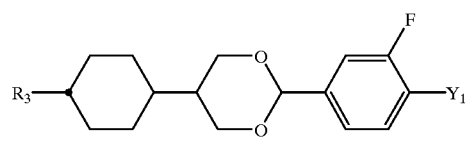
(6-69)
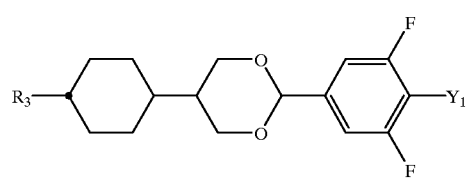
(7-1)
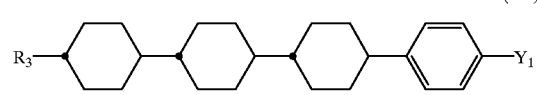
(7-2)
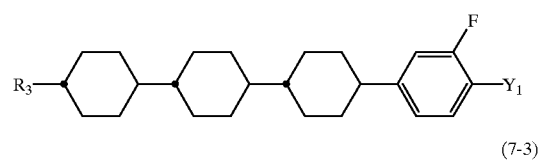
(7-3)
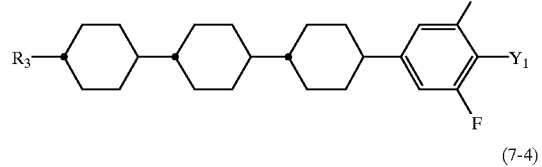
(7-4)
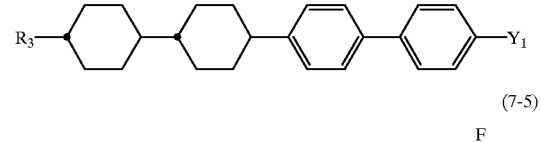
(7-5)
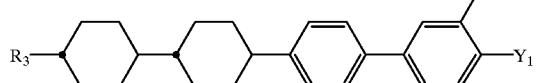
(7-6)
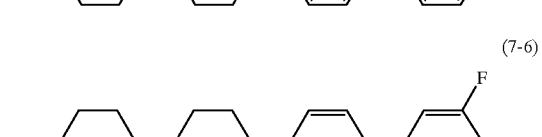
(7-7)
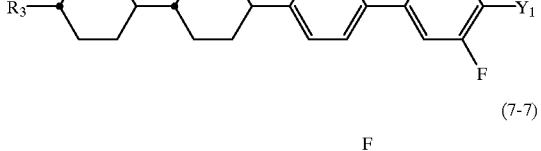
(7-8)
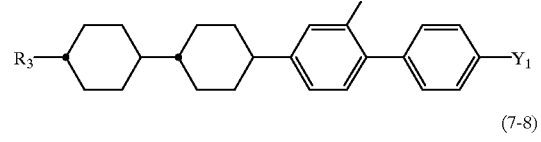
(7-9)
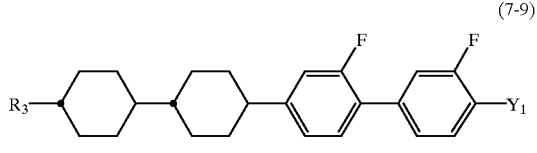
(7-10)
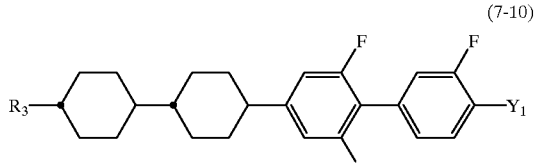
(7-11)
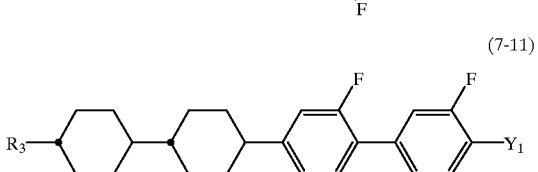
(7-12)
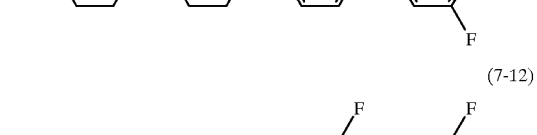
(7-13)
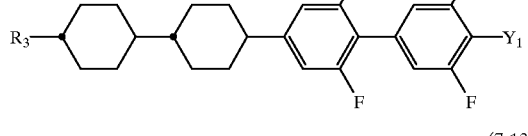
(7-14)
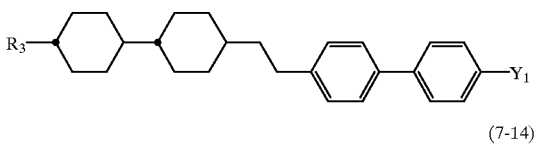
(7-15)
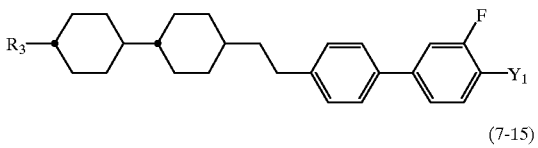
(7-16)
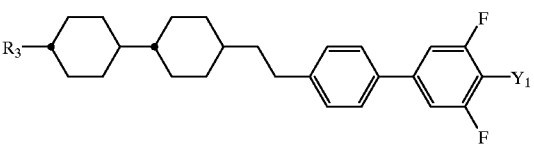
(7-17)
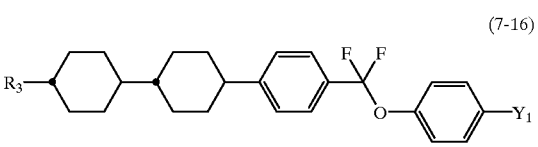
(7-18)
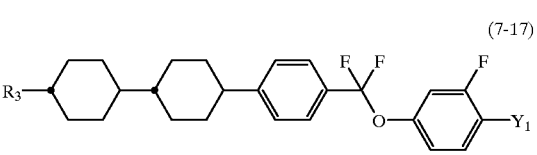

(7-19)
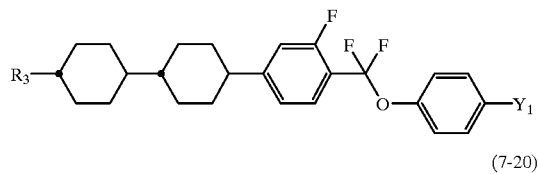

(7-20)
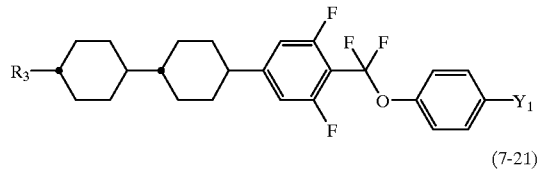

(7-21)
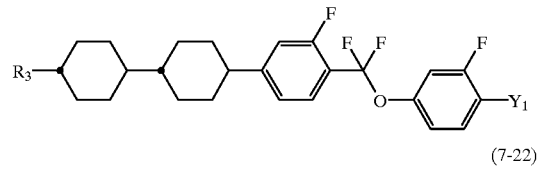

(7-22)
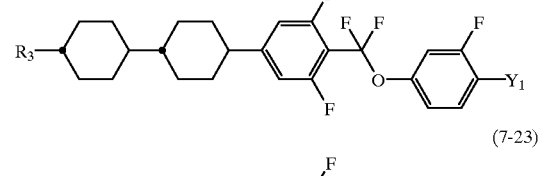

(7-23)
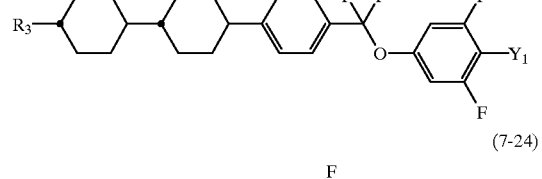

(7-24)
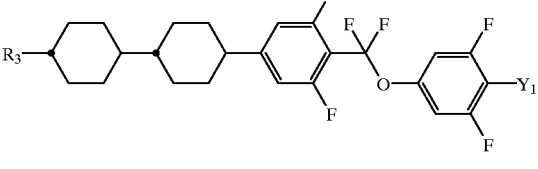

wherein $R_3$ and $Y_1$ have the same meaning as described above.

Any compounds expressed by one of these general formulas (5) to (7) exhibit a positive $\Delta\epsilon$, are considerably excellent in thermal stability and chemical stability, and are indispensable when liquid crystal compositions for TFT (AM-LCD) of which a high reliability such as a high voltage holding ratio (large specific resistivity) is required.

The amount of the compound to be used is suitably in the range of 1 to 99.9% by weight based on the total amount of liquid crystal composition when liquid crystal compositions for TFT are produced, and the amount is preferably 10 to 97% by weight, and more desirably 40 to 95% by weight. In that case, the compositions may further comprise a compound expressed by one of the general formulas (10) to (12) for the purpose of adjusting viscosity.

Compounds expressed by one of the general formulas (5) to (7) can be used when liquid crystal compositions for STN display mode or TN display mode are produced. However, since the compounds are relatively low in the effect of lowering threshold voltage of liquid crystal compositions, their amount to be used is preferably less than 50% by weight based on the total amount of liquid crystal composition.

Next, among the second component B, compounds expressed by one of the formulas (8-1) to (8-40) can be mentioned as preferable examples of the compounds included in the general formula (8), and compounds expressed by one of the formulas (9-1) to (9-3) can be mentioned as preferable examples of the compounds included in the general formula (9), respectively.

(8-1)
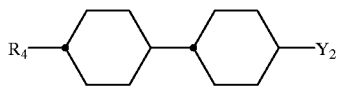

(8-2)
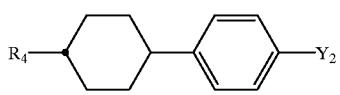

(8-3)

(8-4)

(8-5)

(8-6)
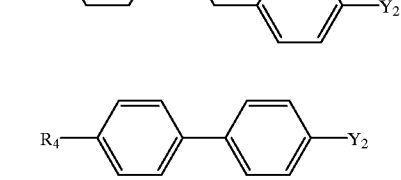

(8-7)
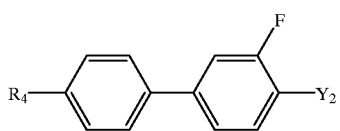

(8-8)
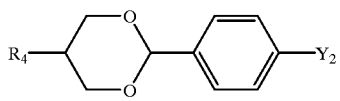

(8-9)
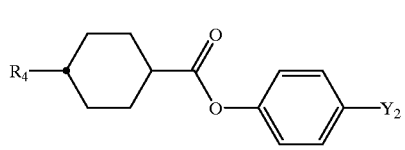

(8-10)
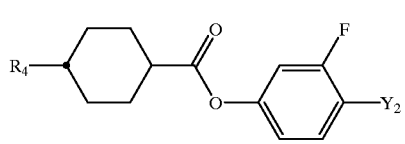

-continued (8-11)
(8-12)
(8-13)
(8-14)
(8-15)
(8-16)
(8-17)
(8-18)
(8-19)
(8-20)

-continued (8-21)
(8-22)
(8-23)
(8-24)
(8-25)
(8-26)
(8-27)
(8-28)
(8-29)
(8-30)

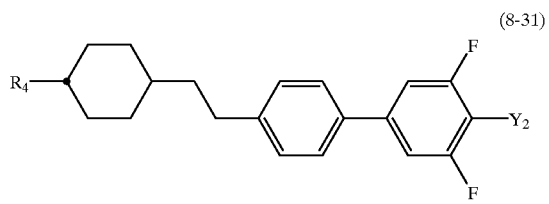
(8-31)

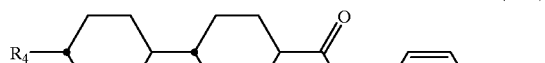
(8-32)

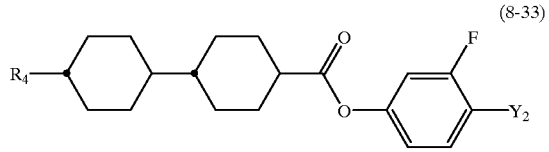
(8-33)

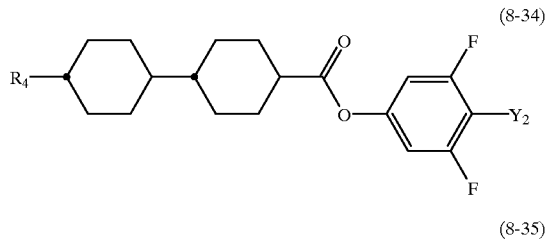
(8-34)

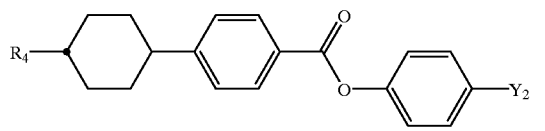
(8-35)

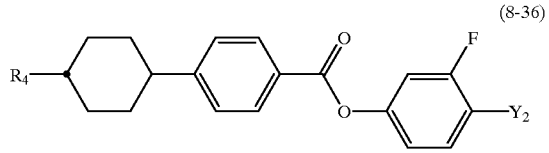
(8-36)

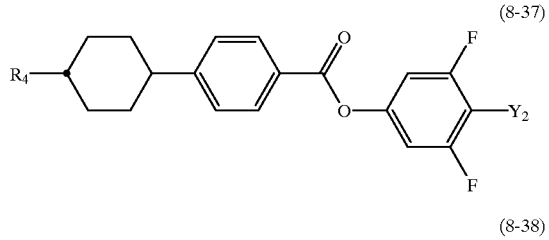
(8-37)

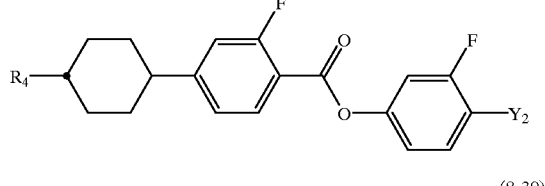
(8-38)

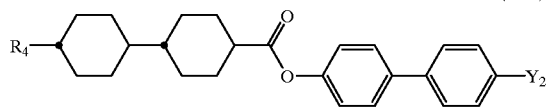
(8-39)

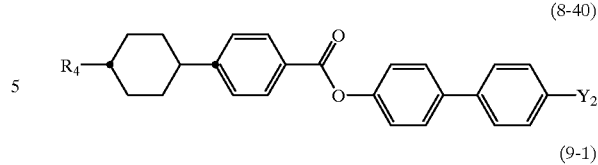
(8-40)

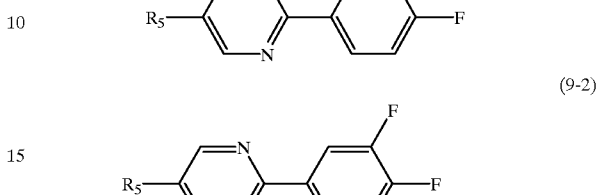
(9-1)

(9-2)

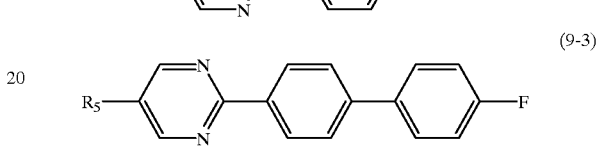
(9-3)

wherein $R_4$, $Y_2$, and $R_5$ have the same meaning as described above.

Compounds expressed by one of these general formula (8) or (9) have a positive and large dielectric anisotropy value $\Delta\epsilon$, and used particularly for the purpose of lowering threshold voltage of liquid crystal compositions.

Also, they are used for the purpose of improving the steepness of liquid crystal compositions for STN display mode or TN display mode, including for the purpose of adjusting $\Delta n$, and widening nematic range such as raising clearing point, and thus they are indispensable compounds when liquid crystal compositions for STN display mode or TN display mode are produced.

As the amount of the compounds to be used is increased, threshold voltage of liquid crystal compositions can be lowered, but on the other hand, viscosity is increased. Accordingly, it is advantageous, for low voltage driving, to use a large amount of the compound so far as viscosity of liquid crystal compositions satisfies a required characteristic.

According to such circumstances, when liquid crystal compositions for STN display mode or TN display mode are produced, the amount of the compounds to be used is suitably in the range of 0.1 to 99.9% by weight based on the total amount of liquid crystal composition, and the amount is preferably 10 to 97% by weight and more desirably 40 to 95% by weight.

Among the third component described above, compounds expressed by one of the formula (10-1) to (10-11) can be mentioned as preferable examples of the compounds included in the general formula (10), compounds expressed by one of the formulas (11-1) to (11-18) can be mentioned as preferable examples of the compounds included in the general formula (11), and compounds expressed by one of the formulas (12-1) to (12-6) can be mentioned as preferable examples of the compounds included in the general formula (12), respectively.

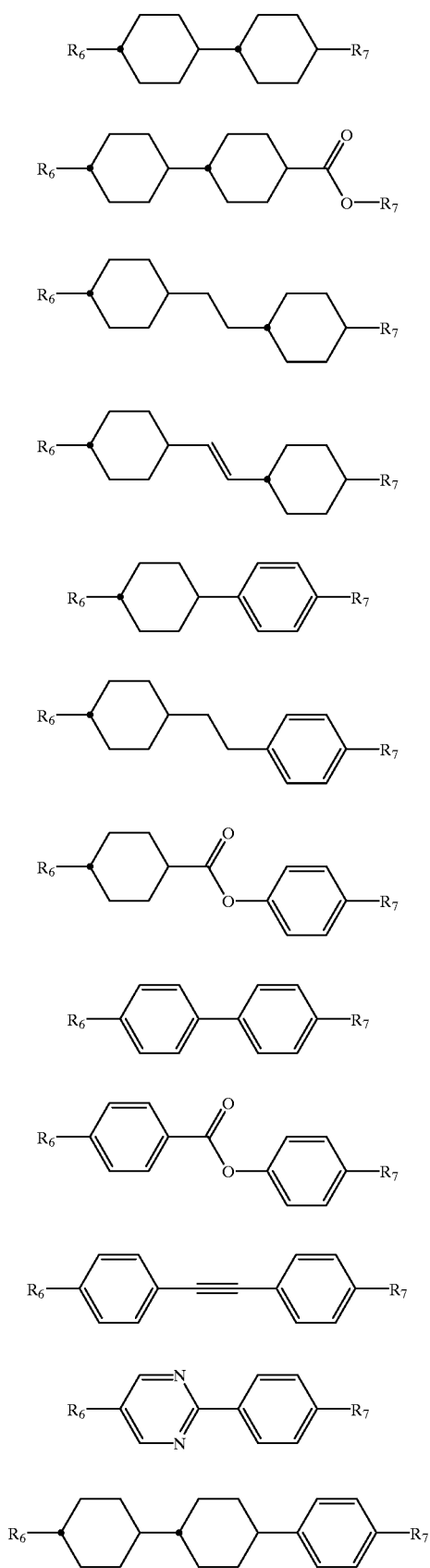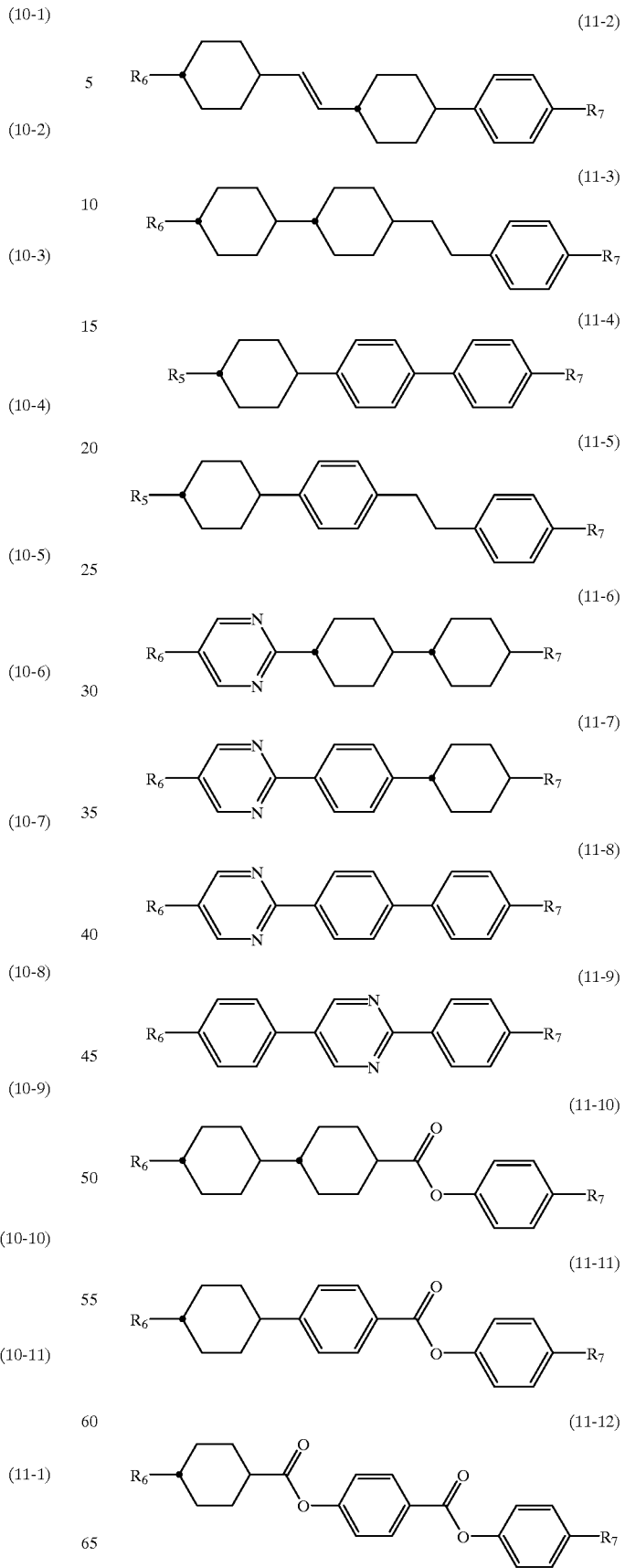

-continued (11-13)
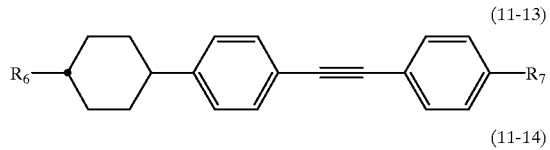

(11-14)
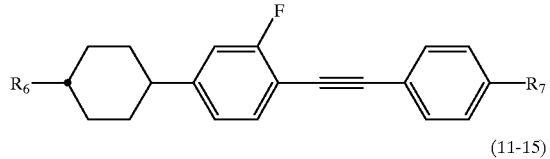

(11-15)
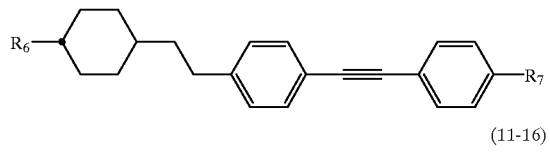

(11-16)
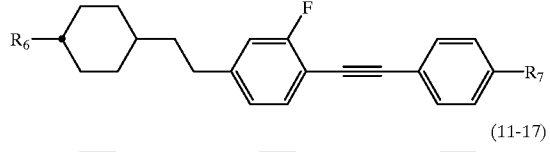

(11-17)
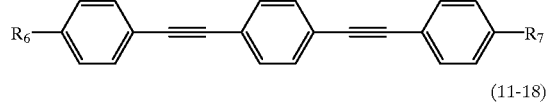

(11-18)
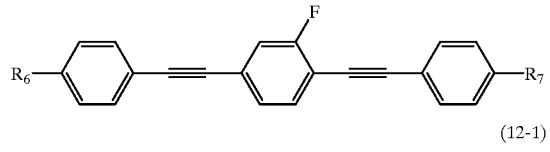

(12-1)
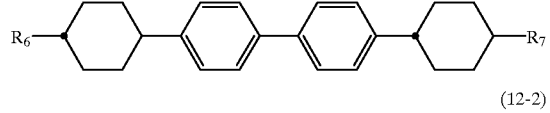

(12-2)
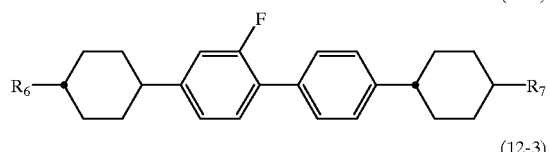

(12-3)
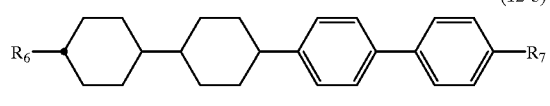

(12-4)
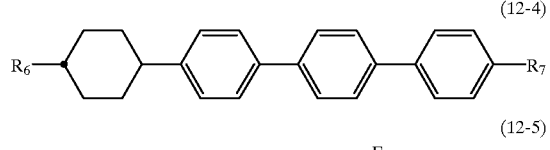

(12-5)
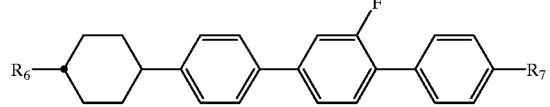

-continued (12-6)
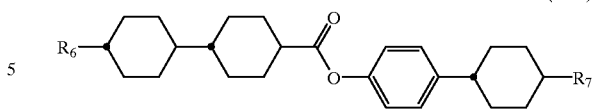

wherein $R_6$ and $R_7$ have the same meaning as described above.

Any compound expressed by one of these general formulas (10) to (12) has a small absolute value of dielectric anisotropy $\Delta\epsilon$. Among them, compounds of the general formula (10) are used principally for the purpose of adjusting viscosity or adjusting $\Delta n$ of liquid crystal compositions, and the compounds of the general formula (11) or (12) are used for the purpose of widening nematic range such as raising clearing point, and for the purpose of adjusting $\Delta n$.

With the increase of the amount to be used, this compound raises threshold voltage of liquid crystal compositions, but on the other hand, reduces viscosity. Accordingly, it is desirable to use a large amount of the compound so far as threshold voltage of liquid crystal compositions satisfies a required value.

According to such circumstances, when liquid crystal compositions for TFT are produced, the amount of the compound to be used is suitably less than 40% by weight based on the total amount of liquid crystal composition, and preferably less than 35% by weight.

On the other hand, when liquid crystal compositions for STN display mode or TN display mode are produced, the amount of the compound to be used is suitably less than 70% by weight, and preferably less than 60% by weight.

With the exception of such specific cases as liquid crystal compositions for OCB (Optically Compensated Birefringence) mode, an optically active compound, among the other components, is usually added to the liquid crystal compositions for the purpose of inducing helical structure of liquid crystal composition to adjust required twist angle and to prevent reverse twist.

While the optically active compound is selected from a wide range of known compounds, the optically active compound expressed by one of the following formulas (Op-1) to (Op-8) can preferably be mentioned:

(Op-1)
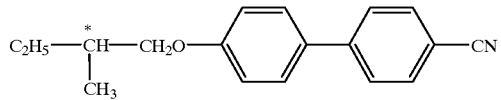

-continued

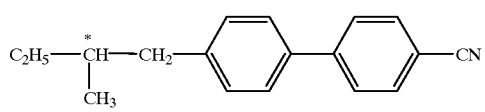
(Op-2)

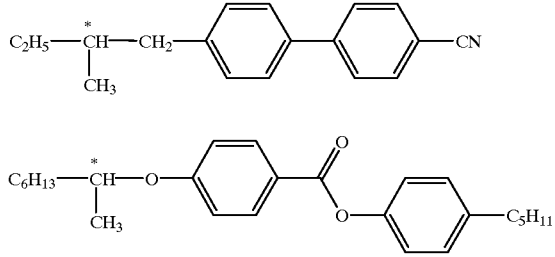
(Op-3)

(Op-4)

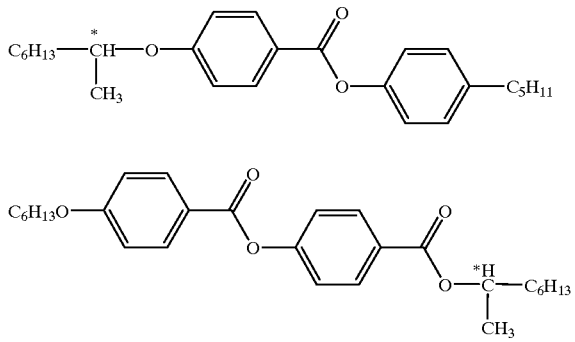

(Op-5)

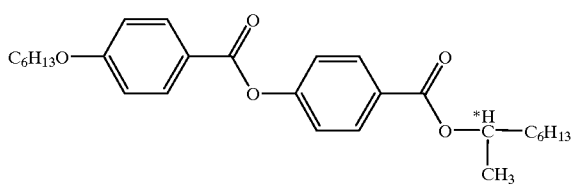

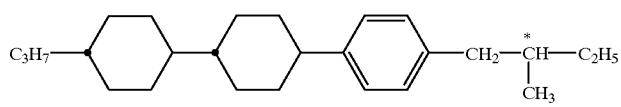
(Op-6)

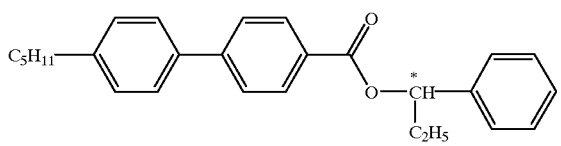
(Op-7)

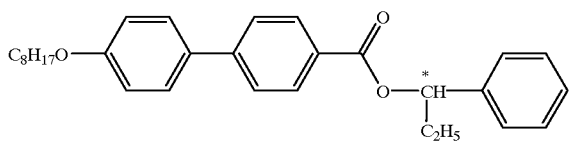
(Op-8)

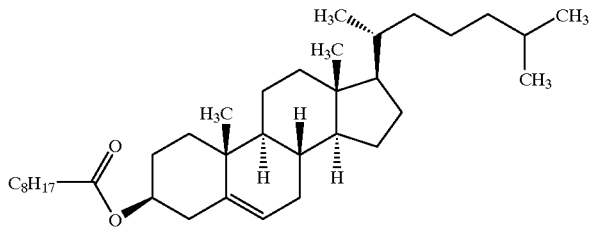

By the addition of these optically active compounds, the pitch length of twist of liquid crystal compositions are adjusted. The pitch length of twist is preferably adjusted in the range of 40 to 200 μm in the case of liquid crystal compositions for TFT or TN, and preferably adjusted in the range of 6 to 20 μm in the case of liquid crystal compositions for STN. In the case for bistable TN mode, it is preferable to adjust the pitch length in the range of 1.5 to 4 μm. In such cases, two or more kind of optically active compounds may be added for the purpose of adjusting the dependency of the pitch length on temperature.

Liquid crystal compositions provided according to the present invention can be produced by methods which are conventional by themselves. For instance, the liquid crystal compositions are usually produced by a method in which various components are dissolved in one another at a high temperature.

Further, the liquid crystal compositions of the present invention can be used as ones for guest-host (GH) mode by adding a dichroic dye such as merocyanine type, styryl type, azo type, azomethine type, azoxy type, quinophthalone type, anthraquinone type, and tetrazine type thereto. Alternatively, the liquid crystal compositions of the present invention can be used as NCAP which is prepared by the microencapsulation of a nematic liquid crystal, or as liquid crystal compositions for polymer dispersed liquid crystal display devices (PDLCD) represented by polymer net work liquid crystal display devices (PNLCD) prepared by forming a polymer of three-dimensional reticulated structure in a liquid crystal. Still further, the liquid crystal compositions of the present invention can be used as ones for electrically controlled birefringence (ECB) mode or dynamic scattering (DS) mode.

While the liquid crystal compositions of the present invention are produced by such methods as described above, the following Composition Examples 1 to 46 can be mentioned as their examples:

In each of the Composition Examples, compounds are designated by making a particular group or structure shown in the column of left side terminal group, bonding group, ring structure, or right side terminal group in Table 1 below correspond to the symbol shown in the same line and the same column. Designation in the case where the hydrogen atom on trans-1,4-cyclohexylene and trans,trans-bicyclohexane-4,4'-diyl group is replaced by its isotope, heavy hydrogen (deuterium) atom is shown by symbol [1D,~8D] after excerpting only substituted heavy hydrogen atoms, when both of the groups mentioned above are assumed to be expressed by the formula (60) and (61), respectively, and any one of hydrogen atoms $L^1$, $L^2$, $L^3$, $L^4$, $L^5$, $L^6$, $L^7$, and $L^8$ on the ring is assumed to be replaced by one of heavy hydrogen atoms 1D, 2D, 3D, 4D, 5D, 6D, 7D, and 8D.

Compound No. appended to the compounds of the present invention in the following Composition Examples means that the compounds are the same as those shown in Examples described below and having the same appended Compound No.; and the content of compounds means % by weight unless otherwise specified.

Further, data of characteristics in Composition Examples are indicated by $T_{NI}$ (phase transition temperature of nematic phase-isotropic liquid, or clearing point), $T_{MP}$ (crystallization temperature), η (viscosity: determined at 20.0° C.), Δn (optical anisotropy value: determined at 25.0° C.), Δε (dielectric anisotropy value: determined at 25.0° C.), $V_{th}$ (threshold voltage: determined at 25.0° C.), and P (pitch: determined at 25.0° C.).

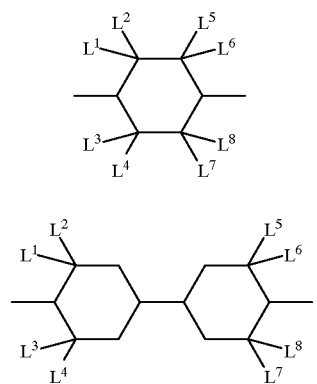

(60)

(61)

TABLE 1

Method for Designating Compounds by Using Symbols
R-(A$_1$)-Z$_1$- . . . -Z$_n$-(A$_n$)-X

| 1) Left side terminal group R- | Symbol |
|---|---|
| $C_nH_{2n+1}$— | n- |
| $C_nH_{2n+1}O$— | nO— |
| $C_nH_{2n+1}OC_mH_{2m}$— | nOm- |
| $CH_2$=CH— | V— |
| $CH_2$=CHC$_n$H$_{2n}$— | Vn- |
| $C_nH_{2n+1}CH$=CHC$_m$H$_{2m}$— | nVm- |
| $C_nH_{2n+1}CH$=CHC$_m$H$_{2m}$CH=CHC$_k$H$_{2k}$— | nVmVk- |
| F— | F— |
| NC— | C— |
| FC$_n$H$_{2n}$— | Fn- |
| FF—C$_n$H$_{2n-1}$— | FFn- |

TABLE 1-continued

Method for Designating Compounds by Using Symbols
R-(A$_1$)-Z$_1$- . . . -Z$_n$-(A$_n$)-X

| 2) Ring structure -(A$_1$)-, -(A$_n$)- | Symbol |
|---|---|
| | B |
| | B(F) |
| | B(2F, 3F) |
| | B(F, F) |
| | H |
| | Py |
| | G |
| | Ch |

| 3) Bonding group -Z$_1$-, -Z$_n$- | Symbol |
|---|---|
| —C$_2$H$_4$— | 2 |
| —C$_4$H$_8$— | 4 |
| —COO— | E |
| —C≡C— | T |
| —CH=CH— | V |
| —CF$_2$O— | CF2O |
| —OCF$_2$— | OCF2 |

| 4) Right side terminal group -X | Symbol |
|---|---|
| —F | —F |
| —Cl | —CL |
| —CN | —C |
| —CF$_3$ | —CF3 |
| —OCF$_3$ | —OCF3 |
| —OCF$_2$H | —OCF2H |
| —OCF$_2$CF$_2$H | —OCF2CF2H |
| —C$_n$H$_{2n+1}$ | -n |
| —OC$_n$H$_{2n+1}$ | —On |

TABLE 1-continued

Method for Designating Compounds by Using Symbols
R-(A$_1$)-Z$_1$- ... -Z$_n$-(A$_n$)-X

| | |
|---|---|
| —COOCH$_3$ | -EMe |
| —C$_n$H$_{2n}$CH=CH$_2$ | -nV |
| —C$_m$H$_{2m}$CH=CHC$_n$H$_{2n+1}$ | -mVn |
| —C$_m$H$_{2m}$CH=CHC$_n$H$_{2n}$F | -mVnF |
| —CH=CF$_2$ | —VFF |
| —C$_n$H$_{2n}$CH=CF$_2$ | -nVFF |
| —C≡C—CN | -TC |
| —C≡C—CH=CH—CN | -TVC |
| —CH=CH—C≡C—CN | —VTC |
| —C≡C—C≡C—CN | -TTC |

| 5) Example of designation | Symbol |
|---|---|
| Example 1 | 3-H2B(F, F)B(F)—F |

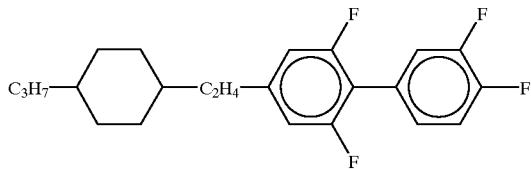

| Example 2 | 3-HB(F)TB-2 |
|---|---|

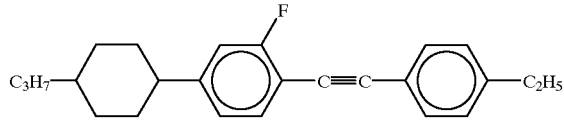

| Example 3 | 1V2-BEB(F, F)—C |
|---|---|

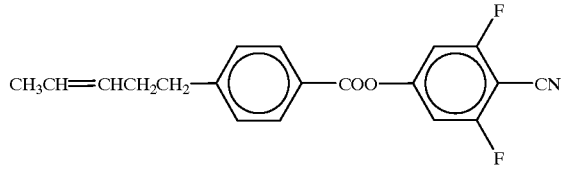

COMPOSITION EXAMPLE 1

Liquid crystal composition comprising the following compounds in the amount shown below was prepared:

| | |
|---|---|
| 3-HB-TTC (No. 62) | 10.0% |
| 1V2-BEB(F,F)-C | 5.0% |
| 3-HB-C | 15.0% |
| 1-BTB-3 | 5.0% |
| 2-BTB-1 | 10.0% |
| 3-HH-4 | 11.0% |
| 3-HHB-1 | 11.0% |
| 3-HHB-3 | 9.0% |
| 3-H2BTB-2 | 4.0% |
| 3-H2BTB-3 | 4.0% |
| 3-H2BTB-4 | 4.0% |
| 3-HB(F)TB-2 | 6.0% |
| 3-HB(F)TB-3 | 6.0% |

Characteristics of this composition were determined to be as follows:

T$_{NI}$=104.7° C.
η=14.6 mPa·s
εn=0.190
Δε=7.0
V$_{th}$=2.21 V.

Further, 0.8 part by weight of the optically active compound expressed by the formula (Op-4) was added to 100 parts by weight of the primary liquid crystal composition described above to obtain a secondary liquid crystal composition, and a characteristic of the secondary composition was determined to be as follows:

P=11.2 μm.

COMPOSITION EXAMPLE 2

Liquid crystal composition comprising the following compounds in the amount shown below was prepared:

| | |
|---|---|
| 5-HH-VTC (No. 34) | 5.0% |
| V2-HB-C | 12.0% |
| 1V2-HB-C | 12.0% |
| 3-HB-C | 10.0% |
| 3-H[1D,2D,3D]B-C | 9.0% |
| 3-HB(F)-C | 5.0% |
| 2-BTB-1 | 2.0% |
| 3-HH-4 | 8.0% |
| 3-HH-VFF | 6.0% |
| 2-H[1D,2D,3D]HB-C | 3.0% |
| 3-HHB-C | 6.0% |
| 3-HB(F)TB-2 | 8.0% |
| 3-H2BTB-2 | 5.0% |
| 3-H2BTB-3 | 5.0% |
| 3-H2BTB-4 | 4.0% |

Characteristics of this composition were determined to be as follows:

T$_{NI}$=95.0° C.
η=18.1 mPa·s
Δn=0.158
Δε=8.5
V$_{th}$=2.14 V.

COMPOSITION EXAMPLE 3

Liquid crystal composition comprising the following compounds in the amount shown below was prepared:

| | |
|---|---|
| 3-HH-TTC (No. 58) | 5.0% |
| V-HB-TTC (No. 64) | 5.0% |
| 3O1-BEB(F)-C | 10.0% |
| 4O1-BEB(F)-C | 13.0% |
| 5O1-BEB(F)-C | 13.0% |
| 2-HHB(F)-C | 15.0% |
| 3-HHB(F)-C | 15.0% |
| 3-HB(F)TB-2 | 4.0% |
| 3-HB(F)TB-3 | 4.0% |
| 3-HB(F)TB-4 | 4.0% |
| 3-HHB-1 | 8.0% |
| 3-HHB-O1 | 4.0% |

Characteristics of this composition were determined to be as follows:

T$_{NI}$=110.4° C.
η=85.5 mPa·s
Δn=0.175
Δε=27.8
V$_{th}$=1.12 V.

COMPOSITION EXAMPLE 4

Liquid crystal composition comprising the following compounds in the amount shown below was prepared:

| | |
|---|---|
| 3-HPy-TTC (No. 67) | 3.0% |
| 5-PyB-F | 4.0% |
| 3-PyB(F)-F | 4.0% |
| 2-BB-C | 5.0% |
| 4-BB-C | 4.0% |
| 5-BB-C | 5.0% |
| 2-PyB-2 | 2.0% |
| 3-PyB-2 | 2.0% |
| 4-PyB-2 | 2.0% |
| 6-PyB-O5 | 3.0% |
| 6-PyB-O6 | 3.0% |
| 6-PyB-O7 | 3.0% |
| 3-PyBB-F | 6.0% |
| 4-PyBB-F | 6.0% |
| 5-PyBB-F | 6.0% |
| 3-HHB-1 | 6.0% |
| 3-HHB-3 | 8.0% |
| 2-H2BTB-2 | 4.0% |
| 2-H2BTB-3 | 4.0% |
| 2-H2BTB-4 | 5.0% |
| 3-H2BTB-2 | 5.0% |
| 3-H2BTB-3 | 5.0% |
| 3-H2BTB-4 | 5.0% |

COMPOSITION EXAMPLE 5

Liquid crystal composition comprising the following compounds in the amount shown below was prepared:

| | |
|---|---|
| 3-HHH-VTC (No. 84) | 3.0% |
| 3-GB-C | 10.0% |
| 4-GB-C | 10.0% |
| 2-BEB-C | 12.0% |
| 3-BEB-C | 4.0% |
| 3-PyB(F)-F | 6.0% |
| 3-HEB-O4 | 8.0% |
| 4-HEB-O2 | 6.0% |
| 5-HEB-O1 | 6.0% |
| 3-HEB-O2 | 5.0% |
| 5-HEB-O2 | 4.0% |
| 5-HEB-5 | 5.0% |
| 4-HEB-5 | 5.0% |
| 1O-BEB-2 | 4.0% |
| 3-HHB-1 | 3.0% |
| 3-HHEBB-C | 3.0% |
| 3-HBEBB-C | 3.0% |
| 5-HBEBB-C | 3.0% |

COMPOSITION EXAMPLE 6

Liquid crystal composition comprising the following compounds in the amount shown below was prepared:

| | |
|---|---|
| C-BHH-VTC (No. 89) | 2.0% |
| 3-HB-C | 18.0% |
| 7-HB-C | 3.0% |
| 1O1-HB-C | 10.0% |
| 3-HB(F)-C | 10.0% |
| 2-PyB-2 | 2.0% |
| 3-PyB-2 | 2.0% |
| 4-PyB-2 | 2.0% |
| 1O1-HH-3 | 7.0% |
| 2-BTB-O1 | 7.0% |
| 3-HHB-1 | 7.0% |
| 3-HHB-F | 4.0% |
| 3-HHB-O1 | 4.0% |
| 3-HHB-3 | 6.0% |
| 3-H2BTB-2 | 3.0% |
| 3-H2BTB-3 | 3.0% |

-continued

| | |
|---|---|
| 2-PyBH-3 | 4.0% |
| 3-PyBH-3 | 3.0% |
| 3-PyBB-2 | 3.0% |

COMPOSITION EXAMPLE 7

Liquid crystal composition comprising the following compounds in the amount shown below was prepared:

| | |
|---|---|
| F-BHH-VTC (No. 90) | 3.0% |
| 2O1-BEB(F)-C | 5.0% |
| 3O1-BEB(F)-C | 12.0% |
| 5O1-BEB(F)-C | 4.0% |
| 1V2-BEB(F,F)-C | 10.0% |
| 3-HH-EMe | 10.0% |
| 3-HB-O2 | 18.0% |
| 7-HEB-F | 2.0% |
| 3-HHEB-F | 2.0% |
| 5-HHEB-F | 2.0% |
| 3-HBEB-F | 4.0% |
| 2O1-HBEB(F)-C | 2.0% |
| 3-HB(F)EB(F)-C | 2.0% |
| 3-HBEB(F,F)-C | 2.0% |
| 3-HHB-F | 4.0% |
| 3-HHB-O1 | 4.0% |
| 3-HHB-3 | 10.0% |
| 3-HEBEB-F | 2.0% |
| 3-HEBEB-1 | 2.0% |

COMPOSITION EXAMPLE 8

Liquid crystal composition comprising the following compounds in the amount shown below was prepared:

| | |
|---|---|
| 3-HB2B-VTC (No. 121) | 3.0% |
| 5-BEB(F)-C | 5.0% |
| V-HB-C | 11.0% |
| 5-PyB-C | 6.0% |
| 4-BB-3 | 11.0% |
| 3-HH-2V | 10.0% |
| 5-HH-V | 11.0% |
| V-HHB-1 | 7.0% |
| V2-HHB-1 | 15.0% |
| 3-HHB-1 | 6.0% |
| 1V2-HBB-2 | 10.0% |
| 3-HHEBH-3 | 5.0% |

COMPOSITION EXAMPLE 9

Liquid crystal composition comprising the following compounds in the amount shown below was prepared:

| | |
|---|---|
| 3-HBHB-TTC (N0. 156) | 2.0% |
| 2O1-BEB(F)-C | 5.0% |
| 3O1-BEB(F)-C | 12.0% |
| 5O1-BEB(F)-C | 4.0% |
| 1V2-BEB(F,F)-C | 16.0% |
| 3-HB-O2 | 10.0% |
| 3-HH-4 | 3.0% |
| 3-HHB-F | 3.0% |
| 3-HHB-1 | 8.0% |
| 3-HHB-O1 | 4.0% |
| 3-HBEB-F | 4.0% |
| 3-HHEB-F | 6.0% |

-continued

| | |
|---|---|
| 5-HHEB-F | 6.0% |
| 3-H2BTB-2 | 4.0% |
| 3-H2BTB-3 | 4.0% |
| 3-H2BTB-4 | 4.0% |
| 3-HB(F)TB-2 | 5.0% |

COMPOSITION EXAMPLE 10

Liquid crystal composition comprising the following compounds in the amount shown below was prepared:

| | |
|---|---|
| 3-HVHB-TTC (No. 151) | 3.0% |
| 2-BEB-C | 12.0% |
| 3-BEB-C | 4.0% |
| 4-BEB-C | 6.0% |
| 3-HB-C | 25.0% |
| 3-HEB-O4 | 12.0% |
| 4-HEB-O2 | 8.0% |
| 5-HEB-O1 | 8.0% |
| 3-HEB-O2 | 6.0% |
| 5-HEB-O2 | 5.0% |
| 3-HHB-1 | 7.0% |
| 3-HHB-O1 | 4.0% |

COMPOSITION EXAMPLE 11

Liquid crystal composition comprising the following compounds in the amount shown below was prepared:

| | |
|---|---|
| 3-HBTB-TTC (No. 174) | 3.0% |
| 2-BEB-C | 10.0% |
| 5-BB-C | 12.0% |
| 7-BB-C | 7.0% |
| 1-BTB-3 | 7.0% |
| 2-BTB-1 | 7.0% |
| 1O-BEB-2 | 10.0% |
| 1O-BEB-5 | 12.0% |
| 2-HHB-1 | 4.0% |
| 3-HHB-F | 4.0% |
| 3-HHB-1 | 7.0% |
| 3-HHB-O1 | 4.0% |
| 3-HHB-3 | 13.0% |

COMPOSITION EXAMPLE 12

Liquid crystal composition comprising the following compounds in the amount shown below was prepared:

| | |
|---|---|
| 3-GHB-TTC (No. 142) | 2.0% |
| 1V2-BEB(F,F)-C | 8.0% |
| 3-HB-C | 10.0% |
| V2V-HB-C | 12.0% |
| V2V-HH-3 | 19.0% |
| 3-HB-O2 | 4.0% |
| 3-HHB-1 | 10.0% |
| 3-HHB-3 | 15.0% |
| 3-HB(F)TB-2 | 4.0% |
| 3-HB(F)TB-3 | 4.0% |
| 3-H2BTB-2 | 4.0% |
| 3-H2BTB-3 | 4.0% |
| 3-H2BTB-4 | 4.0% |

COMPOSITION EXAMPLE 13

Liquid crystal composition comprising the following compounds in the amount shown below was prepared:

| | |
|---|---|
| 3-HB-TTC (No. 62) | 5.0% |
| 5-HH-VTC (No. 34) | 5.0% |
| 3-HH-TTC (No. 59) | 5.0% |
| V-HB-TTC (No. 64) | 5.0% |
| 5-BTB(F)TB-3 | 10.0% |
| V2-HB-TC | 10.0% |
| 3-HB-TC | 5.0% |
| 5-HB-C | 7.0% |
| 5-BB-C | 3.0% |
| 2-BTB-1 | 5.0% |
| 2-BTB-O1 | 5.0% |
| 3-HH-4 | 5.0% |
| 3-HHB-1 | 10.0% |
| 3-HHB-3 | 11.0% |
| 3-H2BTB-2 | 3.0% |
| 3-H2BTB-3 | 3.0% |
| 3-HB(F)TB-2 | 3.0% |

Characteristics of this composition were determined to be as follows:

$T_{NI} = 127.5°$ C.

$\eta = 18.7$ mPa·s $\Delta n = 0.238$ $\Delta\epsilon = 5.8$ $V_{th} = 2.58$ V.

COMPOSITION EXAMPLE 14

Liquid crystal composition comprising the following compounds in the amount shown below was prepared:

| | |
|---|---|
| 3-HB2BB-TTC (No. 231) | 2.0% |
| 1V2-BEB(F,F)-C | 6.0% |
| 3-HB-C | 18.0% |
| 2-BTB-1 | 10.0% |
| 5-HH-VFF | 30.0% |
| 1-BHH-VFF | 8.0% |
| 1-BHH-2VFF | 11.0% |
| 3-H2BTB-2 | 5.0% |
| 3-H2BTB-3 | 4.0% |
| 3-H2BTB-4 | 4.0% |
| 3-HHB-1 | 2.0% |

COMPOSITION EXAMPLE 15

Liquid crystal composition comprising the following compounds in the amount shown below was prepared:

| | |
|---|---|
| 3-HPy-TTC (No. 67) | 2.0% |
| 2-HB-C | 5.0% |
| 3-HB-C | 12.0% |
| 3-HB-O2 | 15.0% |
| 2-BTB-1 | 3.0% |
| 3-HHB-1 | 8.0% |
| 3-HHB-F | 4.0% |
| 3-HHB-O1 | 5.0% |
| 3-HHB-3 | 12.0% |
| 3-HHEB-F | 4.0% |
| 5-HHEB-F | 4.0% |
| 2-HHB(F)-F | 7.0% |
| 3-HHB(F)-F | 7.0% |
| 5-HHB(F)-F | 7.0% |
| 3-HHB(F,F)-F | 5.0% |

COMPOSITION EXAMPLE 16

Liquid crystal composition comprising the following compounds in the amount shown below was prepared:

| | |
|---|---|
| 3-HB-TTC (No. 62) | 5.0% |
| V-HB-TTC (No. 64) | 5.0% |
| 2-HHB(F)-F | 17.0% |
| 3-HHB(F)-F | 17.0% |
| 5-HHB(F)-F | 16.0% |
| 2-H2HB(F)-F | 10.0% |
| 3-H2HB(F)-F | 5.0% |
| 2-HBB(F)-F | 6.0% |
| 3-HBB(F)-F | 6.0% |
| 5-HBB(F)-F | 13.0% |

Characteristics of this composition were determined to be as follows:

$T_{NI}$=108.1° C.

$\eta$=26.6 mPa·s $\Delta n$=0.127

$\Delta\epsilon$=5.9

$V_{th}$=1.87 V.

Further, 0.3 part by weight of the optically active compound expressed by the formula (Op-8) was added to 100 parts by weight of the primary liquid crystal composition described above to obtain a secondary liquid crystal composition, and a characteristic of the secondary composition was determined to be as follows:

P=77.4 μm.

COMPOSITION EXAMPLE 17

Liquid crystal composition comprising the following compounds in the amount shown below was prepared:

| | |
|---|---|
| 5-HH-VTC (No. 34) | 3.0% |
| V-HB-VTC (No. 39) | 3.0% |
| 7-HB(F)-F | 5.0% |
| 5-H2B(F)-F | 5.0% |
| 3-HB-O2 | 10.0% |
| 3-HH-4 | 2.0% |
| 3-HH[5D,6D,7D]-4 | 3.0% |
| 2-HHB(F)-F | 10.0% |
| 3-HHB(F)-F | 10.0% |
| 5-HH[5D,6D,7D]B(F)-F | 10.0% |
| 3-H2HB(F)-F | 5.0% |
| 2-HBB(F)-F | 3.0% |
| 3-HBB(F)-F | 3.0% |
| 2-H2BB(F)-F | 5.0% |
| 3-H2BB(F)-F | 6.0% |
| 3-HHB-1 | 8.0% |
| 3-HHB-O1 | 5.0% |
| 3-HHB-3 | 4.0% |

Characteristics of this composition were determined to be as follows:

$T_{NI}$=95.4° C.

$\eta$=17.7 mPa·s $\Delta n$=0.100

$\Delta\epsilon$=3.4

$V_{th}$=2.52 V.

COMPOSITION EXAMPLE 18

Liquid crystal composition comprising the following compounds in the amount shown below was prepared:

| | |
|---|---|
| 3-HB-TTC (No. 62) | 8.0% |
| 3-HH-TTC (No. 58) | 8.0% |
| 7-HB(F,F)-F | 3.0% |
| 3-HB-O2 | 7.0% |
| 2-HHB(F)-F | 10.0% |
| 3-HHB(F)-F | 10.0% |
| 5-HHB(F)-F | 10.0% |
| 2-HBB(F)-F | 9.0% |
| 3-HBB(F)-F | 9.0% |
| 2-HBB-F | 4.0% |
| 3-HBB-F | 4.0% |
| 5-HBB-F | 3.0% |
| 3-HBB(F,F)-F | 5.0% |
| 5-HBB(F,F)-F | 10.0% |

Characteristics of this composition were determined to be as follows:

$T_{NI}$=103.0° C.

$\eta$=22.8 mPa·s $\Delta n$=0.151

$\Delta\epsilon$=6.5

$V_{th}$=1.56 V.

COMPOSITION EXAMPLE 19

Liquid crystal composition comprising the following compounds in the amount shown below was prepared:

| | |
|---|---|
| 3-HHH-VTC (No. 84) | 2.0% |
| 7-HB(F,F)-F | 3.0% |
| 3-H2HB(F,F)-F | 10.0% |
| 4-H2HB(F,F)-F | 10.0% |
| 5-H2HB(F,F)-F | 10.0% |
| 3-HHB(F,F)-F | 5.0% |
| 4-HHB(F,F)-F | 5.0% |
| 3-HH2B(F,F)-F | 15.0% |
| 5-HH2B(F,F)-F | 10.0% |
| 3-HBB(F,F)-F | 12.0% |
| 5-HBB(F,F)-F | 12.0% |
| 3-HBCF2OB(F,F)-F | 6.0% |

COMPOSITION EXAMPLE 20

Liquid crystal composition comprising the following compounds in the amount shown below was prepared:

| | |
|---|---|
| C-BHH-VTC (No. 89) | 2.0% |
| 7-HB(F,F)-F | 5.0% |
| 3-H2HB(F,F)-F | 12.0% |
| 4-H2HB(F,F)-F | 10.0% |
| 3-HHB(F,F)-F | 10.0% |
| 4-HHB(F,F)-F | 5.0% |
| 3-HBB(F,F)-F | 10.0% |
| 3-HHEB(F,F)-F | 10.0% |
| 4-HHEB(F,F)-F | 3.0% |
| 5-HHEB(F,F)-F | 3.0% |
| 2-HBEB(F,F)-F | 3.0% |
| 3-HBEB(F,F)-F | 3.0% |
| 5-HBEB(F,F)-F | 3.0% |
| 3-HGB(F,F)-F | 15.0% |
| 3-HHBB(F,F)-F | 6.0% |

COMPOSITION EXAMPLE 21

Liquid crystal composition comprising the following compounds in the amount shown below was prepared:

| | |
|---|---|
| F-BHH-VTC (No. 90) | 2.0% |
| 3-HB-CL | 10.0% |
| 5-HB-CL | 4.0% |
| 7-HB-CL | 4.0% |
| 1O1-HH-5 | 5.0% |
| 2-HBB(F)-F | 8.0% |
| 3-HBB(F)-F | 8.0% |
| 5-HBB(F)-F | 12.0% |
| 4-HHB-CL | 8.0% |
| 5-HHB-CL | 8.0% |
| 3-H2HB(F)-CL | 4.0% |
| 3-HBB(F,F)-F | 10.0% |
| 5-H2BB(F,F)-F | 9.0% |
| 3-HB(F)VB-2 | 4.0% |
| 3-HB(F)VB-3 | 4.0% |

COMPOSITION EXAMPLE 22

Liquid crystal composition comprising the following compounds in the amount shown below was prepared:

| | |
|---|---|
| 3-HB2B-VTC (No. 121) | 3.0% |
| 3-HHB(F,F)-F | 9.0% |
| 3-H2HB(F,F)-F | 8.0% |
| 4-H2HB(F,F)-F | 8.0% |
| 5-H2HB(F,F)-F | 8.0% |
| 3-HBB(F,F)-F | 18.0% |
| 5-HBB(F,F)-F | 20.0% |
| 3-H2BB(F,F)-F | 10.0% |
| 5-HHBB(F,F)-F | 3.0% |
| 5-HHEBB-F | 2.0% |
| 3-HH2BB(F,F)-F | 3.0% |
| 1O1-HBBH-4 | 4.0% |
| 1O1-HBBH-5 | 4.0% |

COMPOSITION EXAMPLE 23

Liquid crystal composition comprising the following compounds in the amount shown below was prepared:

| | |
|---|---|
| 3-HEHB-TTC (No. 156) | 2.0% |
| 5-HB-F | 12.0% |
| 6-HB-F | 9.0% |
| 7-HB-F | 7.0% |
| 2-HHB-OCF3 | 7.0% |
| 3-HHB-OCF3 | 7.0% |
| 4-HHB-OCF3 | 5.0% |
| 5-HHB-OCF3 | 5.0% |
| 3-HH2B-OCF3 | 4.0% |
| 5-HH2B-OCF3 | 4.0% |
| 3-HHB(F,F)-OCF3 | 5.0% |
| 3-HBB(F)-F | 10.0% |
| 5-HBB(F)-F | 10.0% |
| 3-HH2B(F)-F | 3.0% |
| 3-HB(F)BH-3 | 3.0% |
| 5-HBBH-3 | 3.0% |
| 3-HHB(F,F)-OCF2H | 4.0% |

COMPOSITION EXAMPLE 24

Liquid crystal composition comprising the following compounds in the amount shown below was prepared:

| | |
|---|---|
| 3-HVHB-TTC (No. 151) | 2.0% |
| 5-H4HB(F,F)-F | 7.0% |
| 5-H4HB-OCF3 | 15.0% |
| 3-H4HB(F,F)-CF3 | 8.0% |
| 5-H4HB(F,F)-CF3 | 10.0% |
| 3-HB-CL | 6.0% |
| 5-HB-CL | 4.0% |
| 2-H2BB(F)-F | 5.0% |
| 3-H2BB(F)-F | 8.0% |
| 5-HVHB(F,F)-F | 5.0% |
| 3-HHB-OCF3 | 5.0% |
| 3-H2HB-OCF3 | 5.0% |
| V-HHB(F)-F | 5.0% |
| 3-HHB(F)-F | 5.0% |
| 5-HHEB-OCF3 | 2.0% |
| 3-HBEB(F,F)-F | 5.0% |
| 5-HH-V2F | 3.0% |

COMPOSITION EXAMPLE 25

Liquid crystal composition comprising the following compounds in the amount shown below was prepared:

| | |
|---|---|
| 3-HBTB-TTC (No. 174) | 2.0% |
| 2-HHB(F)-F | 2.0% |
| 3-HHB(F)-F | 2.0% |
| 5-HHB(F)-F | 2.0% |
| 2-HBB(F)-F | 6.0% |
| 3-HBB(F)-F | 6.0% |
| 5-HBB(F)-F | 10.0% |
| 2-H2BB(F)-F | 9.0% |
| 3-H2BB(F)-F | 9.0% |
| 3-HBB(F,F)-F | 23.0% |
| 5-HBB(F,F)-F | 19.0% |
| 1O1-HBBH-4 | 5.0% |
| 1O1-HBBH-5 | 5.0% |

Further, 0.25 part by weight of the optically active compound expressed by the formula (Op-5) was added to 100 parts by weight of this primary liquid crystal composition described above to obtain a secondary liquid crystal composition, and a characteristic of the secondary composition was determined to be as follows:

P=77.4 µm.

COMPOSITION EXAMPLE 26

Liquid crystal composition comprising the following compounds in the amount shown below was prepared:

| | |
|---|---|
| 3-GHB-TTC (No. 142) | 2.0% |
| 5-HB-CL | 12.0% |
| 3-HH-4 | 7.0% |
| 3-HB-O2 | 20.0% |
| 3-H2HB(F,F)-F | 8.0% |
| 3-HHB(F,F)-F | 6.0% |
| 3-HBB(F,F)-F | 6.0% |
| 2-HHB(F)-F | 5.0% |
| 3-HHB(F)-F | 5.0% |
| 5-HHB(F)-F | 5.0% |
| 2-H2HB(F)-F | 2.0% |
| 3-H2HB(F)-F | 1.0% |
| 5-H2HB(F)-F | 2.0% |
| 3-HHBB(F,F)-F | 4.0% |
| 3-HBCF2OB-OCF3 | 4.0% |

-continued

| | |
|---|---|
| 5-HBCF2OB(F,F)-CF3 | 4.0% |
| 3-HHB-1 | 3.0% |
| 3-HHB-O1 | 4.0% |

COMPOSITION EXAMPLE 27

Liquid crystal composition comprising the following compounds in the amount shown below was prepared:

| | |
|---|---|
| 3-H2B-TVC (No. 249) | 15.0% |
| 3-HB-C | 20.0% |
| 5-HB-C | 31.0% |
| 7-HB-C | 21.0% |
| 5-HBB-C | 13.0% |

Characteristics of this composition were determined to be as follows:

$T_{NI}$=84.4° C.
$T_{MP}$<−20° C.
$\eta$=30.5 mPa·s
$\Delta n$=0.1610
$\Delta\epsilon$=11.3
$V_{th}$=1.70 V.

COMPOSITION EXAMPLE 28

Liquid crystal composition comprising the following compounds in the amount shown below was prepared:

| | |
|---|---|
| 2-HB-TVC (No. 246) | 15.0% |
| 3-HB-C | 20.0% |
| 5-HB-C | 31.0% |
| 7-HB-C | 21.0% |
| 5-HBB-C | 13.0% |

Characteristics of this composition were determined to be as follows:

$T_{NI}$=83.0° C.
$T_{MP}$<−20° C.
$\eta$=30.4 mPa·s
$\Delta n$=0.162
$\Delta\epsilon$=11.8
$V_{th}$=1.57 V.

COMPOSITION EXAMPLE 29

Liquid crystal composition comprising the following compounds in the amount shown below was prepared:

| | |
|---|---|
| 3-H2B-TVC (No. 249) | 11.0% |
| 1V2-BEB(F,F)-C | 5.0% |
| 3-HB-C | 20.0% |
| 1-BTB-3 | 5.0% |
| 2-BTB-1 | 10.0% |
| 3-HH-4 | 11.0% |
| 3-HHB-1 | 11.0% |
| 3-HHB-3 | 9.0% |
| 3-H2BTB-2 | 4.0% |

-continued

| | |
|---|---|
| 3-H2BTB-3 | 4.0% |
| 3-H2BTB-4 | 4.0% |
| 3-HB(F)TB-2 | 6.0% |

Characteristics of this composition were determined to be as follows:

$T_{NI}$=95.3° C.
$T_{MP}$<−30° C.
$\eta$=17.2 mPa·s
$\Delta n$=0.174
$\Delta\epsilon$=7.8
$V_{th}$=1.91 V.

Further, 0.8 part by weight of the optically active compound expressed by the formula (Op-4) was added to 100 parts by weight of the primary liquid crystal composition described above to obtain a secondary liquid crystal composition, and a characteristic of the secondary composition was determined to be as follows:

P=11.5 $\mu$m.

COMPOSITION EXAMPLE 30

Liquid crystal composition comprising the following compounds in the amount shown below was prepared:

| | |
|---|---|
| 2-HB-TVC (No. 246) | 11.0% |
| V2-HB-C | 12.0% |
| 1V2-HB-C | 12.0% |
| 3-HB-C | 10.0% |
| 3-H[1D,2D,3D]-C | 9.0% |
| 3-HB(F)-C | 5.0% |
| 2-BTB-1 | 2.0% |
| 3-HH-4 | 8.0% |
| 3-HH-VFF | 6.0% |
| 2-H[1D,2D,3D]HB-C | 3.0% |
| 3-HHB-C | 6.0% |
| 3-HB(F)TB-2 | 8.0% |
| 3-H2BTB-2 | 5.0% |
| 3-H2BTB-3 | 3.0% |

Characteristics of this composition were determined to be as follows:

$T_{NI}$=92.6° C.
$T_{MP}$<−30° C.
$\eta$=19.9 mPa·s
$\Delta n$=0.166
$\Delta\epsilon$=9.6
$V_{th}$=1.80 V.

COMPOSITION EXAMPLE 31

Liquid crystal composition comprising the following compounds in the amount shown below was prepared:

| | |
|---|---|
| V-HB-TVC (No. 252) | 8.0% |
| 2O1-BEB(F)-C | 5.0% |
| 3O1-BEB(F)-C | 15.0% |
| 4O1-BEB(F)-C | 13.0% |
| 5O1-BEB(F)-C | 13.0% |
| 2-HHB(F)-C | 15.0% |
| 3-HHB(F)-C | 15.0% |

-continued

| | |
|---|---|
| 3-HB(F)TB-2 | 4.0% |
| 3-HHB-1 | 8.0% |
| 3-HHB-O1 | 4.0% |

Characteristics of this composition were determined to be as follows:

$T_{NI}$=89.2° C.
$T_{MP}$<−30° C.
$\eta$=89.1 mPa·s
$\Delta n$=0.157
$\Delta\epsilon$=32.3
$V_{th}$=0.82 V.

COMPOSITION EXAMPLE 32

Liquid crystal composition comprising the following compounds in the amount shown below was prepared:

| | |
|---|---|
| 2-HB-TVC (No. 246) | 10.0% |
| 5-H2B-TVC (No. 250) | 10.0% |
| 5-PyB-F | 4.0% |
| 3-PyB(F)-F | 4.0% |
| 2-BB-C | 5.0% |
| 4-BB-C | 4.0% |
| 5-BB-C | 5.0% |
| 2-PyB-2 | 2.0% |
| 3-PyB-2 | 2.0% |
| 4-PyB-2 | 2.0% |
| 6-PyB-O5 | 3.0% |
| 6-PyB-O6 | 3.0% |
| 6-PyB-O7 | 3.0% |
| 6-PyB-O8 | 3.0% |
| 3-PyBB-F | 6.0% |
| 4-PyBB-F | 6.0% |
| 5-PyBB-F | 6.0% |
| 3-HHB-1 | 6.0% |
| 3-HHB-3 | 8.0% |
| 2-H2BTB-2 | 4.0% |
| 2-H2BTB-3 | 4.0% |

Characteristics of this composition were determined to be as follows:

$T_{NI}$=87.4° C.
$T_{MP}$<−20° C.
$\eta$=40.6 mPa·s
$\Delta n$=0.213
$\Delta\epsilon$=9.5
$V_{th}$=1.86 V.

COMPOSITION EXAMPLE 33

Liquid crystal composition comprising the following compounds amount shown below was prepared:

| | |
|---|---|
| 3-HB-TVC (No. 247) | 10.0% |
| 3-DB-C | 10.0% |
| 4-DB-C | 10.0% |
| 2-BEB-C | 12.0% |
| 3-BEB-C | 4.0% |
| 3-PyB(F)-F | 6.0% |
| 3-HEB-O4 | 8.0% |
| 4-HEB-O2 | 6.0% |
| 3-HEB-O2 | 5.0% |
| 5-HEB-5 | 5.0% |
| 4-HEB-5 | 5.0% |
| 1O-BEB-2 | 4.0% |
| 3-HHB-1 | 6.0% |
| 3-HHEBB-C | 3.0% |
| 3-HBEBB-C | 3.0% |
| 5-HBEBB-C | 3.0% |

Characteristics of this composition were determined to be as follows:

$T_{NI}$=77.9° C.
$\eta$=42.6 mPa·s
$\Delta n$=0.144
$\Delta\epsilon$=13.0
$V_{th}$=1.20 V.

COMPOSITION EXAMPLE 34

Liquid crystal composition comprising the following compounds in the amount shown below was prepared:

| | |
|---|---|
| V2-HB-TVC (No. 253) | 6.0% |
| 3-HB-C | 18.0% |
| 7-HB-C | 3.0% |
| 1O1-HB-C | 10.0% |
| 3-HB(F)-C | 10.0% |
| 2-PyB-2 | 2.0% |
| 3-PyB-2 | 2.0% |
| 4-PyB-2 | 2.0% |
| 1O1-HH-3 | 7.0% |
| 2-BTB-O1 | 7.0% |
| 3-HHB-1 | 7.0% |
| 3-HHB-F | 4.0% |
| 3-HHB-O1 | 4.0% |
| 3-HHB-3 | 8.0% |
| 3-H2BTB-2 | 3.0% |
| 2-PyBH-3 | 4.0% |
| 3-PyBB-2 | 3.0% |

Characteristics of this composition were determined to be as follows:

$T_{NI}$=78.2° C.
$\eta$=18.8 mPa·s
$\Delta n$=0.144
$\Delta\epsilon$=8.9
$V_{th}$=1.68 V.

COMPOSITION EXAMPLE 35

Liquid crystal composition comprising the following compounds in the amount shown below was prepared:

| | |
|---|---|
| V-HB-TVC (No. 252) | 7.0% |
| 5-BEB(F)-C | 5.0% |
| V-HB-C | 11.0% |
| 5-PyB-C | 6.0% |
| 4-BB-3 | 11.0% |
| 3-HH-2V | 10.0% |
| 5-HH-V | 5.0% |
| V2V-HH-3 | 6.0% |
| V-HHB-1 | 7.0% |
| V2-HHB-1 | 15.0% |

-continued

| | |
|---|---|
| 3-HHB-1 | 9.0% |
| 1V2-HBB-2 | 3.0% |
| 3-HHEBH-3 | 5.0% |

Characteristics of this composition were determined to be as follows:

$T_{NI}$=92.3° C.

$\eta$=17.0 mPa·s $\Delta n$=0.123

$\Delta\epsilon$=5.8

$V_{th}$=2.28 V.

COMPOSITION EXAMPLE 36

Liquid crystal composition comprising the following compounds in the amount shown below was prepared:

| | |
|---|---|
| 3-H2B-TVC (No. 249) | 10.0% |
| 2-HB-TVC (No. 246) | 10.0% |
| V-HB-TVC (No. 252) | 5.0% |
| V2-HB-TVC (No. 253) | 5.0% |
| 2O1-BEB(F)-C | 5.0% |
| 3O1-BEB(F)-C | 12.0% |
| 5O1-BEB(F)-C | 4.0% |
| 1V2-BEB(F,F)-C | 16.0% |
| 3-HB-O2 | 6.0% |
| 3-HH-4 | 3.0% |
| 3-HHB-F | 3.0% |
| 3-HHB-1 | 3.0% |
| 3-HHB-O1 | 4.0% |
| 3-HBEB-F | 4.0% |
| 3-HHEB-F | 3.0% |
| 3-H2BTB-2 | 4.0% |
| 3-HB(F)TB-2 | 3.0% |

Characteristics of this composition were determined to be as follows:

$T_{NI}$=93.3° C.

$\eta$=49.1 mPa·s $\Delta n$=0.189

$\Delta\epsilon$=32.2

$V_{th}$=0.88 V.

COMPOSITION EXAMPLE 37

Liquid crystal composition comprising the following compounds in the amount shown below was prepared:

| | |
|---|---|
| 2-HB-TVC (No. 246) | 6.0% |
| V-HB-TVC (No. 252) | 7.0% |
| 2-BEB-C | 10.0% |
| 5-BB-C | 12.0% |
| 7-BB-C | 7.0% |
| 1-BTB-3 | 7.0% |
| 2-BTB-1 | 10.0% |
| 1O-BEB-2 | 10.0% |
| 1O-BEB-5 | 12.0% |
| 2-HHB-1 | 4.0% |
| 3-HHB-F | 4.0% |
| 3-HHB-1 | 7.0% |
| 3-HHB-O1 | 4.0% |

Characteristics of this composition were determined to be as follows:

$T_{NI}$=65.8° C.

$\eta$=23.6 mPa·s $\Delta n$=0.185

$\Delta\epsilon$=8.5

$V_{th}$=1.61 V.

COMPOSITION EXAMPLE 38

Liquid crystal composition comprising the following compounds in the amount shown below was prepared:

| | |
|---|---|
| 3-HB-TVC (No. 247) | 5.0% |
| 5-BTB(F)TB-3 | 10.0% |
| V2-HB-TC | 10.0% |
| 3-HB-TC | 10.0% |
| 3-HB-C | 10.0% |
| 5-HB-C | 7.0% |
| 5-BB-C | 3.0% |
| 2-BTB-1 | 10.0% |
| 2-BTB-O1 | 5.0% |
| 3-HH-4 | 3.0% |
| 3-HHB-1 | 10.0% |
| 3-HHB-3 | 11.0% |
| 3-H2BTB-2 | 3.0% |
| 3-HB(F)TB-2 | 3.0% |

Characteristics of this composition were determined to be as follows:

$T_{NI}$=101.5° C.

$\eta$=15.7 mPa·s $\Delta n$=0.213

$\Delta\epsilon$=7.4

$V_{th}$=2.00 V.

COMPOSITION EXAMPLE 39

Liquid crystal composition comprising the following compounds in the amount shown below was prepared:

| | |
|---|---|
| 2-HB-TVC (No. 246) | 10.0% |
| 1V2-BEB(F,F)-C | 6.0% |
| 3-HB-C | 18.0% |
| 2-BTB-1 | 8.0% |
| 5-HH-VFF | 30.0% |
| 1-BHH-VFF | 8.0% |
| 1-BHH-2VFF | 11.0% |
| 3-H2BTB-2 | 5.0% |
| 3-HHB-1 | 4.0% |

Characteristics of this composition were determined to be as follows:

$T_{NI}$=81.3° C.

$\eta$=14.9 mPa·s $\Delta n$=0.135

$\Delta\epsilon$=8.0

$V_{th}$=1.89 V.

COMPOSITION EXAMPLE 40

Liquid crystal composition comprising the following compounds in the amount shown below was prepared:

| | |
|---|---|
| 2-HB-TVC (No. 224) | 8.0% |
| 3-HB-TVC (No. 247) | 5.0% |

-continued

| | |
|---|---|
| 2-HHB(F)-F | 17.0% |
| 3-HHB(F)-F | 17.0% |
| 5-HHB(F)-F | 16.0% |
| 2-H2HB(F)-F | 10.0% |
| 3-H2HB(F)-F | 5.0% |
| 5-H2HB(F)-F | 10.0% |
| 2-HBB(F)-F | 6.0% |
| 3-HBB(F)-F | 6.0% |

Characteristics of this composition were determined to be as follows:

$T_{NI}$=105.2° C.

η=28.5 mPa·s

Δn=0.116

Δε=6.1

$V_{th}$=2.05 V.

Further, 0.3 part by weight of the optically active compound expressed by the formula (Op-8) was added to 100 parts by weight of the primary liquid crystal composition described above to obtain a secondary liquid crystal composition, and a characteristic of the secondary composition was determined to be as follows:

P=82 μm

COMPOSITION EXAMPLE 41

Liquid crystal composition comprising the following compounds in the amount shown below was prepared:

| | |
|---|---|
| 3-H2B-TVC (No. 249) | 6.0% |
| 7-HB(F)-F | 5.0% |
| 5-H2B(F)-F | 5.0% |
| 3-HB-O2 | 10.0% |
| 3-HH-4 | 2.0% |
| 3-HH[5D,6D,7D]-4 | 3.0% |
| 2-HHB(F)-F | 10.0% |
| 3-HHB(F)-F | 10.0% |
| 5-HH[5D,6D,7D]B(F)-F | 10.0% |
| 3-H2HB(F)-F | 5.0% |
| 2-HBB(F)-F | 3.0% |
| 3-HBB(F)-F | 3.0% |
| 2-H2BB(F)-F | 5.0% |
| 3-H2BB(F)-F | 6.0% |
| 3-HHB-1 | 8.0% |
| 3-HHB-O1 | 5.0% |
| 3-HHB-3 | 4.0% |

Characteristics of this composition were determined to be as follows:

$T_{NI}$=91.7° C.

η=19.4 mPa·s

Δn=0.109

Δε=3.8

$V_{th}$=2.59 V.

COMPOSITION EXAMPLE 42

Liquid crystal composition comprising the following compounds in the amount shown below was prepared:

| | |
|---|---|
| 3-HB-TVC (No. 247) | 10.0% |
| 7-HB(F,F)-F | 5.0% |
| 3-H2HB(F,F)-F | 12.0% |
| 4-H2HB(F,F)-F | 10.0% |
| 4-HHB(F,F)-F | 5.0% |
| 3-HBB(F,F)-F | 10.0% |
| 3-HHEB(F,F)-F | 10.0% |
| 4-HHEB(F,F)-F | 3.0% |
| 5-HHEB(F,F)-F | 3.0% |
| 2-HBEB(F,F)-F | 3.0% |
| 3-HBEB(F,F)-F | 5.0% |
| 5-HBEB(F,F)-F | 3.0% |
| 3-HGB(F,F)-F | 15.0% |
| 3-HHBB(F,F)-F | 6.0% |

Characteristics of this composition were determined to be as follows:

$T_{NI}$=81.2° C.

η=36.6 mPa·s

Δn=0.107

Δε=13.5

$V_{th}$=1.32 V.

COMPOSITION EXAMPLE 43

Liquid crystal composition comprising the following compounds in the amount shown below was prepared:

| | |
|---|---|
| 3-H2B-TVC (No. 249) | 7.0% |
| 2-HB-TVC (No. 246) | 7.0% |
| 3-HB-CL | 10.0% |
| 5-HB-CL | 4.0% |
| 7-HB-CL | 4.0% |
| 1O1-HH-5 | 5.0% |
| 2-HBB(F)-F | 8.0% |
| 3-HBB(F)-F | 8.0% |
| 4-HHB-CL | 8.0% |
| 5-HHB-CL | 8.0% |
| 3-H2HB(F)-CL | 4.0% |
| 3-HBB(F,F)-F | 10.0% |
| 5-H2BB(F,F)-F | 9.0% |
| 3-HB(F)VB-2 | 4.0% |
| 3-HB(F)VB-3 | 4.0% |

Characteristics of this composition were determined to be as follows:

$T_{NI}$=98.6° C.

η=24.5 mPa·s

Δn=0.153

Δε=6.0

$V_{th}$=2.06 V.

COMPOSITION EXAMPLE 44

Liquid crystal composition comprising the following compounds in the amount shown below was prepared:

| | |
|---|---|
| 3-H2B-TVC (No. 249) | 5.0% |
| 2-HB-FVC (No. 246) | 5.0% |
| 5-HB-F | 12.0% |
| 6-HB-F | 9.0% |
| 7-HB-F | 7.0% |
| 2-HHB-OCF3 | 7.0% |
| 3-HHB-OCF3 | 7.0% |
| 4-HHB-OCF3 | 7.0% |
| 5-HHB-OCF3 | 5.0% |

-continued

| | | |
|---|---|---|
| 3-HH2B-OCF3 | 4.0% | |
| 5-HH2B-OCF3 | 4.0% | |
| 3-HHB(F,F)-OCF3 | 5.0% | |
| 3-HBB(F)-F | 10.0% | |
| 3-HH2B(F)-F | 3.0% | |
| 3-HB(F)BH-3 | 3.0% | |
| 5-HBBH-3 | 3.0% | |
| 3-HHB(F,F)-OCF2H | 4.0% | |

Characteristics of this composition were determined to be as follows:

$T_{NI}$=91.0° C.
$\eta$=17.4 mPa·s
$\Delta n$=0.109
$\Delta \epsilon$=5.5
$V_{th}$=2.20 V.

COMPOSITION EXAMPLE 45

Liquid crystal composition comprising the following compounds in the amount shown below was prepared:

| | | |
|---|---|---|
| 3-H2B-TVC (No. 249) | 5.0% | |
| 3-HB-TVC (No. 247) | 5.0% | |
| 5-H4HB(F,F)-F | 7.0% | |
| 5-H4HB-OCF3 | 15.0% | |
| 3-H4HB(F,F)-CF3 | 8.0% | |
| 5-H4HB(F,F)-CF3 | 10.0% | |
| 3-HB-CL | 6.0% | |
| 5-HB-CL | 4.0% | |
| 2-H2BB(F)-F | 5.0% | |
| 5-HVHB(F,F)-F | 5.0% | |
| 3-HHB-OCF3 | 5.0% | |
| 3-H2HB-OCF3 | 5.0% | |
| V-HHB(F)-F | 5.0% | |
| 3-HHB(F)-F | 5.0% | |
| 5-HHEB-OCF3 | 2.0% | |
| 3-HBEB(F,F)-F | 5.0% | |
| 5-HH-V2F | 3.0% | |

Characteristics of this composition were determined to be as follows:

$T_{NI}$=76.4° C.
$\eta$=27.3 mPa·s
$\Delta n$=0.112
$\Delta \epsilon$=9.2
$V_{th}$=1.58 V.

COMPOSITION EXAMPLE 46

Liquid crystal composition comprising the following compounds in the amount shown below was prepared:

| | | |
|---|---|---|
| 2-HB-TVC (No. 246) | 4.0% | |
| V-HB-TVC (No. 252) | 3.0% | |
| 5-H2B-TVC (No. 250) | 3.0% | |
| 2-HHB(F)-F | 2.0% | |
| 3-HHB(F)-F | 2.0% | |
| 5-HHB(F)-F | 2.0% | |
| 2-HBB(F)-F | 6.0% | |
| 3-HBB(F)-F | 6.0% | |
| 2-H2BB(F)-F | 9.0% | |
| 3-H2BB(F)-F | 9.0% | |
| 3-HBB(F,F)-F | 25.0% | |

-continued

| | | |
|---|---|---|
| 5-HBB(F,F)-F | 19.0% | |
| 1O1-HBBH-4 | 5.0% | |
| 1O1-HBBH-5 | 5.0% | |

Characteristics of this composition were determined to be as follows:

$T_{NI}$=101.1° C.
$\eta$=37.9 mPa·s
$\Delta n$=0.153
$\Delta \epsilon$=8.2
$V_{th}$=1.72 V.

Compounds of the present invention expressed by the general formula (1) can be produced by known general methods of organic synthesis.

Production of the compounds expressed by the general formula (1) wherein G represents the group expressed by the formula (3) or (4) described above, and ring $A_4$ is 1,4-cyclohexylene or 1,3-dioxane-2,5-diyl.

A halide expressed by the general formula (18) can readily be produced by synthesizing aldehyde (17) according to a method described in Shin-Jikken Kagaku Kouza, vol. 14, p 633 (1977), and converting it by the method (a) or (b) described below.

(a) A method described in Shin-Jikken Kagaku Kouza, vol. 14, p 633 (1977) and Organic Reactions, vol. 14, p 270 (1965) in the case where $G_1$ is 1,2-ethenylene, (b) A method described in Tetrahedron Lett., vol. 37, 2763 (1996) and Preparative Acetylenic Chemistry, second edition, ELSEVIER (1988) in the case where $G_1$ is 1,2-ethynylene.

A compound expressed by the general formula (19) can readily be obtained by subjecting the halide (18) thus formed to a coupling reaction with 2-methyl-3-butyne-2-ol in a suitable solvent in the presence of a catalyst of a transition metal complex and a promoter added when necessary (reference is mate to the literature mentioned in (b) above).

As examples of the complex catalyst described above, zero valent or divalent palladium complexes such as dichlorobistriphenylphosphine palladium, tetrakistriphenylphosphine palladium, palladium acetate, and Kharasch complex can be mentioned. While the amount of the complex catalyst to be used is not constant since it depends on the reactivity of substrates, the range of 0.1 to 20% by mol to halide (18) is generally suitable, and the range of 0.5 to 5% by mol is preferable since conversion time is short and side reactions hardly occur besides.

As example of the promoter, copper salts such as copper iodide and copper bromide can be mentioned, and the use of these salts is preferable for increasing the yield of compound (19).

As examples of most suitable solvent to be used, while diethylamine can generally be mentioned, a polar solvent such as triethylamine, pyridine, pyrrolidine, morpholine, and dimethyl formamide, and a mixed solvent of one of these solvents with another solvent can be used.

While reaction temperature may be in the range from −40° C. to the boiling point of a solvent to be used, it is preferable to use the temperature particularly between 0° C. and the boiling point of the solvent since an excellent activity of the complex catalyst can be retained and the conversion can be maintained at a high level. In this connection, since the active site of the complex catalyst is unstable against air and moisture in the reaction described above, the reaction is preferably carried out in an inert gas as a countermeasure.

The compound (19) obtained by the method described above is treated according to a method described in the Preparative Acetylenic Chemistry, second edition, ELSEVIER (1988), and led to the compound of the present invention expressed by the general formula (1).

That is, the compound (19) obtained by the method described above is treated with a base such as potassium hydroxide in a suitable solvent to readily deprotect, thereby being converted into a compound expressed by the general formula (20). A halide expressed by the general formula (21) can be synthesized by reacting the compound (20) with a base such as n-butyl lithium (n-BuLi) in an aprotic solvent such as tetrahydrofuran (THF), and then reacting with a halogen such as iodine and bromine. Compounds of the present invention included in the general formula (1) can be obtained by reacting the halide (21) with copper cyanide in a solvent such as THF and N,N-dimethyl formamide (DMF) in which a catalyst such as lithium bromide is added when required.

Subsequent to the reactions described above, the reaction solution is subjected to an after-treatment according to a conventional method, and further subjected to purifying operations such as distillation, recrystallization, and column chromatography to isolate the compound (1).

coupling reaction with halide (18) in the same manner as described above with the exception that (trimethylsilyl)acetylene is used instead of 2-methyl-3-butyne-2-ol to obtain a compound expressed by the general formula (22), and then deprotecting it with potassium fluoride in a solvent such as DMF. This compound can be converted into a compound which is an an example those of the present invention expressed by the general formula (1) by the same manner as described above.

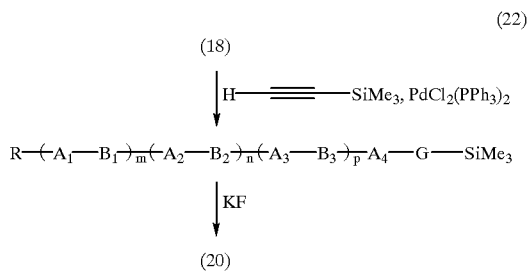

wherein R, $A_1$, $A_2$, $A_3$, $A_4$, $B_1$, $B_2$, $B_3$, G, m, n, and p have the same meaning as described above, and G represents the group expressed the formula (3) or (4).

Production of the compounds expressed by the general formula (1) wherein G represents the group expressed by the formula (2) described above:

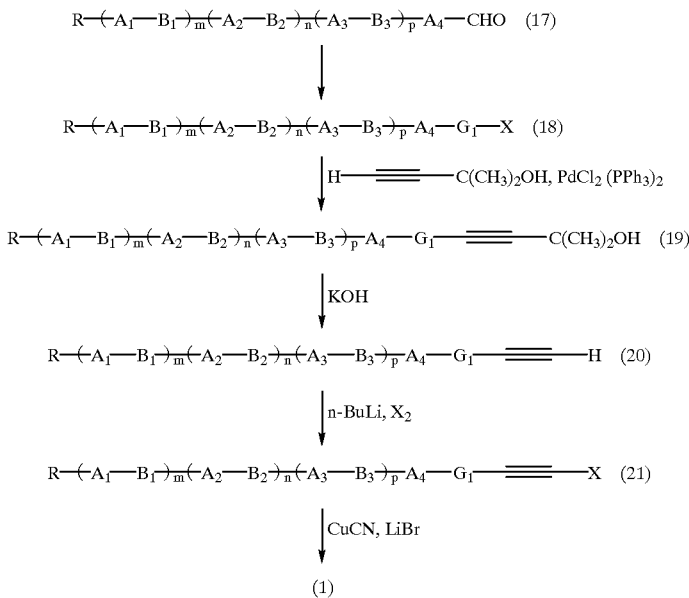

wherein R, $A_1$, $A_2$, $A_3$, $A_4$, $B_1$, $B_2$, $B_3$, G, m, n, and p have the same meaning as described above, G represents the group expressed the formula (3) or (4), and X represents a halogen atom.

Production of the compounds expressed by the general formula (1) wherein G represents the group expressed by the formula (3) or (4), and $A_4$ represents 1,4-phenylene in which hydrogen atom on the ring may be replaced by fluorine atom, or pyrimidine-2,5-diyl group:

A compound corresponding to the compound (20) described above can readily be obtained by performing a A compound of the present invention expressed by the general formula (1) can be obtained by reacting a known ethynylene derivative expressed by the general formula (23) with 1,2-dihalogenoethylene in a dipolar aprotic solvent or basic solvent in the presence of a transition metal catalyst (for example, dichlorobistriphenylphosphine palladium) to convert into a vinyl halide derivative expressed by the general formula (24), and then reacting it with a metal cyanide such as copper cyanide in a suitable polar solvent such as N-methylpyrrolidone (NMP).

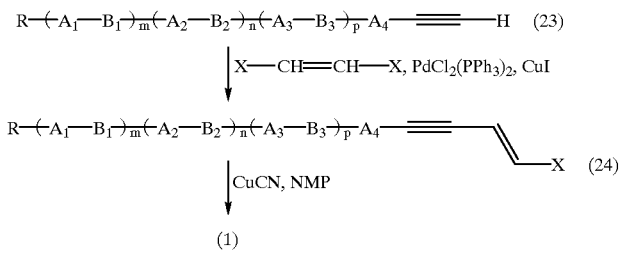

wherein R, $A_1$, $A_2$, $A_3$, $A_4$, $B_1$, $B_2$, $B_3$, G, m, n, and p have the same meaning as described above.

BEST MODE FOR CARRYING OUT THE INVENTION

Now the present invention will be described in more detail with reference to Examples. However, it should be understood that the scope of the present invention is by no means restricted by such specific Examples.

In each of the Examples, C indicate crystal, N: nematic phase, S: smectic phase, and I: isotropic liquid phase, and the unit of all phase transition temperatures is ° C.

EXAMPLE 1

Preparation of trans-4-(trans-4-pentylcyclohexyl)-1-(4-cyano-1-E-butene-3-yne-1-yl)cyclohexane (Compound expressed by the general formula (1) wherein R is pentyl group, m=n=0, p=1, both $A_3$ and $A_4$ are 1,4-cyclohexylene group, $B_3$ is a covalent bond, and G is the group expressed by the formula (3), Compound No. 34)

To a mixture of trans-4-(trans-4-pentylcyclohexyl)-1-(2-E-bromovinyl)cyclohexane (66 mmol), 2-methyl-3-butyne-2-ol (132 mmol), dichlorobistriphenylphosphine palladium (2.0 mmol), and copper iodide (7.4 mmol) was added by drops pyrrolidine, and stirred at room temperature under argon gas atmosphere overnight.

Aqueous ammonium chloride solution was added to the reaction solution, and extracted with toluene twice. The organic layer thus obtained was washed with an aqueous sodium chloride solution and dried over anhydrous magnesium sulfate. After filtration, the solvent was distilled off under a reduced pressure. The residue was purified by column chromatography (silica gel/toluene:ethyl acetate= 10:1) to obtain colorless crystals of trans-4-(trans-4-pentylcyclohexyl)-1-(5-hydroxy-5,5-dimethyl-1-E-pentene-3-yne-1-yl)cyclohexane. (Yield 92%)

This compound (58 mmol) and powdered potassium hydroxide (0.36 mmol) were refluxed in toluene for 2 hours. After it was cooled, 3N hydrochloric acid was added thereto until pH became 1, and then the organic layer was isolated. The water layer was further extracted with toluene, combined with the organic layer mentioned above, and then washed with a saturated aqueous sodium bicarbonate solution. After the layer was dried over anhydrous magnesium sulfate, it was subjected to filtration, and the solvent was distilled off under a reduced pressure. The residue was purified by column chromatography (silica gel/heptane) and recrystallization (ethanol) to obtain colorless crystals of trans-4-(trans-4-pentylcyclohexyl)-1-(1-E-butene-3-yne-1-yl)cyclohexane. (Yield 54%).

To a solution of this compound (34 mmol) in THF was added a solution of n-butyl lithium (38 mmol) in THF at −60° C., and then stirred for 1 hour. Subsequently, a solution of iodine (38 mmol) in THF was added thereto at a temperature lower than −30° C., and then allowed to stand until the temperature of the reaction mixture became 0° C. After an aqueous ammonium chloride solution was added to the reaction solution, and extracted with toluene twice, the organic layer was washed with an aqueous sodium thiosulfate solution and with an aqueous sodium chloride solution. The organic layer was dried over anhydrous magnesium sulfate. After the layer was subjected to filtration, the solvent was distilled off under a reduced pressure to obtain trans-4-(trans-4-pentylcyclohexyl) 1-(4-iodo-1-E-butene-3-yne-1-yl)cyclohexane. (Yield 92%). This unpurified compound (31 mmol), copper cyanide (39 mmol), and lithium bromide (11 mmol) were refluxed in THF for 6 hours. After it was cooled, the reaction mixture was poured into 10% aqueous iron (II) chloride solution and extracted with toluene twice. After the organic layer was washed with an aqueous sodium chloride solution, dried over anhydrous magnesium sulfate, and then subjected to filtration, the solvent was distilled off under a reduced pressure. The residue was purified by column chromatography (silica gel/heptane) and recrystallization (heptane) to obtain colorless crystals of the objective trans-4-(trans-4-pentylcyclohexyl)-1-(4-cyano-1-E-butene-3-yne-1-yl)cyclohexane.

(Yield 57%); MS; m/e=311 (M+); Phase transition points C. 42.8 N. 212 (dec. >170).I; Data of each spectrum of this compound and that of each stage well supported their structure.

EXAMPLE 2

Preparation of 4-(trans-4-propylcyclohexyl)-1-(4-cyano-1,3-butadiyne-1-yl)benzene (Compound expressed by the general formula (1) wherein R is propyl group, m=n=0, p=1, $A_3$ is 1,4-cyclohexylene group, $A_4$ is 1,4-phenylene group, $B_3$ is a covalent bond, G is the group expressed by the formula (4), Compound No. 62)

To a mixture of dichlorobistriphenylphosphine palladium (4.2 mmol) and copper iodide (0.64 mmol) was added diethylamine, and stirred at room temperature under argon gas atmosphere for 30 minutes. Then, 4-(trans-4-propylcyclohexyl)-1-(2-iodoethynyl)benzene (0.12 mol) was added thereto, and further stirred at room temperature for 15 minutes. To this reaction mixture was added (trimethylsilyl)acetylene (0.14 mol), and stirred at room temperature overnight. After completion of the reaction, water was added thereto and extracted with toluene twice. The organic layer thus obtained was washed with water, and then dried over anhydrous magnesium sulfate. After it was subjected to filtration, the solvent was distilled off under a reduced pressure. The residue was purified by column chromatography (silica gel/heptane) and recrystallization (ethanol) to obtain colorless crystals of 4-(trans-4-propylcyclohexyl)-1-(4-trimethylsilyl-1,3-butadiyne-1-yl) benzene. (Yield 24%).

To this compound (26 mmol) was added potassium fluoride (59 mol), and then stirred in DMF at room temperature for 4 hours. After it was cooled, water was added thereto, and extracted with heptane twice, the organic layer thus obtained was dried over anhydrous magnesium sulfate. After it was subjected to filtration, the solvent was distilled off under a reduced pressure to obtain 4-(trans-4-propylcyclohexyl)-1-(1,3-butadiyne-1-yl)benzene. (Yield 67%).

To a solution of this unpurified compound (16 mmol) in THF was added a solution of n-butyl lithium (18 mmol) in THF at −60° C., and further stirred for 1 hour. Subsequently, a solution of iodine (18 mmol) in THF was added thereto at a temperature lower than −30° C., and the reaction mixture was allowed to stand until its temperature became 0° C. After an aqueous ammonium chloride solution was added to the reaction solution and extracted with toluene twice, the organic layer thus obtained was washed with an aqueous sodium thiosulfate solution and with an aqueous sodium chloride solution, and then dried over anhydrous magnesium sulfate. After it was subjected to filtration, the solvent was distilled off under a reduced pressure to obtain 4-(trans-4-propylcyclohexyl)-1-(4-iodo-1,3-butadiyne-1-yl)benzene. (Yield 100%).

This unpurified compound (16 mmol), copper cyanide (20 mmol), and lithium bromide (5.9 mmol) were refluxed in THF for 5 hours. After it was cooled, the reaction mixture was poured into 10% aqueous iron (II) chloride solution, and the solution was extracted with toluene twice. After the organic layer thus obtained was washed with an aqueous sodium chloride solution, it was dried over anhydrous magnesium sulfate. After it was subjected to filtration, the solvent was distilled off under a reduced pressure. The residue was purified by column chromatography (silica gel/heptane→heptane:toluene=5:1) and recrystallization (heptane) to obtain pale yellow crystals of 4-(trans-4-propylcyclohexyl)-1-(4-cyano-1,3-butadiyne-1-yl)benzene. (Yield 78%).

MS; m/e=275 (M+); Phase transition points C. 71.3.N.dec.>150; Data of each spectrum of this compound and that of each stage well supported their structure.

EXAMPLE 3

According to the method of Example 1, trans-4-(trans-4-propylcyclohexyl)-1-(4-cyano-1,3-butadiyne-1-yl)cyclohexane (Compound No. 56) was synthesized.

EXAMPLE 4

According to the method of Example 2,4-(trans-4-ethenylcyclohexyl)-1-(4-cyano-1,3-butadiyne-1-yl)benzene (Compound No. 64) was synthesized.

EXAMPLE 5

According to the method of Example 1, trans-4-(trans-4-(trans-4-propylcyclohexyl)cyclohexyl)-1-(4-cyano-1-E-butene-3-yne-1-yl)cyclohexane (Compound No. 84) was synthesized.

EXAMPLE 6

According to the method of Example 1, trans-4-(trans-4-(4-fluorophenyl)cyclohexyl)-1-(4-cyano-1-E-butene-3-yne-1-yl)cyclohexane (Compound No. 90) was synthesized.

EXAMPLE 7

According to the method of Example 2, 4-(trans-4(2-E-(trans-4-propylcyclohexyl)ethenylene-1-yl)cyclohexyl)-1-(4-cyano-1,3-butadiyne-1-yl)benzene (Compound No. 151) was synthesized.

EXAMPLE 8

According to the method of Example 2, 4-(trans-4-propylcyclohexyl)-4'-(4-cyano-1,3-butadiyne-1-yl)tolan (Compound No. 174) was synthesized.

EXAMPLE 9

According to the method of Example 2, 4-(4-(trans-4-propylcyclohexyl)phenethyl)-4'-(4-cyano-1,3-butadiyne-1-yl)biphenyl (Compound No. 198) was synthesized.

According to Examples 1 to 9 described above, the following compounds of No. 1 through No. 244 can be prepared.

In the following, compounds obtained by one of Examples 1 to 9 are described again.

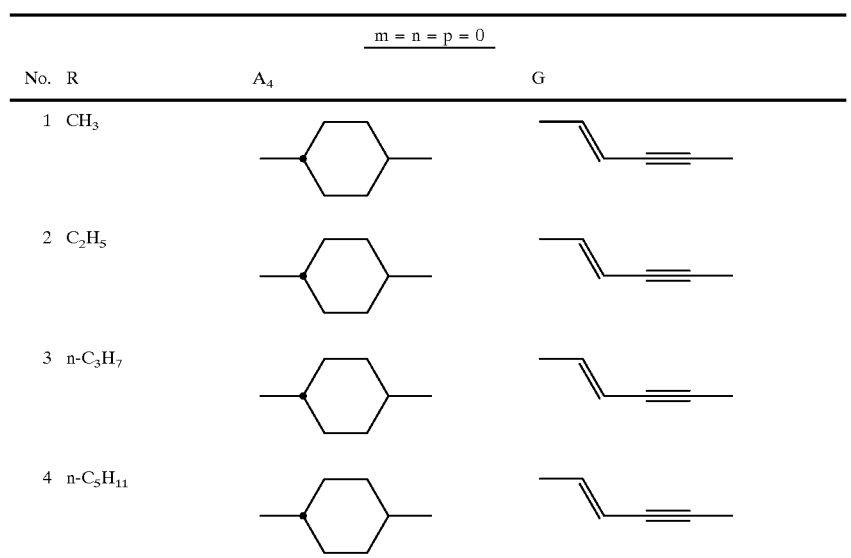

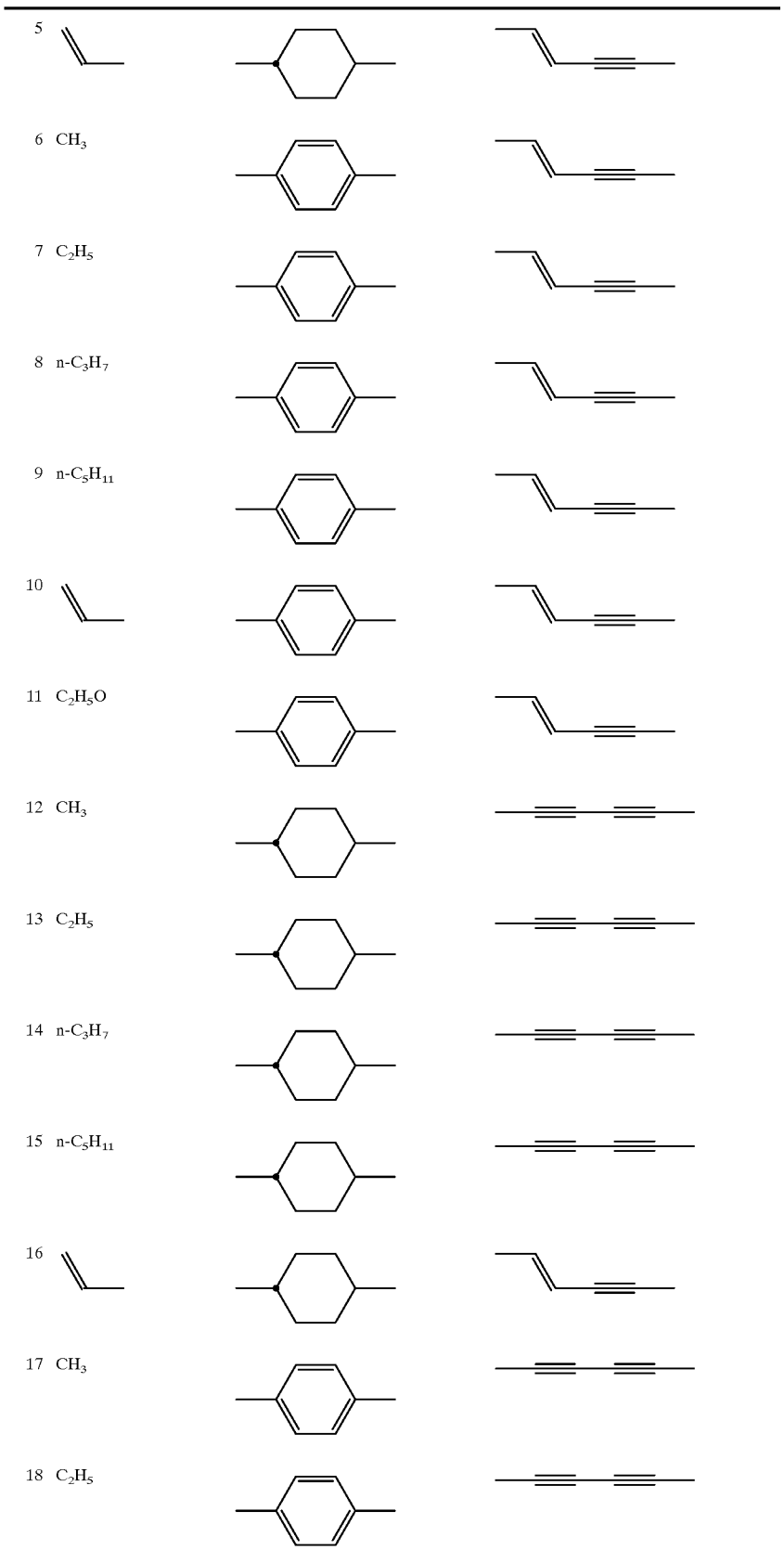

-continued

| # | R | Ring | Chain |
|---|---|---|---|
| 19 | n-C$_3$H$_7$ | 1,4-phenylene | -C≡C-C≡C- |
| 20 | n-C$_5$H$_{11}$ | 1,4-phenylene | -C≡C-C≡C- |
| 21 | CH$_2$=CH-CH$_2$- | 1,4-phenylene | -C≡C-C≡C- |
| 22 | C$_2$H$_5$O | trans-1,4-cyclohexylene | -C≡C-C≡C- |
| 23 | n-C$_3$H$_7$ | 3,5-difluoro-1,4-phenylene | -CH=CH-C≡C- |
| 24 | n-C$_5$H$_{11}$ | 3,5-difluoro-1,4-phenylene | -CH=CH-C≡C- |
| 25 | n-C$_3$H$_7$ | 3,5-difluoro-1,4-phenylene | -C≡C-C≡C- |
| 26 | n-C$_5$H$_{11}$ | 3,5-difluoro-1,4-phenylene | -C≡C-C≡C- |
| 27 | n-C$_3$H$_7$ | pyrimidine-2,5-diyl | -CH=CH-C≡C- |
| 28 | n-C$_5$H$_{11}$ | pyrimidine-2,5-diyl | -CH=CH-C≡C- |
| 29 | n-C$_3$H$_7$ | pyrimidine-2,5-diyl | -C≡C-C≡C- |

-continued
| No. | R | | | | G |
|---|---|---|---|---|---|
| 30 | n-C$_5$H$_{11}$ | 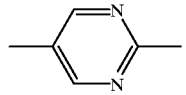 | | |  |
$\underline{m = n = 0, p = 1}$
| No. | R | A$_3$ | B$_3$ | A$_4$ | G |
|---|---|---|---|---|---|
| 31 | CH$_3$ |  | — | 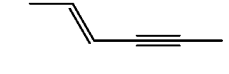 | 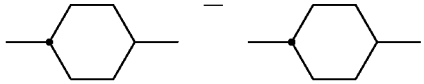 |
| 32 | C$_2$H$_5$ | 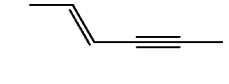 | — |  | 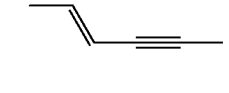 |
| 33 | n-C$_3$H$_7$ |  | — | 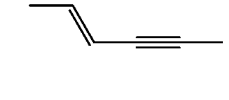 |  |
| 34 | n-C$_5$H$_{11}$ | 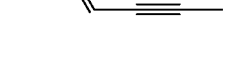 | — |  | 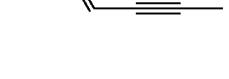 |
| 35 | CH$_3$ |  | — |  |  |
| 36 | C$_2$H$_5$ |  | — |  |  |
| 37 | n-C$_3$H$_7$ | 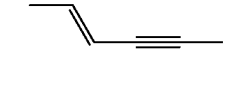 | — |  | 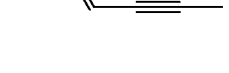 |
| 38 | n-C$_5$H$_{11}$ |  | — | | |
| 39 | | | — | | |
| 40 | n-C$_3$H$_7$ | | — | | |
| 41 | n-C$_5$H$_{11}$ | | — | | |

-continued
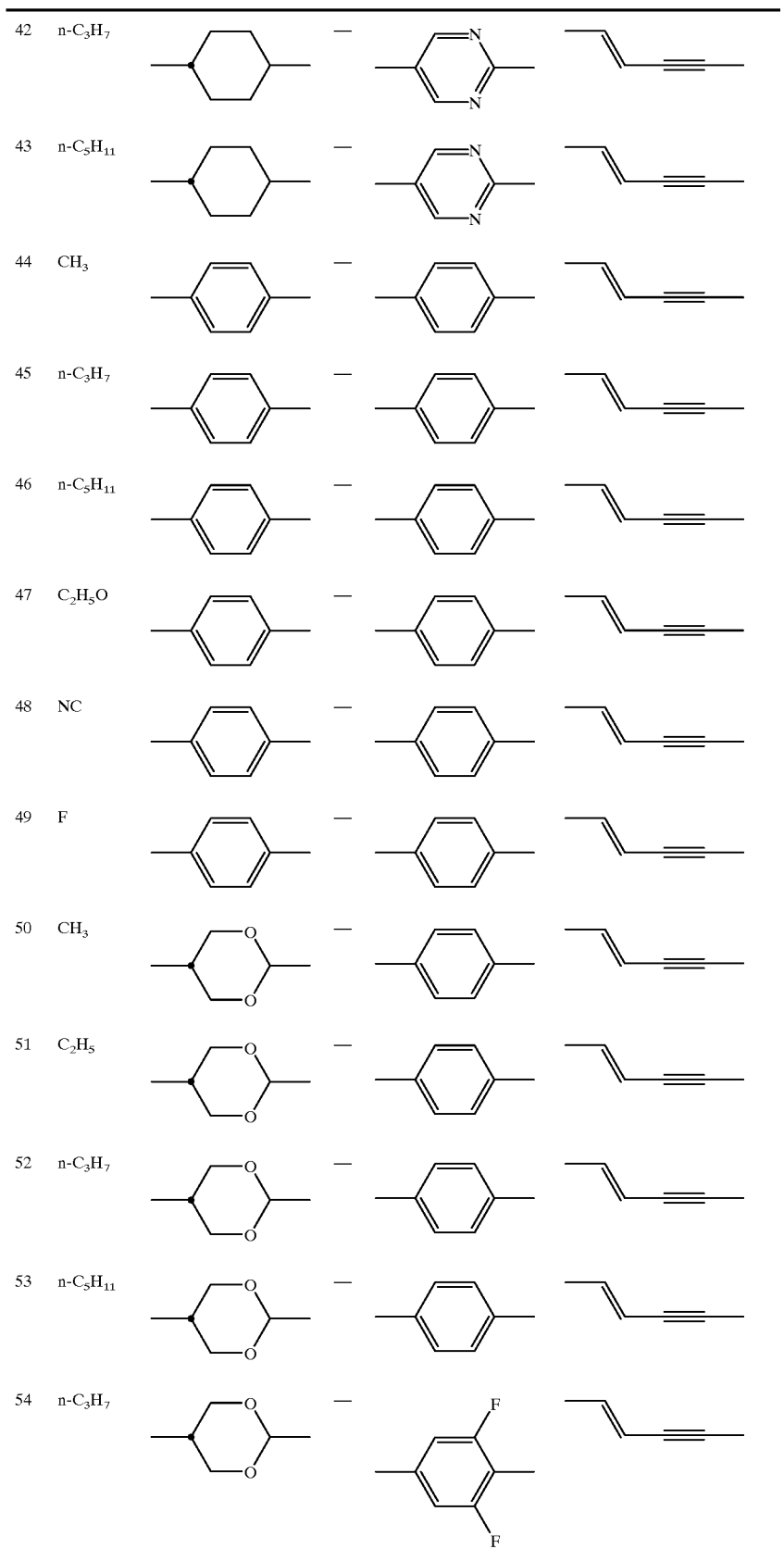

-continued
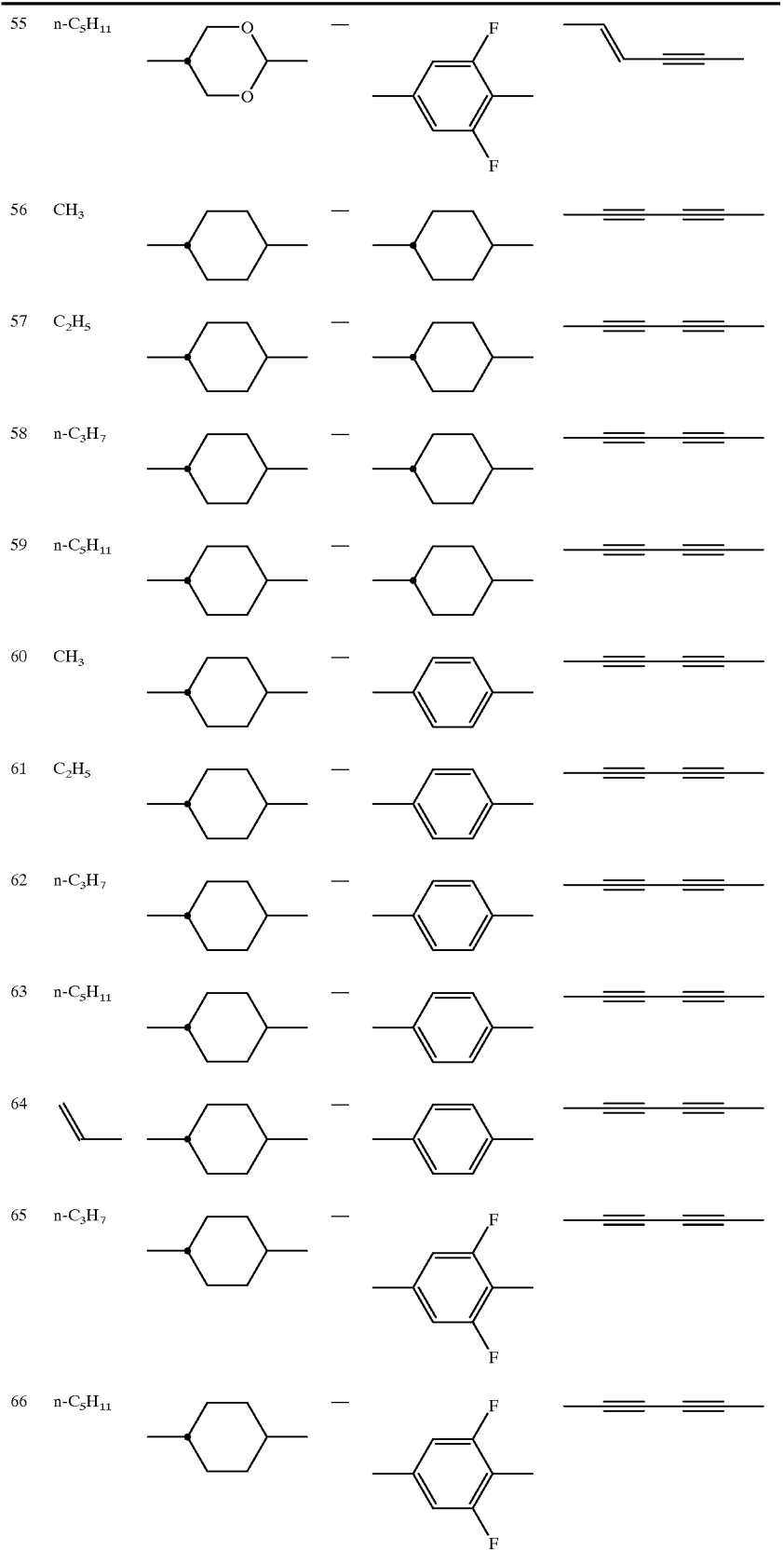

-continued
| | | | | | |
|---|---|---|---|---|---|
| 67 | n-C$_3$H$_7$ | 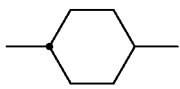 | — | 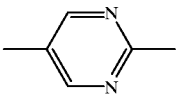 | 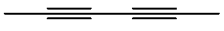 |
| 68 | n-C$_5$H$_{11}$ |  | — | 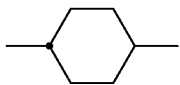 | 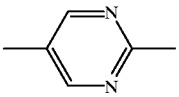 |
| 69 | CH$_3$ |  | — |  |  |
| 70 | n-C$_3$H$_7$ |  | — | 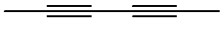 |  |
| 71 | n-C$_5$H$_{11}$ |  | — |  |  |
| 72 | C$_2$H$_5$O |  | — |  |  |
| 73 | NC |  | — |  |  |
| 74 | F |  | — |  |  |
| 75 | CH$_3$ | 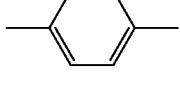 | — | 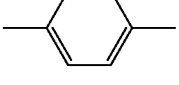 |  |
| 76 | CH$_3$ |  | — |  |  |
| 77 | C$_2$H$_5$ |  | — |  | 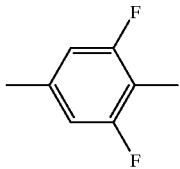 |
| 78 | n-C$_3$H$_7$ | 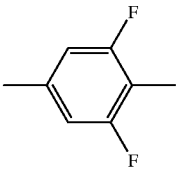 | — |  |  |
| 79 | n-C$_5$H$_{11}$ | 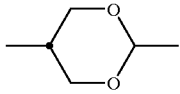 | — |  |  |

-continued

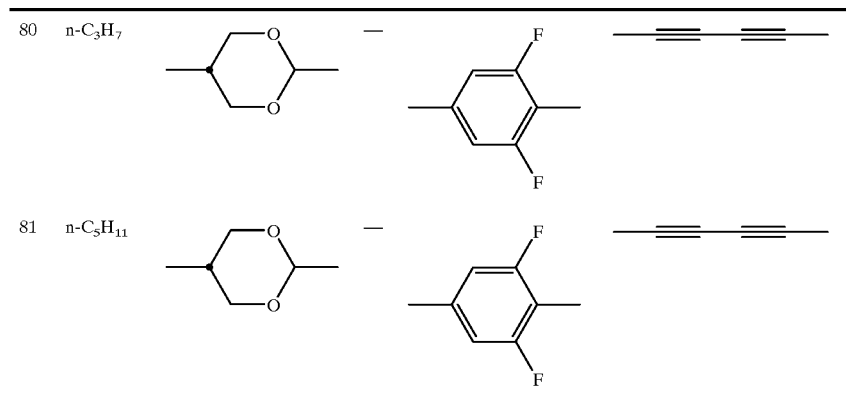

| No. | R | A$_2$ | B$_2$ | A$_3$ |
|---|---|---|---|---|
| 80 | n-C$_3$H$_7$ | 1,3-dioxane | — | 3,5-difluorophenyl | —C≡C—C≡C— |
| 81 | n-C$_5$H$_{11}$ | 1,3-dioxane | — | 3,5-difluorophenyl | —C≡C—C≡C— | m = 0, n = p = 1

| No. | R | A$_2$ | B$_2$ | A$_3$ |
|---|---|---|---|---|
| 82 | CH$_3$ | cyclohexyl | — | cyclohexyl |
| 83 | C$_2$H$_5$ | cyclohexyl | — | cyclohexyl |
| 84 | n-C$_3$H$_7$ | cyclohexyl | — | cyclohexyl |
| 85 | n-C$_5$H$_{11}$ | cyclohexyl | — | cyclohexyl |
| 86 | CH$_3$ | phenyl | — | cyclohexyl |
| 87 | n-C$_3$H$_7$ | phenyl | — | cyclohexyl |
| 88 | C$_2$H$_5$O | phenyl | — | cyclohexyl |
| 89 | NC | phenyl | — | cyclohexyl |
| 90 | F | phenyl | — | cyclohexyl |
| 91 | CH$_3$ | cyclohexyl | — | cyclohexyl |

-continued
| | | | | | |
|---|---|---|---|---|---|
| 92 | $C_2H_5$ | 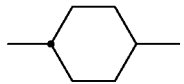 | — | 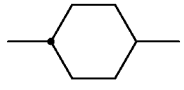 | |
| 93 | n-$C_3H_7$ | 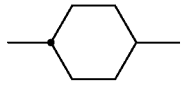 | — | 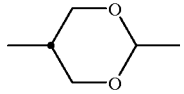 | |
| 94 | n-$C_5H_{11}$ | 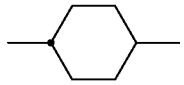 | — | 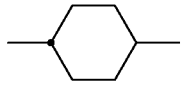 | |
| 95 | n-$C_3H_7$ | 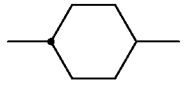 | — | 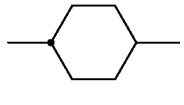 | |
| 96 | n-$C_3H_7$ | 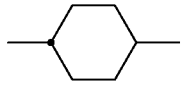 | — | 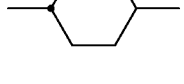 | |
| 97 | $CH_3$ | 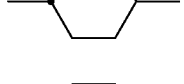 | — | 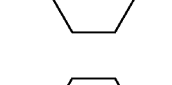 | |
| 98 | n-$C_3H_7$ | 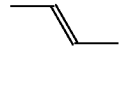 | — | 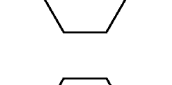 | |
| 99 | $CH_3$ | | — | | |
| 100 | n-$C_3H_7$ | | — | | |
| 101 | $CH_3$ | | — | | |
| 102 | n-$C_3H_7$ | | — | | |
| 103 | $CH_3$ | |  | | |
| 104 | $C_2H_5$ | | 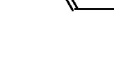 | | |
| 105 | n-$C_3H_7$ | | 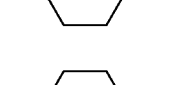 | | |

-continued
| | | | | |
|---|---|---|---|---|
| 106 | n-C$_5$H$_{11}$ |  |  | 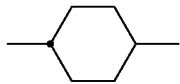 |
| 107 | n-C$_3$H$_7$ |  |  | 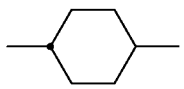 |
| 108 | CH$_3$ |  | —CO$_2$— | 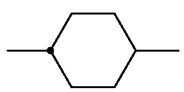 |
| 109 | C$_2$H$_5$ |  | —CO$_2$— |  |
| 110 | n-C$_3$H$_7$ |  | —CO$_2$— | 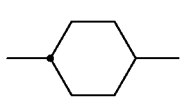 |
| 111 | n-C$_5$H$_{11}$ | 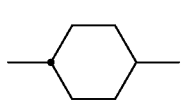 | —CO$_2$— | 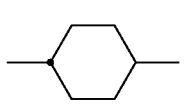 |
| 112 | n-C$_3$H$_7$ | 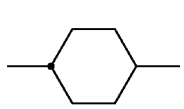 | —CO$_2$— | 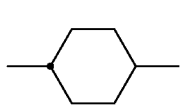 |
| 113 | CH$_3$ | 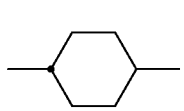 | — | 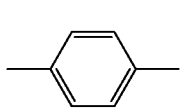 |
| 114 | C$_2$H$_5$ | 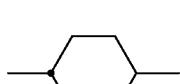 | — | 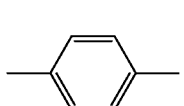 |
| 115 | n-C$_3$H$_7$ | 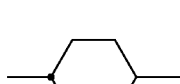 | — | 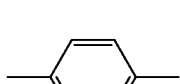 |
| 116 | n-C$_5$H$_{11}$ |  | — | 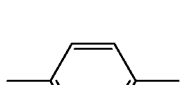 |
| 117 | n-C$_3$H$_7$ | 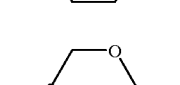 | — | 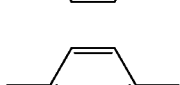 |
| 118 | n-C$_3$H$_7$ | 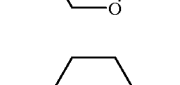 | — | 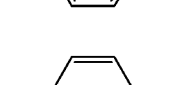 |
| 119 | CH$_3$ | 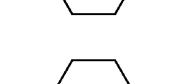 | — | 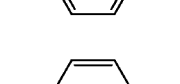 |

-continued
| | | | | |
|---|---|---|---|---|
| 120 | C₂H₅ | 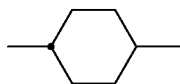 | — |  |
| 121 | n-C₃H₇ |  | — |  |
| 122 | n-C₅H₁₁ |  | — |  |
| 123 | n-C₃H₇ | 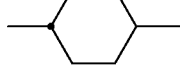 | — | 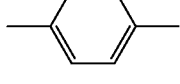 |
| 124 | n-C₃H₇ | 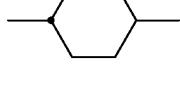 | — | 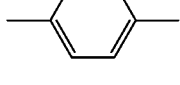 |
| 125 | n-C₃H₇ | 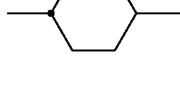 | — | 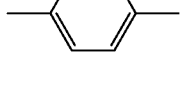 |
| 126 | CH₃ | 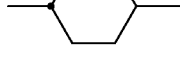 | — | 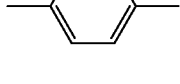 |
| 127 | n-C₃H₇ | 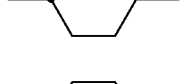 | — | 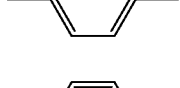 |
| 128 | n-C₅H₁₁ | 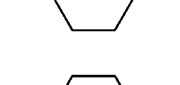 | — | 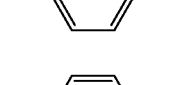 |
| 129 | n-C₃H₇ | 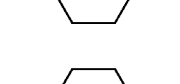 | — | 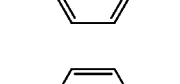 |
| 130 |  | 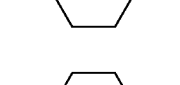 | — | 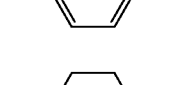 |
| 131 | CH₃ | 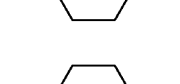 | — | 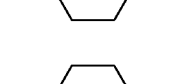 |
| 132 | C₂H₅ | 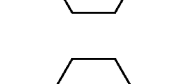 | — | 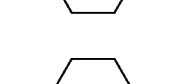 |
| 133 | n-C₃H₇ | 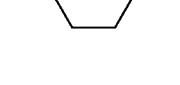 | — | 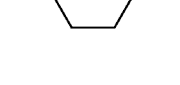 |

-continued

| # | R | Ring A | | Ring B |
|---|---|---|---|---|
| 134 | n-C$_5$H$_{11}$ | cyclohexyl | — | cyclohexyl |
| 135 | n-C$_3$H$_7$ | phenyl | — | cyclohexyl |
| 136 | NC | phenyl | — | cyclohexyl |
| 137 | CH$_3$ | cyclohexyl | — | cyclohexyl |
| 138 | C$_2$H$_5$ | cyclohexyl | — | cyclohexyl |
| 139 | n-C$_3$H$_7$ | cyclohexyl | — | cyclohexyl |
| 140 | n-C$_5$H$_{11}$ | cyclohexyl | — | cyclohexyl |
| 141 | n-C$_3$H$_7$ | cyclohexyl | — | cyclohexyl |
| 142 | n-C$_3$H$_7$ | 1,3-dioxane | — | cyclohexyl |
| 143 | CH$_3$ | cyclohexyl | — | cyclohexyl |
| 144 | n-C$_3$H$_7$ | cyclohexyl | — | cyclohexyl |
| 145 | CH$_3$ | cyclohexyl | — | cyclohexyl |
| 146 | n-C$_3$H$_7$ | cyclohexyl | — | cyclohexyl |
| 147 | CH$_3$ | cyclohexyl | — | phenyl |

-continued
| | | | | |
|---|---|---|---|---|
| 148 | n-$C_3H_7$ | 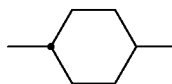 | — |  |
| 149 | $CH_3$ | 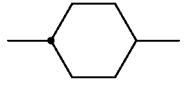 |  |  |
| 150 | $C_2H_5$ | 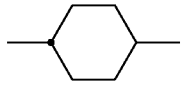 |  |  |
| 151 | n-$C_3H_7$ | 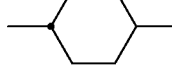 |  | 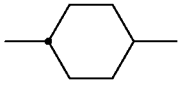 |
| 152 | n-$C_5H_{11}$ | 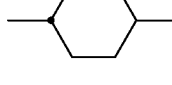 |  | 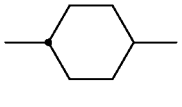 |
| 153 | n-$C_3H_7$ | 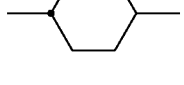 |  | 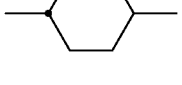 |
| 154 | $CH_3$ | 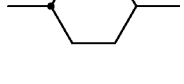 | —$CO_2$— | 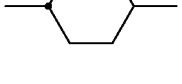 |
| 155 | $C_2H_5$ | 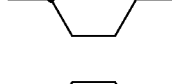 | —$CO_2$— | 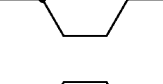 |
| 156 | n-$C_3H_7$ | 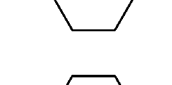 | —$CO_2$— | 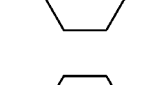 |
| 157 | n-$C_5H_{11}$ | 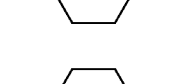 | —$CO_2$— | 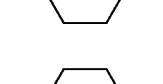 |
| 158 | n-$C_3H_7$ | 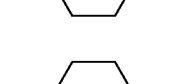 | —$CO_2$— | 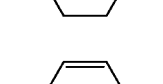 |
| 159 | $CH_3$ | 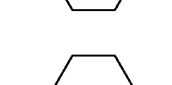 | — |  |
| 160 | $C_2H_5$ |  | — | 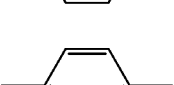 |
| 161 | n-$C_3H_7$ |  | — |  |

-continued
| 162 | n-C$_3$H$_7$ | 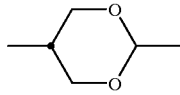 | — | 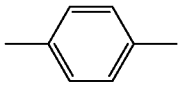 |
| 163 | n-C$_5$H$_{11}$ | 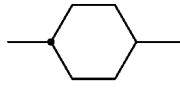 | — | 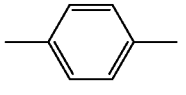 |
| 164 | n-C$_3$H$_7$ | 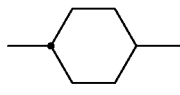 | — | 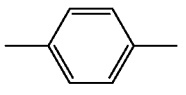 |
| 165 | CH$_3$ | 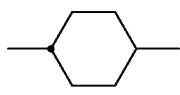 | — | 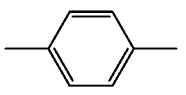 |
| 166 | C$_2$H$_5$ | 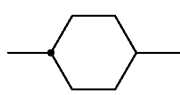 | — | 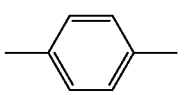 |
| 167 | n-C$_3$H$_7$ | 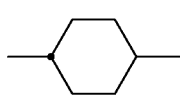 | — | 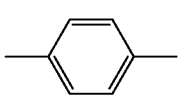 |
| 168 | n-C$_5$H$_{11}$ | 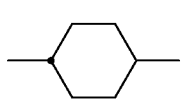 | — | 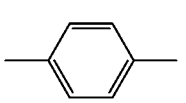 |
| 169 | n-C$_3$H$_7$ | 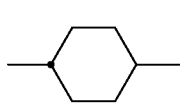 | — | 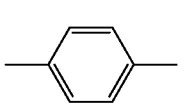 |
| 170 | n-C$_3$H$_7$ | 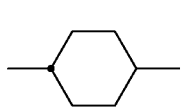 | — | 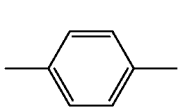 |
| 171 | n-C$_3$H$_7$ | 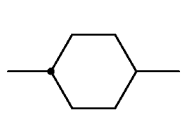 | — | 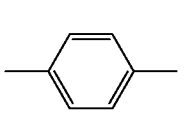 |
| 172 | CH$_3$ | 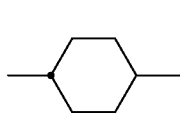 | — | 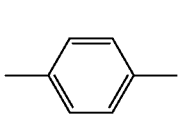 |
| 173 | C$_2$H$_5$ | 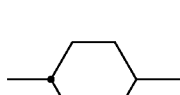 | — | 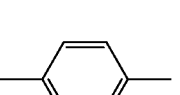 |
| 174 | n-C$_3$H$_7$ | 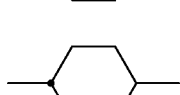 | — | 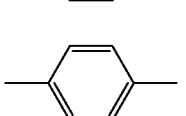 |
| 175 | n-C$_5$H$_{11}$ | 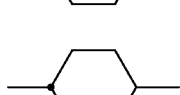 | — | 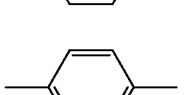 |

-continued
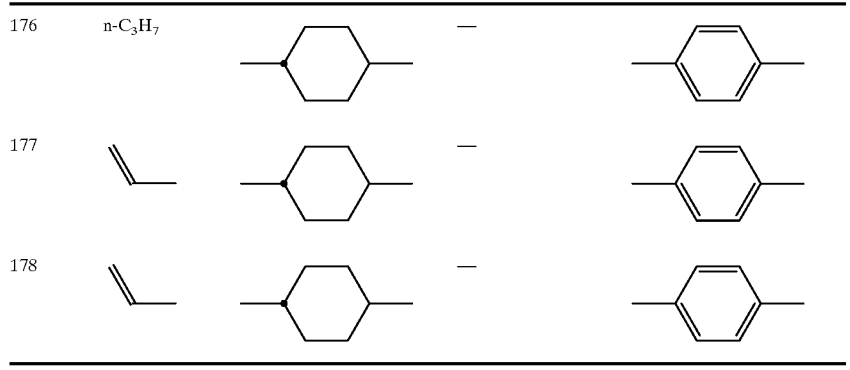
$m = 0, n = p = 1$
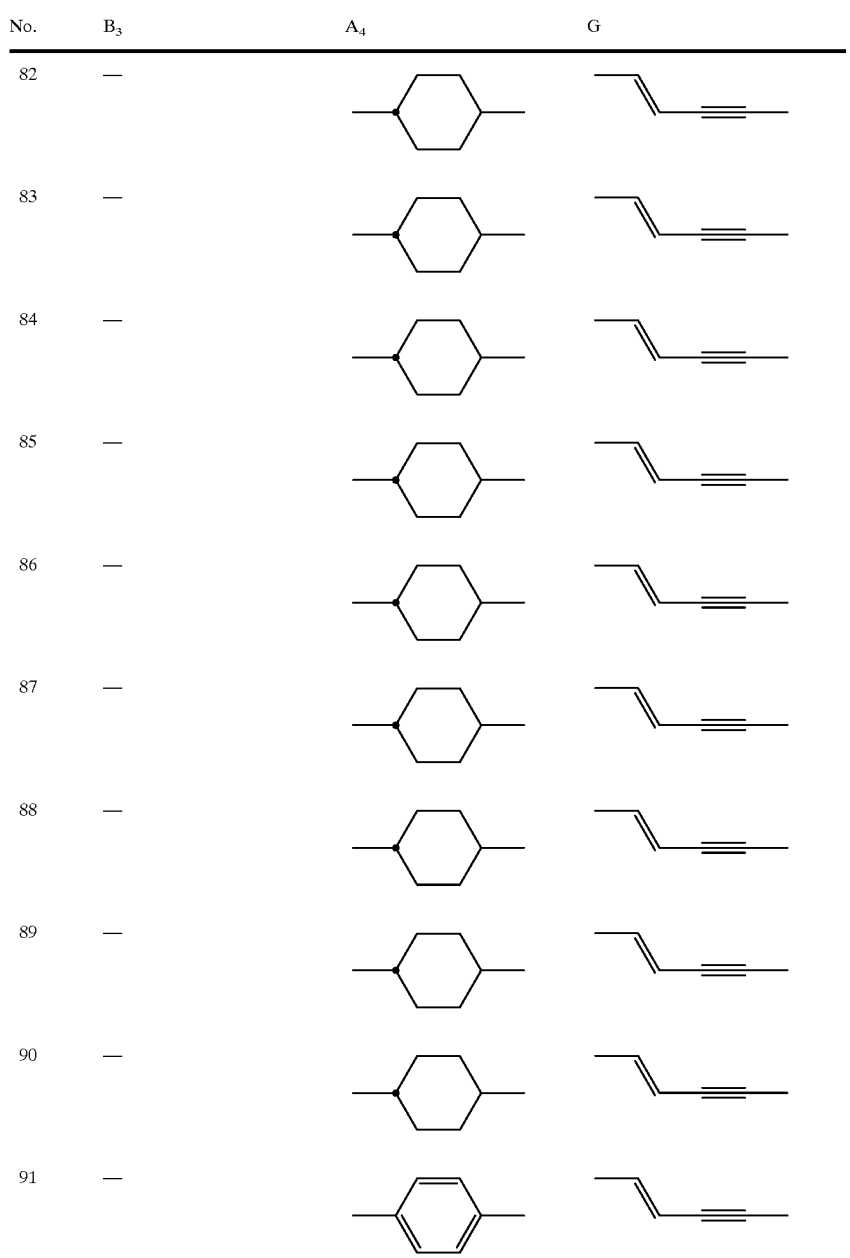

-continued
| | | | |
|---|---|---|---|
| 92 | — | 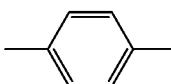 | 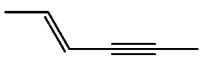 |
| 93 | — | 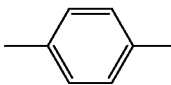 | 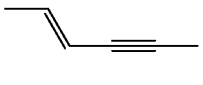 |
| 94 | — | 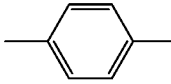 | 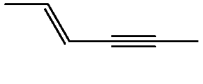 |
| 95 | — | 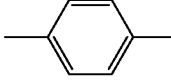 | 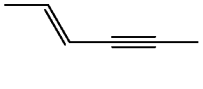 |
| 96 | — | 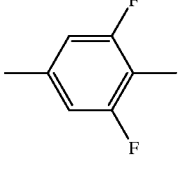 | 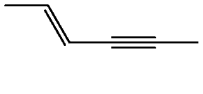 |
| 97 | $OCH_2$ | 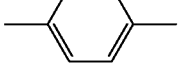 | 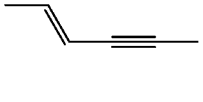 |
| 98 | $OCH_2$ | 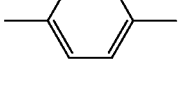 | 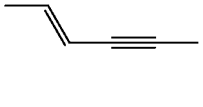 |
| 99 | $CH_2O$ | 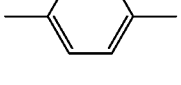 | 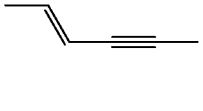 |
| 100 | $CH_2O$ | 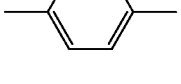 | 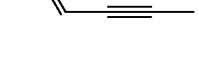 |
| 101 | 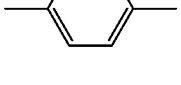 | 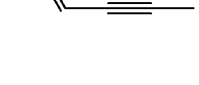 | 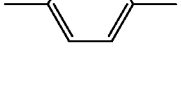 |
| 102 | 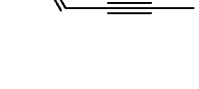 | 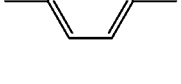 |  |
| 103 | — | 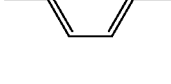 | |
| 104 | — | |  |

-continued

| | | | |
|---|---|---|---|
| 105 | — | phenylene | CH=CH-C≡C |
| 106 | — | phenylene | CH=CH-C≡C |
| 107 | — | 2,6-difluorophenylene | CH=CH-C≡C |
| 108 | — | phenylene | CH=CH-C≡C |
| 109 | — | phenylene | CH=CH-C≡C |
| 110 | — | phenylene | CH=CH-C≡C |
| 111 | — | phenylene | CH=CH-C≡C |
| 112 | — | 2,6-difluorophenylene | CH=CH-C≡C |
| 113 | — | phenylene | CH=CH-C≡C |
| 114 | — | phenylene | CH=CH-C≡C |
| 115 | — | phenylene | CH=CH-C≡C |
| 116 | — | phenylene | CH=CH-C≡C |
| 117 | — | phenylene | CH=CH-C≡C |

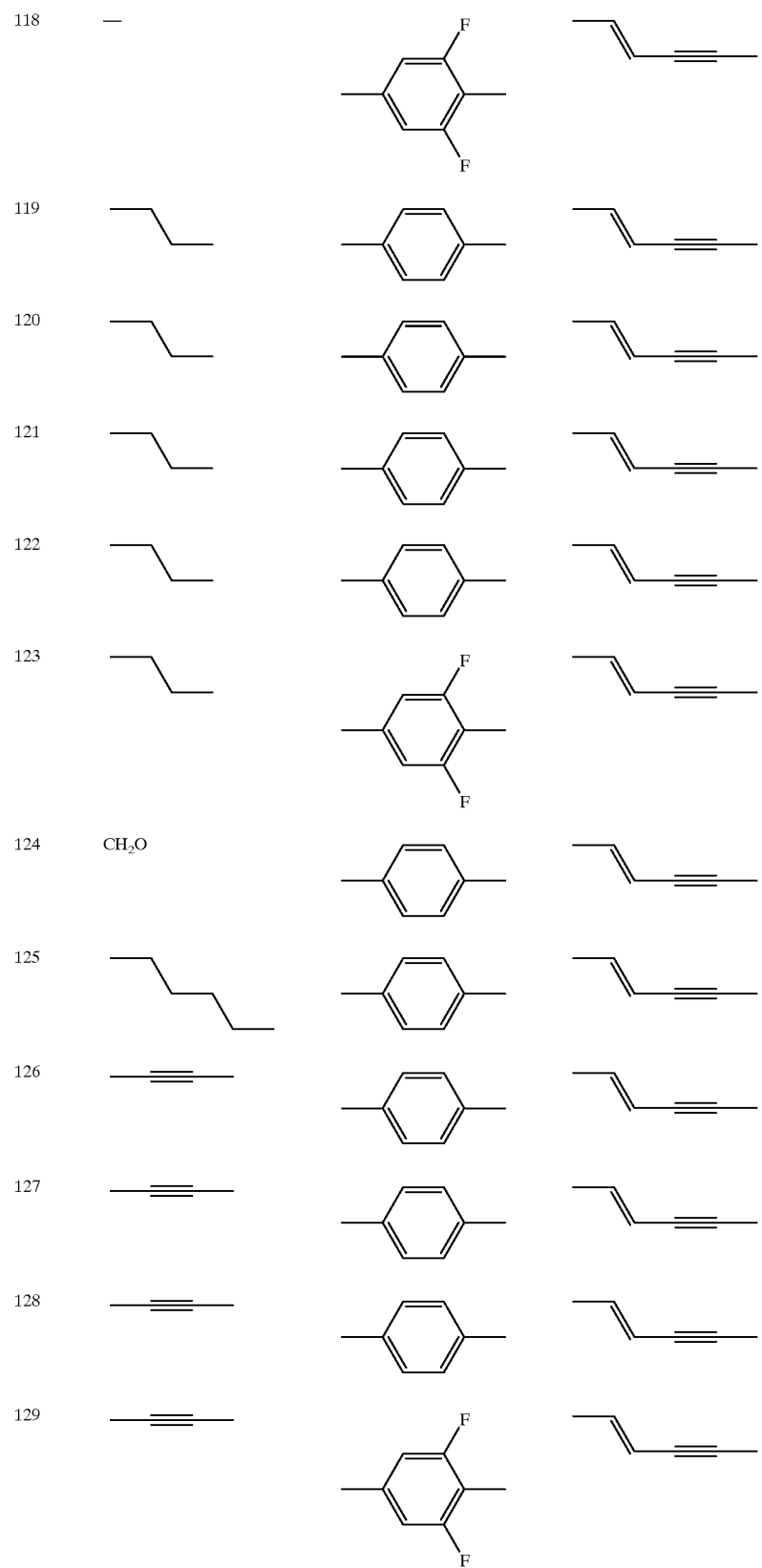

-continued
| | | | |
|---|---|---|---|
| 130 | — | 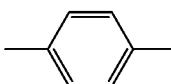 | 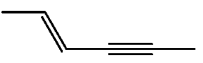 |
| 131 | — |  | 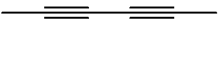 |
| 132 | — |  | 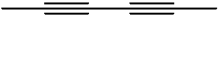 |
| 133 | — |  |  |
| 134 | — | 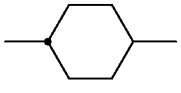 |  |
| 135 | — | 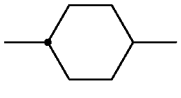 |  |
| 136 | — | 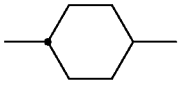 |  |
| 137 | — | 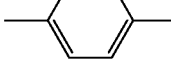 |  |
| 138 | — | 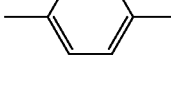 |  |
| 139 | — | 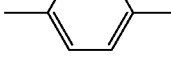 |  |
| 140 | — | 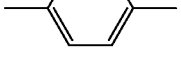 |  |
| 141 | — | 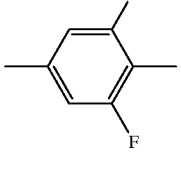 |  |
| 142 | — | 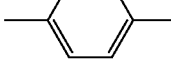 |  |

-continued
| 143 | OCH$_2$ | 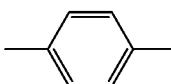 | 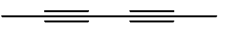 |
| --- | --- | --- | --- |
| 144 | OCH$_2$ | 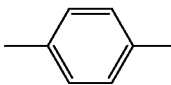 | 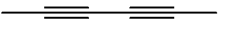 |
| 145 | CH$_2$O | 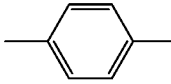 | 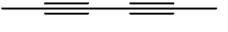 |
| 146 | CH$_2$O | 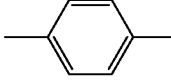 |  |
| 147 | 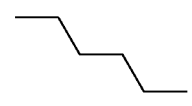 | 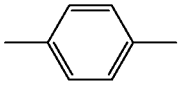 | 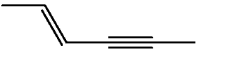 |
| 148 | 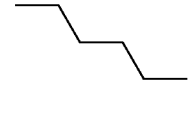 | 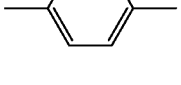 |  |
| 149 | — | 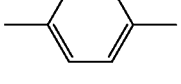 |  |
| 150 | — | 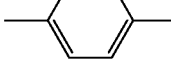 |  |
| 151 | — | 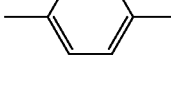 |  |
| 152 | — | 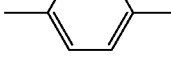 |  |
| 153 | — | 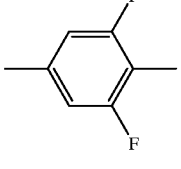 |  |
| 154 | — | 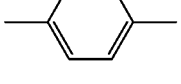 |  |
| 155 | — | 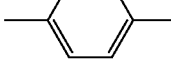 |  |

-continued

| | | | |
|---|---|---|---|
| 156 | — | ―⟨phenyl⟩― | ―≡―≡― |
| 157 | — | ―⟨phenyl⟩― | ―≡―≡― |
| 158 | — | ―⟨phenyl-2,3-F₂⟩― | ―≡―≡― |
| 159 | — | ―⟨phenyl⟩― | ―≡―≡― |
| 160 | — | ―⟨phenyl⟩― | ―≡―≡― |
| 161 | — | ―⟨phenyl⟩― | ―≡―≡― |
| 162 | — | ―⟨phenyl⟩― | ―≡―≡― |
| 163 | — | ―⟨phenyl⟩― | ―≡―≡― |
| 164 | — | ―⟨phenyl-2,3-F₂⟩― | ―≡―≡― |
| 165 | propyl | ―⟨phenyl⟩― | ―≡―≡― |
| 166 | propyl | ―⟨phenyl⟩― | ―≡―≡― |
| 167 | propyl | ―⟨phenyl⟩― | ―≡―≡― |
| 168 | propyl | ―⟨phenyl⟩― | ―≡―≡― |

-continued
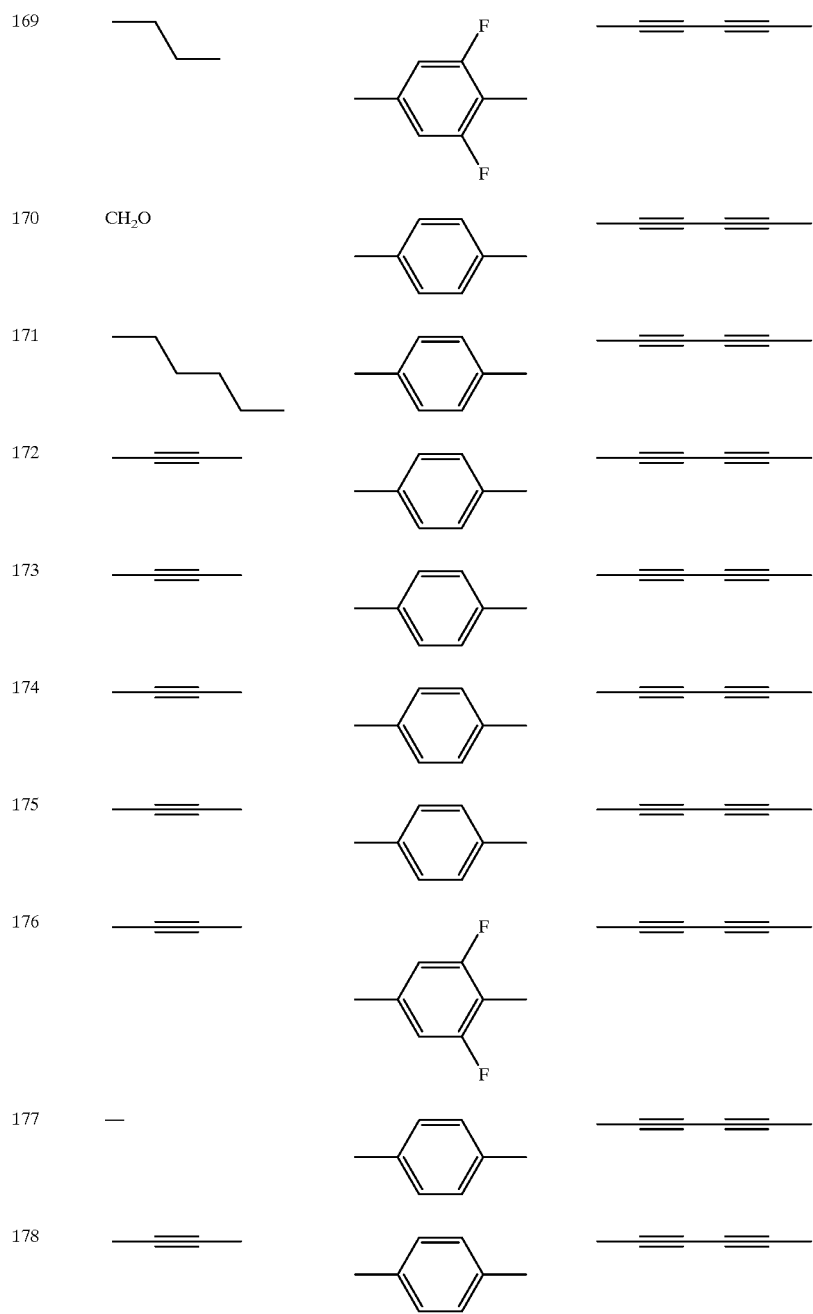
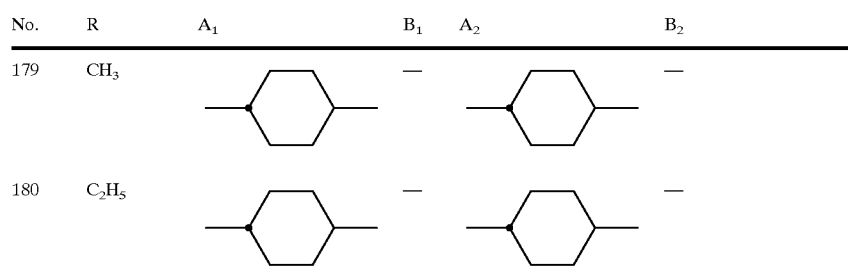

-continued
| | | | | | |
|---|---|---|---|---|---|
| 181 | n-C$_3$H$_7$ | 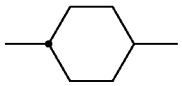 | — | 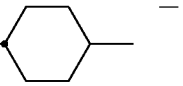 | — |
| 182 | n-C$_5$H$_{11}$ |  | — | 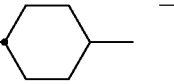 | — |
| 183 | n-C$_3$H$_7$ |  | — | 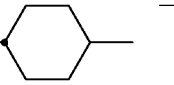 | — |
| 184 | CH$_3$ | 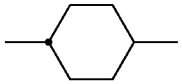 | — | 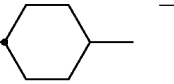 | — |
| 185 | C$_2$H$_5$ | 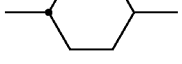 | — | 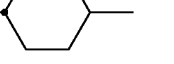 | — |
| 186 | n-C$_3$H$_7$ | 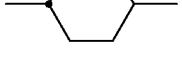 | — | 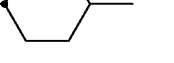 | — |
| 187 | n-C$_5$H$_{11}$ | 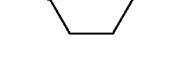 | — | 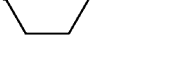 | — |
| 188 | n-C$_3$H$_7$ | 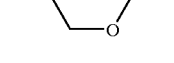 | — | 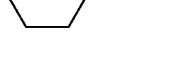 | — |
| 189 | 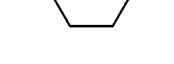 | 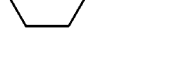 | — | 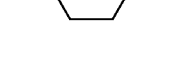 | — |
| 190 | CH$_3$ | 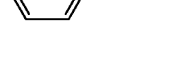 | — | 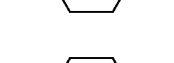 | — |
| 191 | C$_2$H$_5$ | 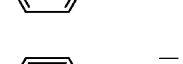 | — |  | — |
| 192 | n-C$_3$H$_7$ | 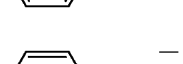 | — | 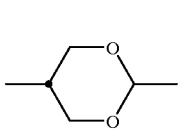 | — |
| 193 | n-C$_5$H$_{11}$ | 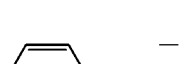 | — |  | — |
| 194 | n-C$_3$H$_7$ |  | — | | — |

-continued

| | | | | | |
|---|---|---|---|---|---|
| 195 | CH2=CH-CH2- | cyclohexyl | — | phenyl | — |
| 196 | CH3 | cyclohexyl | — | phenyl | n-propyl |
| 197 | C2H5 | cyclohexyl | — | phenyl | n-propyl |
| 198 | n-C3H7 | cyclohexyl | — | phenyl | n-propyl |
| 199 | n-C5H11 | cyclohexyl | — | phenyl | n-propyl |
| 200 | n-C3H7 | cyclohexyl | — | phenyl | n-propyl |
| 201 | n-C3H7 | 1,3-dioxane | — | phenyl | n-propyl |
| 202 | CH2=CH-CH2- | cyclohexyl | — | phenyl | n-propyl |
| 203 | CH3 | phenyl | — | phenyl | — |
| 204 | C2H5 | phenyl | — | phenyl | — |
| 205 | n-C3H7 | phenyl | — | phenyl | — |
| 206 | n-C3H7 | phenyl | — | phenyl | — |
| 207 | n-C5H11 | phenyl | — | phenyl | — |
| 208 | C2H5O | phenyl | — | phenyl | — |

-continued

| | | | | | |
|---|---|---|---|---|---|
| 209 | CH₂=CH–CH₂– | phenyl | — | phenyl | — |
| 210 | NC | phenyl | — | phenyl | — |
| 211 | F | phenyl | — | phenyl | — |
| 212 | CH₃ | cyclohexyl | — | cyclohexyl | — |
| 213 | C₂H₅ | cyclohexyl | — | cyclohexyl | — |
| 214 | n-C₃H₇ | cyclohexyl | — | cyclohexyl | — |
| 215 | n-C₅H₁₁ | cyclohexyl | — | cyclohexyl | — |
| 216 | n-C₃H₇ | dioxanyl | — | cyclohexyl | — |
| 217 | CH₃ | cyclohexyl | — | cyclohexyl | — |
| 218 | C₂H₅ | cyclohexyl | — | cyclohexyl | — |
| 219 | n-C₃H₇ | cyclohexyl | — | cyclohexyl | — |
| 220 | n-C₅H₁₁ | cyclohexyl | — | cyclohexyl | — |
| 221 | n-C₃H₇ | dioxanyl | — | cyclohexyl | — |
| 222 | CH₂=CH– | cyclohexyl | — | cyclohexyl | — |

|     |          |                 |   |                 |   |
|-----|----------|-----------------|---|-----------------|---|
| 223 | CH$_3$ |  | — | 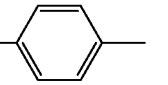 | — |
| 224 | C$_2$H$_5$ |  | — | 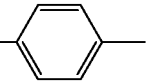 | — |
| 225 | n-C$_3$H$_7$ |  | — | 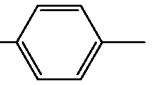 | — |
| 226 | n-C$_5$H$_{11}$ | 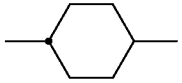 | — | 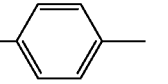 | — |
| 227 | n-C$_3$H$_7$ | 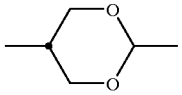 | — | 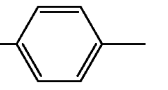 | — |
| 228 |  | 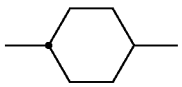 | — | 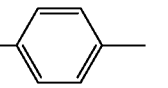 | — |
| 229 | CH$_3$ | 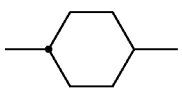 | — | 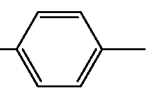 |  |
| 230 | C$_2$H$_5$ | 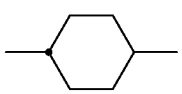 | — | 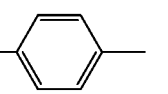 |  |
| 231 | n-C$_3$H$_7$ | 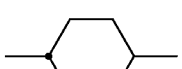 | — | 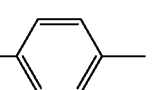 |  |
| 232 | n-C$_5$H$_{11}$ | 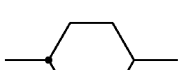 | — | 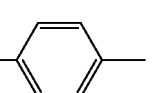 |  |
| 233 | n-C$_3$H$_7$ | 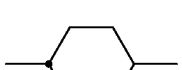 | — | 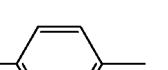 |  |
| 234 | n-C$_3$H$_7$ | 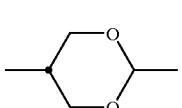 | — | 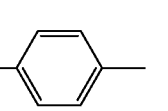 |  |
| 235 |  | 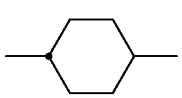 | — | 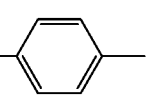 |  |
| 236 | CH$_3$ | 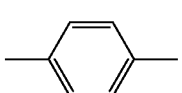 | — | 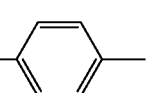 | — |

-continued
| No. | | $A_3$ | $B_3$ | $A_4$ | G |
|---|---|---|---|---|---|
| 237 | C₂H₅ | 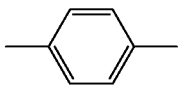 | — | 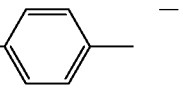 | — |
| 238 | n-C₃H₇ | 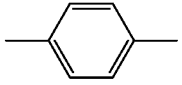 | — | 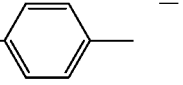 | — |
| 239 | n-C₃H₇ |  | — | 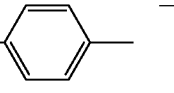 | — |
| 240 | n-C₅H₁₁ | 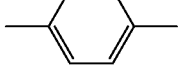 | — | 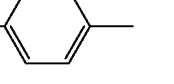 | — |
| 241 | C₂H₅O | 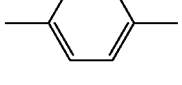 | — | 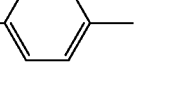 | — |
| 242 |  | 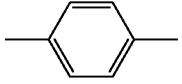 | — | 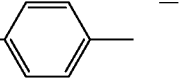 | — |
| 243 | NC | 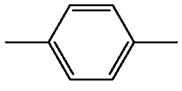 | — | 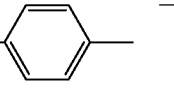 | — |
| 244 | F | 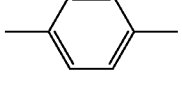 | — | 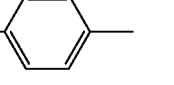 | — |
$m = n = p = 1$
| No. | $A_3$ | $B_3$ | $A_4$ | G |
|---|---|---|---|---|
| 179 |  | — | 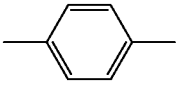 | 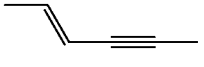 |
| 180 | 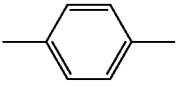 | — | 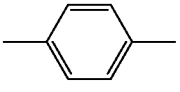 | 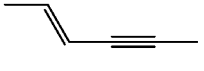 |
| 181 | 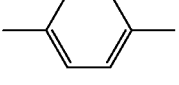 | — | 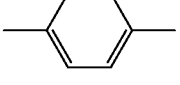 | 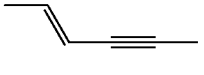 |
| 182 | 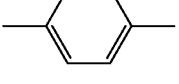 | — | 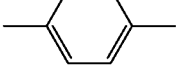 | 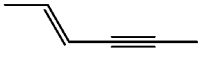 |
| 183 | 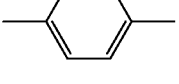 | — | 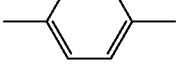 | 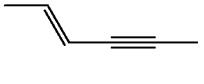 |

-continued
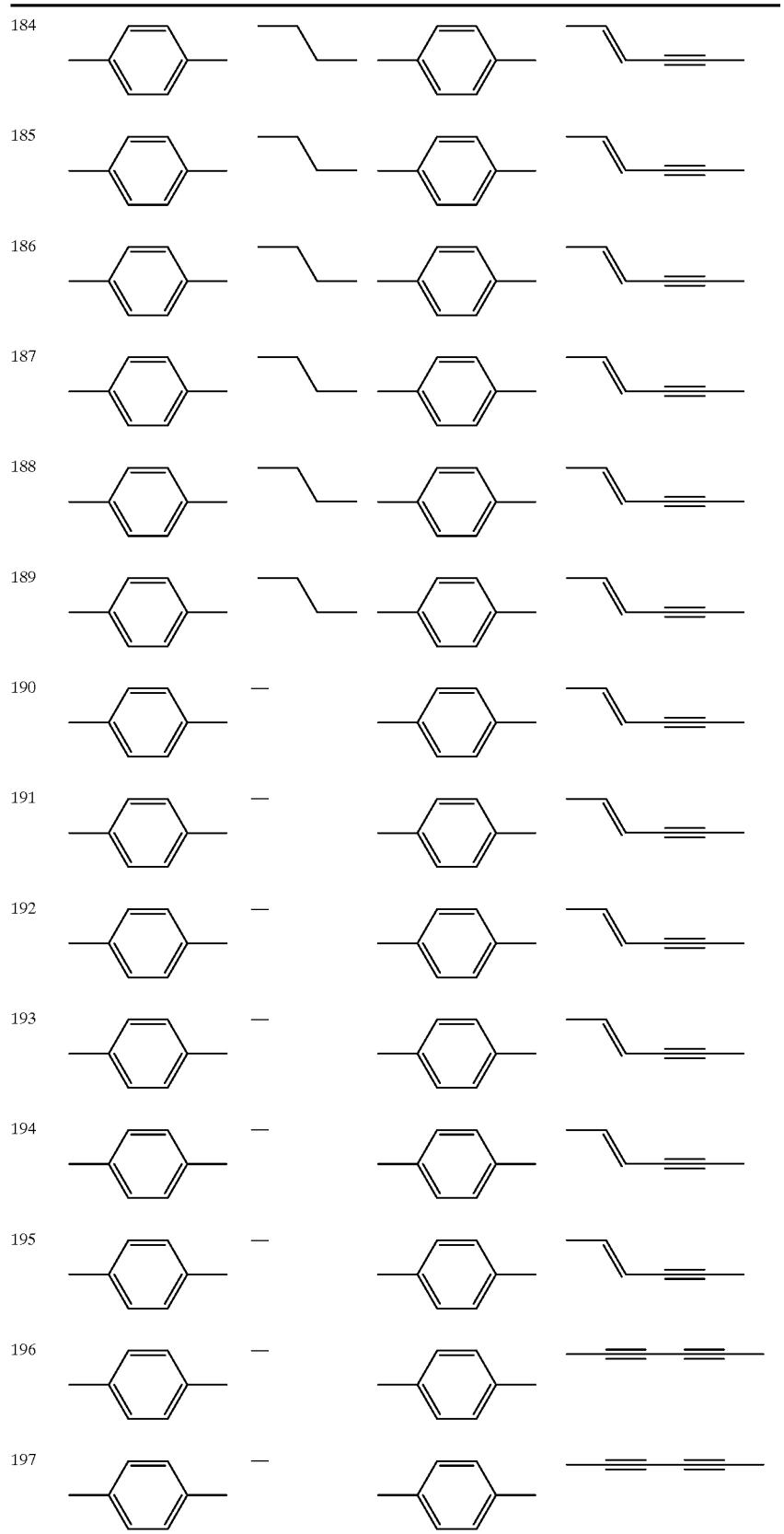

-continued
| | | | |
|---|---|---|---|
| 198 |  | — |  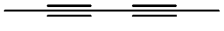 |
| 199 |  | — |  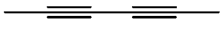 |
| 200 |  | — | 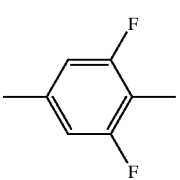 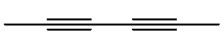 |
| 201 |  | — |  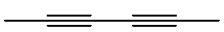 |
| 202 |  | — |  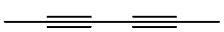 |
| 203 |  | — |  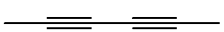 |
| 204 | 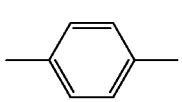 | — | 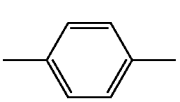 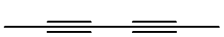 |
| 205 | 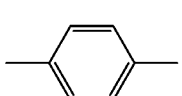 | — | 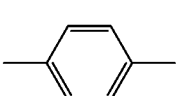  |
| 206 | 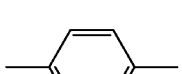 | — | 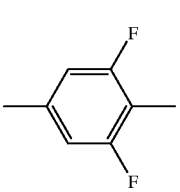  |
| 207 |  | — |  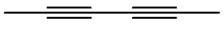 |
| 208 |  | — |  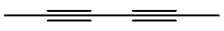 |
| 209 |  | — |  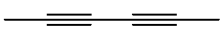 |
| 210 |  | — |  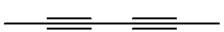 |

-continued
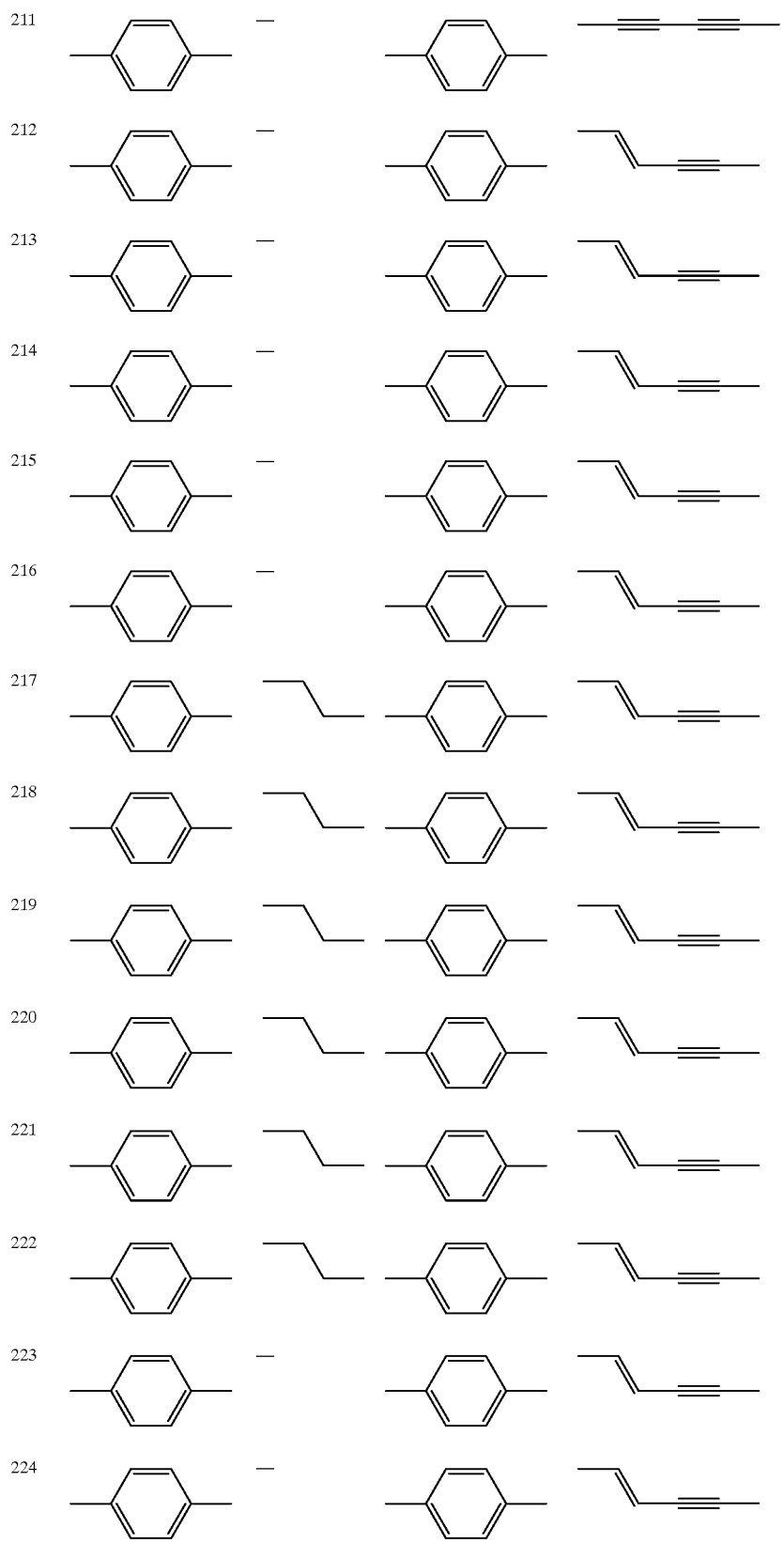

-continued
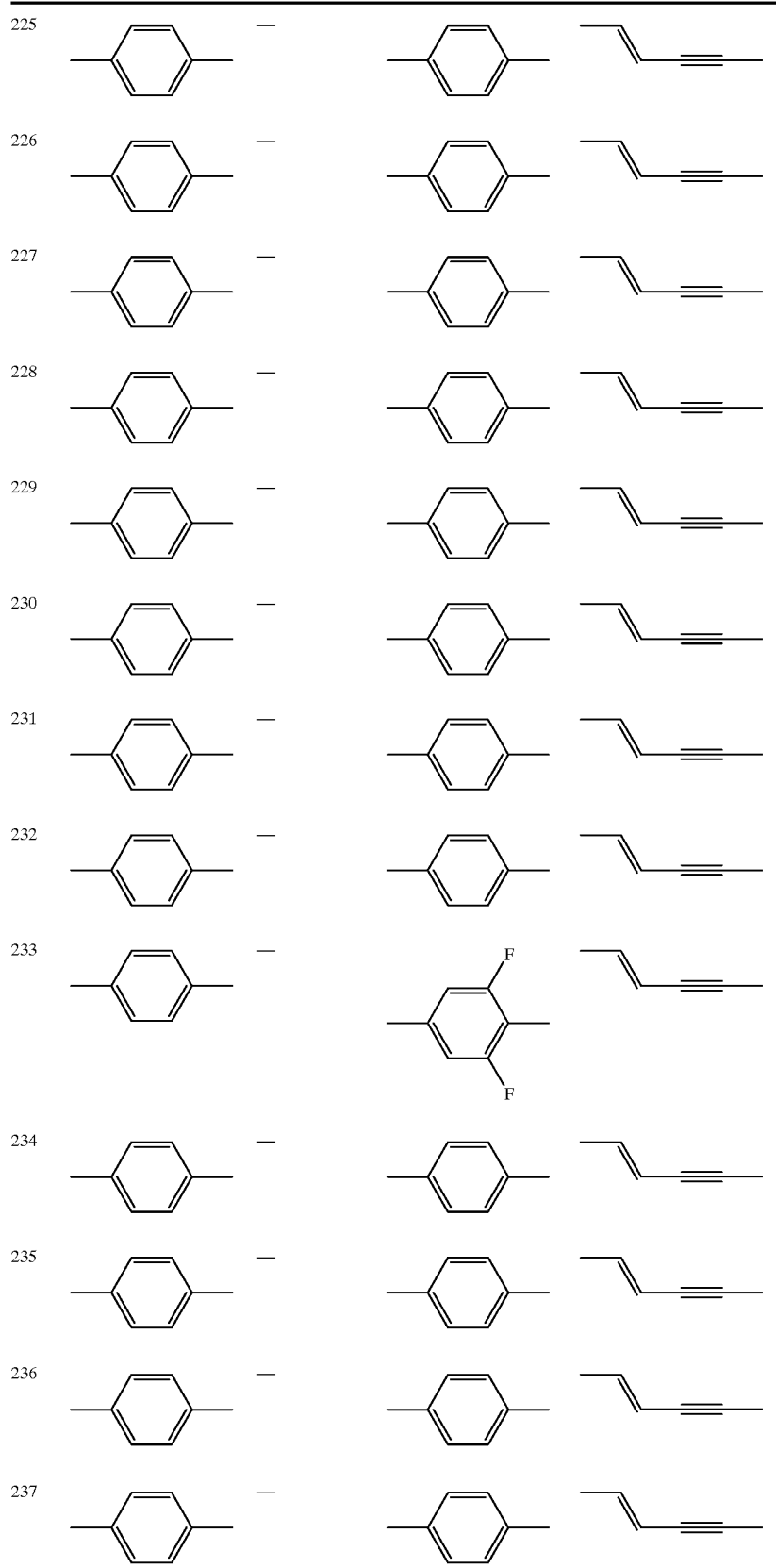

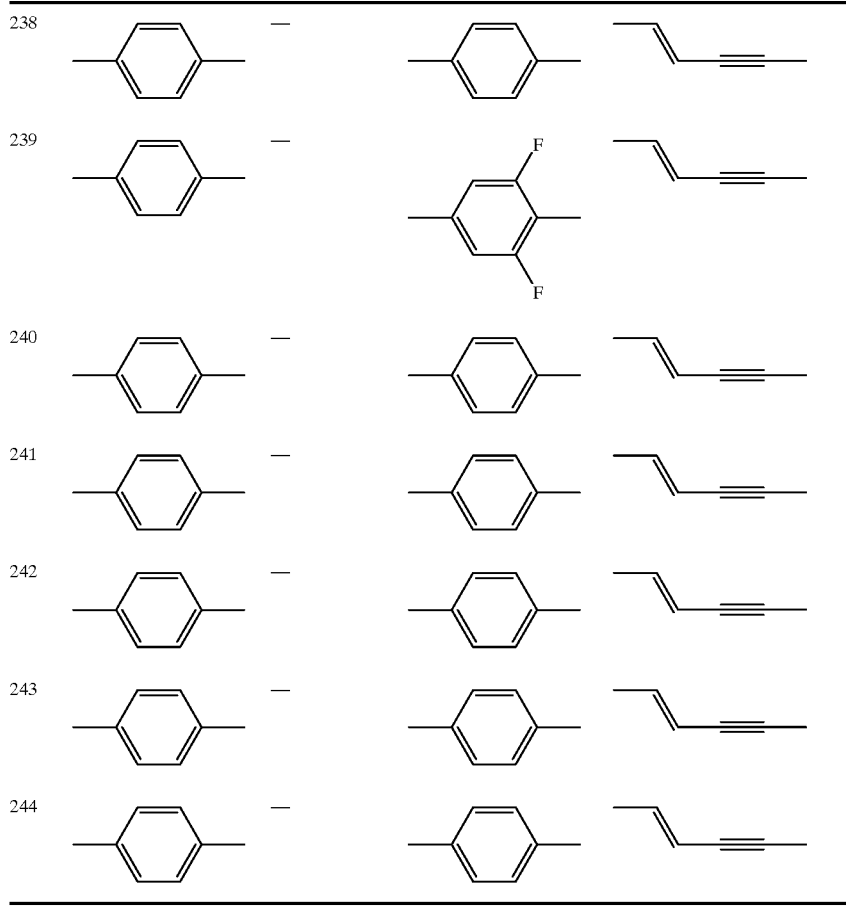

EXAMPLE 10

Preparation of 1-(4-cyano-1-butyne-3-ene-1-yl)-4-(2-(trans-4-propylcyclohexyl)ethylbenzene (Compound No. 250)

To dichlorobistriphenylphosphine palladium and copper iodide was added to suspend diethylamine, and then 1,2-dichloroethylene was added thereto while being stirred, and it was further stirred for 15 minutes. To the reaction liquid was added by drops a solution of 1-ethynyl-4-(2-(trans-4-propylcyclohexyl)ethylbenzene in diehtylamine, and further stirred at room temperature for 3 hours. After finishing of the reaction, water was added to the solution and extracted with toluene. The organic layer thus obtained was washed with water, dried over anhydrous magnesium sulfate, and then concentrated under a reduced pressure to obtain a brown oily product.

After this product was purified by using silica gel column chromatography, it was recrystallized from ethanol to obtain white crystals of 1-(4-chloro-1-butyne-3-ene-1-yl)-4-(2-(trans-4-propylcyclohexyl)ethylbenzene.

This product and copper cyanide were dissolved in N-methylpyrrolidone and then stirred under heated reflux condition for 3 hours. After the finishing of the reaction, a solution of iron (II) chloride in 6N hydrochloric acid was added to the solution and further stirred for 30 minutes. After this solution was filtrated through Celite (filter medium), and undissolved matters were separated, it was extracted with toluene. After the organic layer was washed with water, it was dried over anhydrous magnesium sulfate, and then concentrated under a reduced pressure to obtain a brown oily product. This product was purified and isolated by using silica gel column chromatography to obtain the subject compound.

C.43.6.N.147.3.I.

EXAMPLE 11

Preparation of 1-(4-cyano-1-butyne-3-ene-1-yl)-4-(trans-4-vinylcyclohexyl)benzene (Compound No. 252).

To dichlorobistriphenylphosphine palladium and copper iodide was added to suspend diethylamine, and then 1,2-dichloroethylene was added thereto while being stirred, and it was further stirred for 15 minutes.

To the reaction liquid was added by drops a solution of 1-ethynyl-4-(trans-4-vinylcyclohexyl)benzene in diehtylamine, and further stirred at room temperature for 3 hours. After finishing of the reaction, water was added to the solution and extracted with toluene. The organic layer thus obtained was washed with water, dried over anhydrous magnesium sulfate, and then concentrated under a reduced pressure to obtain a brown oily product. After this product was purified by using silica gel column chromatography, it was recrystallized from ethanol to obtain white crystals of 1-(4-chloro-1-butyne-3-ene-1-yl)-4(trans-4-vinylcyclohexyl)benzene.

This product and copper cyanide were dissolved in N-methylpyrrolidone and then stirred under heated reflux condition for 3 hours. After finishing of the reaction, a solution of iron (II) chloride in 6N hydrochloric acid was added thereto and further stirred for 30 minutes. After this solution was filtrated through Celite (filter medium), and undissolved matters were separated, it was extracted with toluene. After the organic layer was washed with water, it was dried over anhydrous magnesium sulfate, and then concentrated under a reduced pressure to obtain a brown oily product. This product was purified and isolated by using silica gel column chromatography to obtain the subject compound.

Based on the descriptions in Examples 10 and 11, the following compounds of No. 245 to No. 354 can be prepared.

In the following, compounds obtained in Examples 10 and 11 are described again.

| | | | | m = 1, n = p = 0 | | |
|---|---|---|---|---|---|---|
| No. | R | $A_1$ | $B_1$ | | $A_4$ | G |
| 245 | $CH_3$ |  | — | |  |  |
| 246 | $CH_3CH_2$ |  | — | |  |  |
| 247 | $n\text{-}C_3H_7$ |  | — | |  | 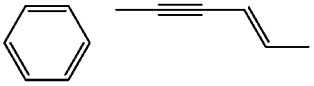 |
| 248 | $CH_3OCH_2$ |  | 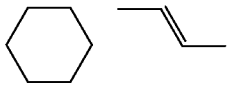 | |  |  |
| 249 | $n\text{-}C_3H_7$ |  | 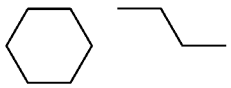 | |  | 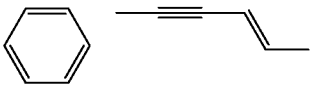 |
| 250 | $n\text{-}C_5H_{11}$ |  | 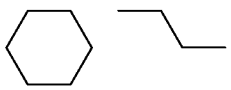 | |  |  |
| 251 | $n\text{-}C_7H_{15}$ |  | 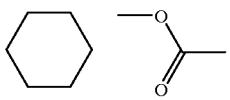 | |  |  |
| 252 | $CH_2=CH$ |  | — | |  |  |
| 253 | $CH_2=CH\text{—}(CH_2)_2$ |  | — | |  |  |
| 254 | $CH_2FCH_2CH=CH$ |  | — | | 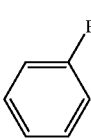 | 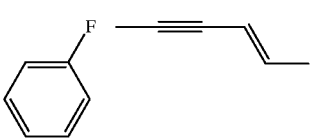 |
| 255 | $CH_3$ |  | — | |  | 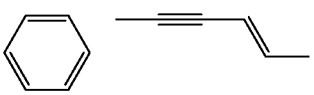 |

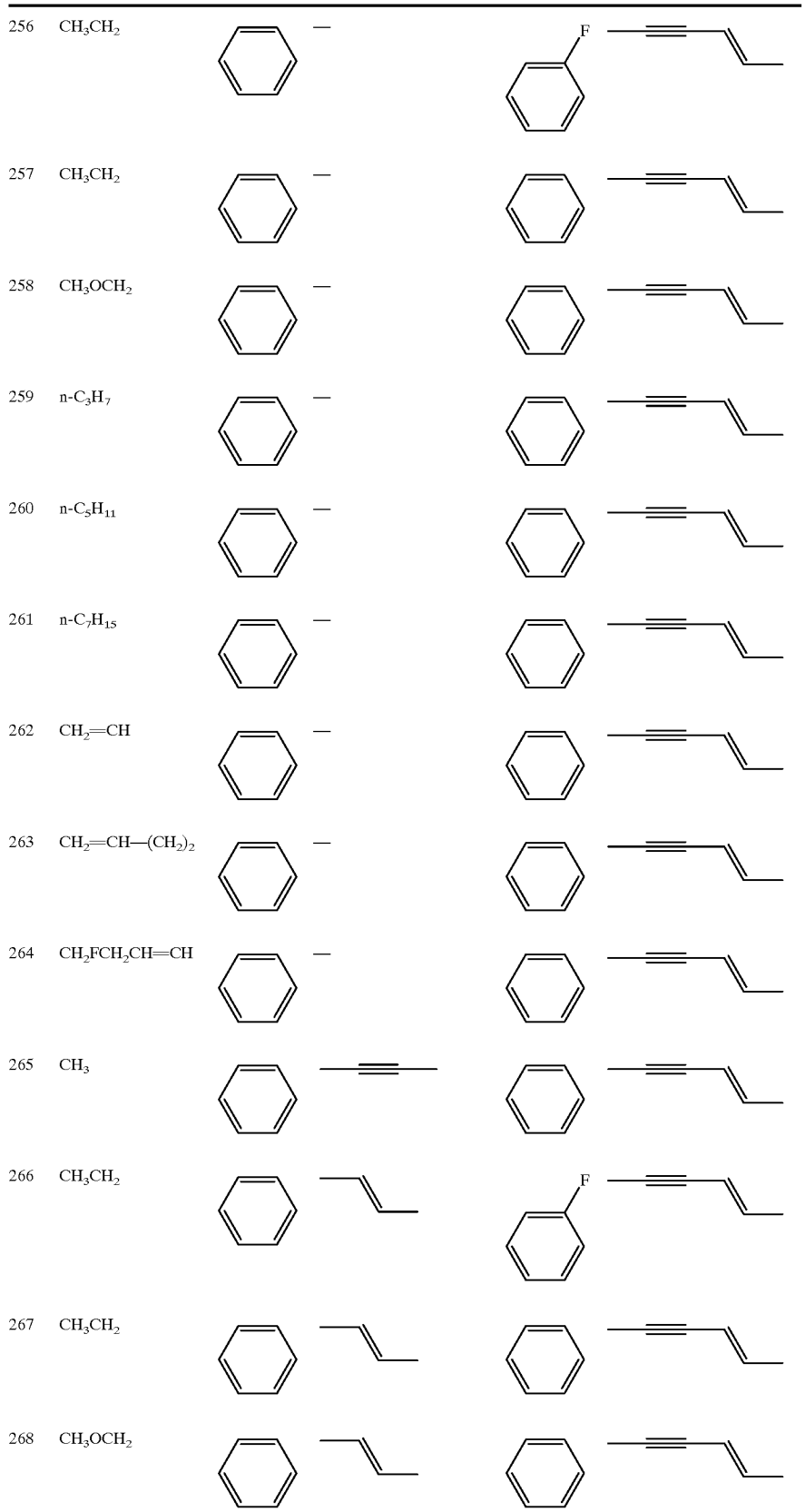

-continued
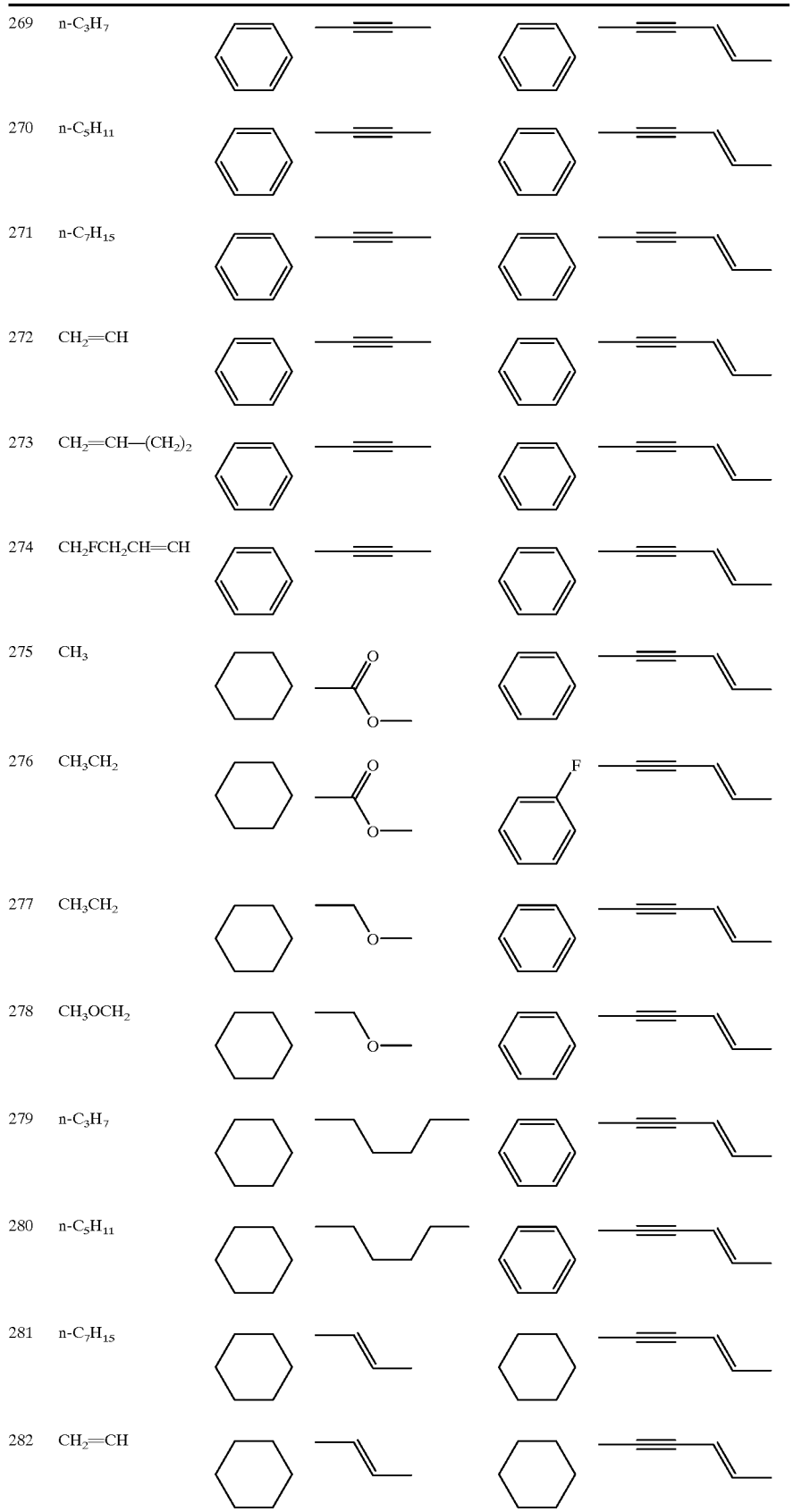

-continued
| No. | R | A1 | B₁ | A2 | |
|---|---|---|---|---|---|
| 283 | CH₂=CH—(CH₂)₂ | 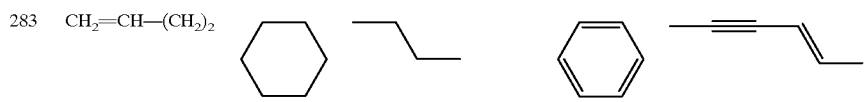 | | | |
| 284 | CH₂FCH₂CH=CH | 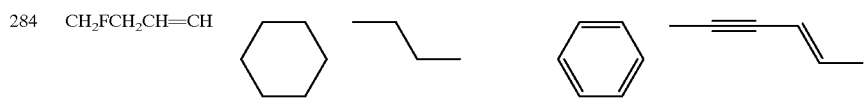 | | | |
m = n = 1, p = 0
| No. | R | A1 | B₁ | A2 |
|---|---|---|---|---|
| 285 | CH₃ | ⬡ | — | ⬡ |
| 286 | CH₃CH₂ | ⬡ | — | ⬡ |
| 287 | CH₃CH₂ | ⬡ | — | ⬡ |
| 288 | CH₃OCH₂ | ⬡ | — | ⬡ |
| 289 | n-C₃H₇ | ⬡ | — | ⬡ |
| 290 | n-C₅H₁₁ | ⬡ | — | ⬡ |
| 291 | n-C₇H₁₅ | ⬡ | — | ⬡ |
| 292 | CH₂=CH | ⬡ | — | ⬡ |
| 293 | CH₂=CH—(CH₂)₂ | ⬡ | — | ⬡ |
| 294 | CH₂FCH₂CH=CH | ⬡ | — | ⬡ |
| 295 | CH₃ | ⬡ | ⟋⟍ | ⬡ |

-continued
| | | | | |
|---|---|---|---|---|
| 296 | CH₃CH₂ |  |  |  |
| 297 | CH₃CH₂ |  | 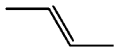 |  |
| 298 | CH₃OCH₂ |  | 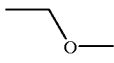 |  |
| 299 | n-C₃H₇ |  | 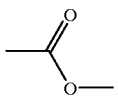 |  |
| 300 | n-C₅H₁₁ |  | 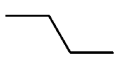 |  |
| 301 | n-C₇H₁₅ |  |  |  |
| 302 | CH₂=CH |  | 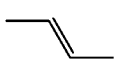 |  |
| 303 | CH₂=CH—(CH₂)₂ |  | 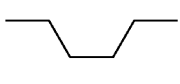 |  |
| 304 | CH₂FCH₂CH=CH |  | 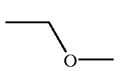 |  |
| 305 | CH₃ |  | — |  |
| 306 | CH₃CH₂ |  | — |  |
| 307 | CH₃CH₂ |  | — |  |
| 308 | CH₃OCH₂ |  | — |  |
| 309 | n-C₃H₇ |  | — |  |

-continued
| | | | | |
|---|---|---|---|---|
| 310 | n-C$_5$H$_{11}$ |  | — |  |
| 311 | n-C$_7$H$_{15}$ |  | — |  |
| 312 | CH$_2$=CH |  | — |  |
| 313 | CH$_2$=CH—(CH$_2$)$_2$ |  | — |  |
| 314 | CH$_2$FCH$_2$CH=CH |  | — |  |
| 315 | CH$_3$ |  | — |  |
| 316 | CH$_3$CH$_2$ |  | — |  |
| 317 | CH$_3$CH$_2$ |  | — |  |
| 318 | CH$_3$OCH$_2$ |  | — |  |
| 319 | n-C$_3$H$_7$ |  | — |  |
| 320 | n-C$_5$H$_{11}$ |  | — |  |
| 321 | n-C$_7$H$_{15}$ |  | — |  |
| 322 | CH$_2$=CH |  | — |  |
| 323 | CH$_2$=CH—(CH$_2$)$_2$ |  | — |  |

-continued
| No. | B₂ | A4 | | G |
|---|---|---|---|---|
| 324 | CH₂FCH₂CH=CH |  | 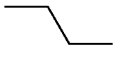 |  |
| 325 | CH₃ |  | — |  |
| 326 | CH₃CH₂ |  | — |  |
| 327 | CH₃CH₂ |  | — |  |
| 328 | CH₃OCH₂ |  | — |  |
| 329 | n-C₃H₇ |  | — |  |
| 330 | n-C₅H₁₁ |  | — |  |
| 331 | n-C₇H₁₅ |  | — |  |
| 332 | CH₂=CH |  | — |  |
| 333 | CH₂=CH—(CH₂)₂ |  | — |  |
| 334 | CH₂FCH₂CH=CH |  | — |  |
|  | | m = n = 1, p = 0 | |
|---|---|---|---|
| No. | B₂ | A4 | G |
| 285 | — |  | 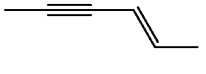 |
| 286 | — | 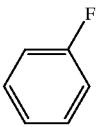 | 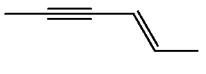 |

-continued
| | | | |
|---|---|---|---|
| 287 | — |  |  |
| 288 | — |  |  |
| 289 | — |  |  |
| 290 | — |  |  |
| 291 | — |  |  |
| 292 | — |  |  |
| 293 | — |  |  |
| 294 | — |  |  |
| 295 | — |  | 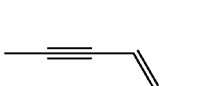 |
| 296 | — |  |  |
| 297 | — |  |  |
| 298 | — |  |  |
| 299 | — |  |  |
| 300 | — |  |  |

-continued
| | | | |
|---|---|---|---|
| 301 | — |  | 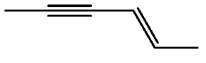 |
| 302 | — |  | 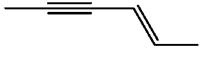 |
| 303 | — |  |  |
| 304 | — |  |  |
| 305 | — |  |  |
| 306 | — | 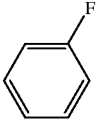 |  |
| 307 | — |  |  |
| 308 | — |  |  |
| 309 | — |  |  |
| 310 | — |  |  |
| 311 | — |  |  |
| 312 | — |  | 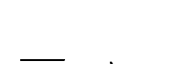 |
| 313 | — |  | 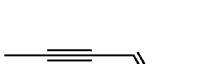 |
| 314 | — |  |  |

-continued
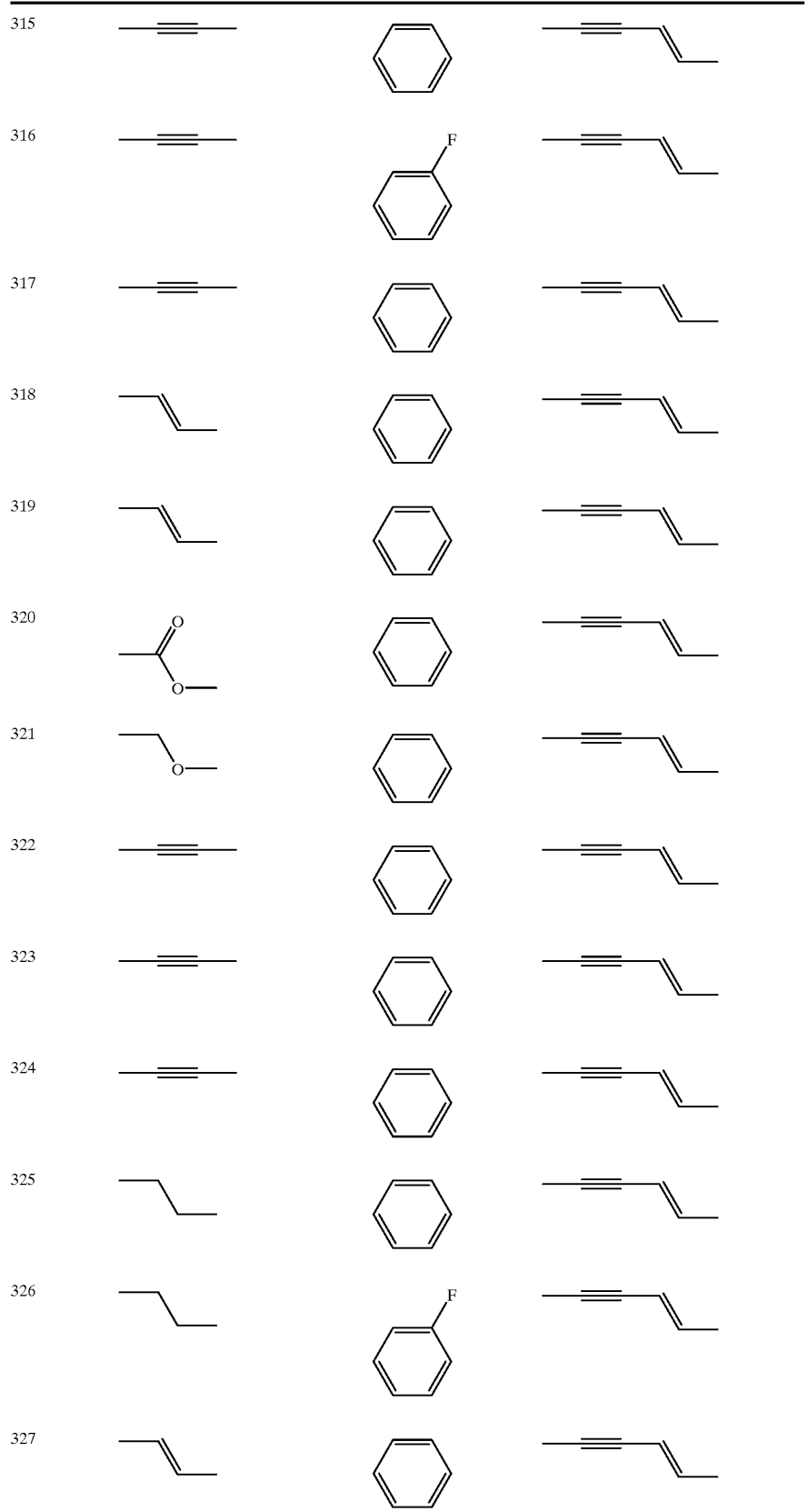

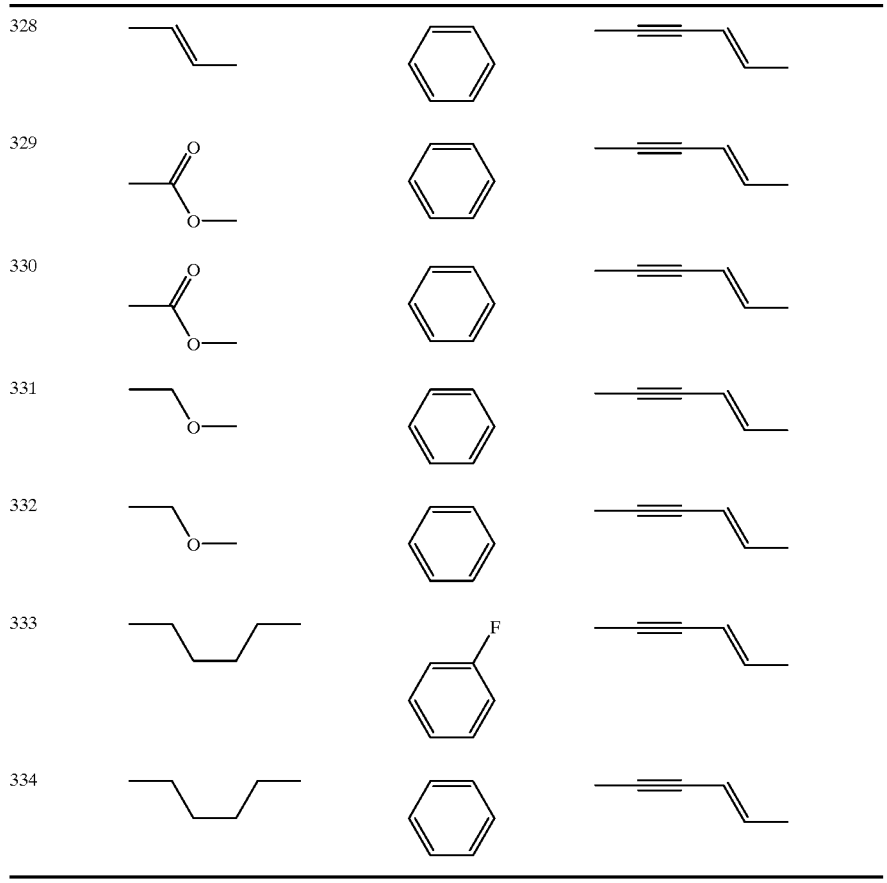

-continued
| | | | | |
|---|---|---|---|---|
| 341 | n-C$_7$H$_{15}$ |  | — |  |
| 342 | CH$_2$=CH |  | — |  |
| 343 | CH$_2$=CH—(CH$_2$)$_2$ |  | — |  |
| 344 | CH$_2$FCH$_2$CH=CH |  | — |  |
| 345 | CH$_3$ |  | — |  |
| 346 | CH$_3$CH$_2$ |  | — |  |
| 347 | CH$_3$CH$_2$ |  | — |  |
| 348 | CH$_3$OCH$_2$ |  | — |  |
| 349 | n-C$_3$H$_7$ |  |  |  |
| 350 | n-C$_5$H$_{11}$ |  |  |  |
| 351 | n-C$_7$H$_{15}$ |  |  |  |
| 352 | CH$_2$=CH |  |  |  |
| 353 | CH$_2$=CH—(CH$_2$)$_2$ |  |  |  |
| 354 | CH$_2$FCH$_2$CH=CH |  |  |  |

-continued

| | | m = n = p = 1 | | | |
|---|---|---|---|---|---|
| No. | $B_2$ | $A_3$ | $B_3$ | $A_4$ | G |
| 335 | propyl | cyclohexyl | — | phenyl | ─≡─CH=CH─ |
| 336 | propyl | cyclohexyl | — | fluorophenyl | ─≡─CH=CH─ |
| 337 | propenyl | cyclohexyl | — | phenyl | ─≡─CH=CH─ |
| 338 | propenyl | phenyl | — | phenyl | ─≡─CH=CH─ |
| 339 | ester | phenyl | — | phenyl | ─≡─CH=CH─ |
| 340 | ester | cyclohexyl | — | phenyl | ─≡─CH=CH─ |
| 341 | ether | phenyl | — | phenyl | ─≡─CH=CH─ |
| 342 | ether | cyclohexyl | — | phenyl | ─≡─CH=CH─ |
| 343 | pentyl | cyclohexyl | — | fluorophenyl | ─≡─CH=CH─ |
| 344 | pentyl | cyclohexyl | — | phenyl | ─≡─CH=CH─ |
| 345 | — | cyclohexyl | — | phenyl | ─≡─CH=CH─ |
| 346 | — | cyclohexyl | — | fluorophenyl | ─≡─CH=CH─ |

-continued

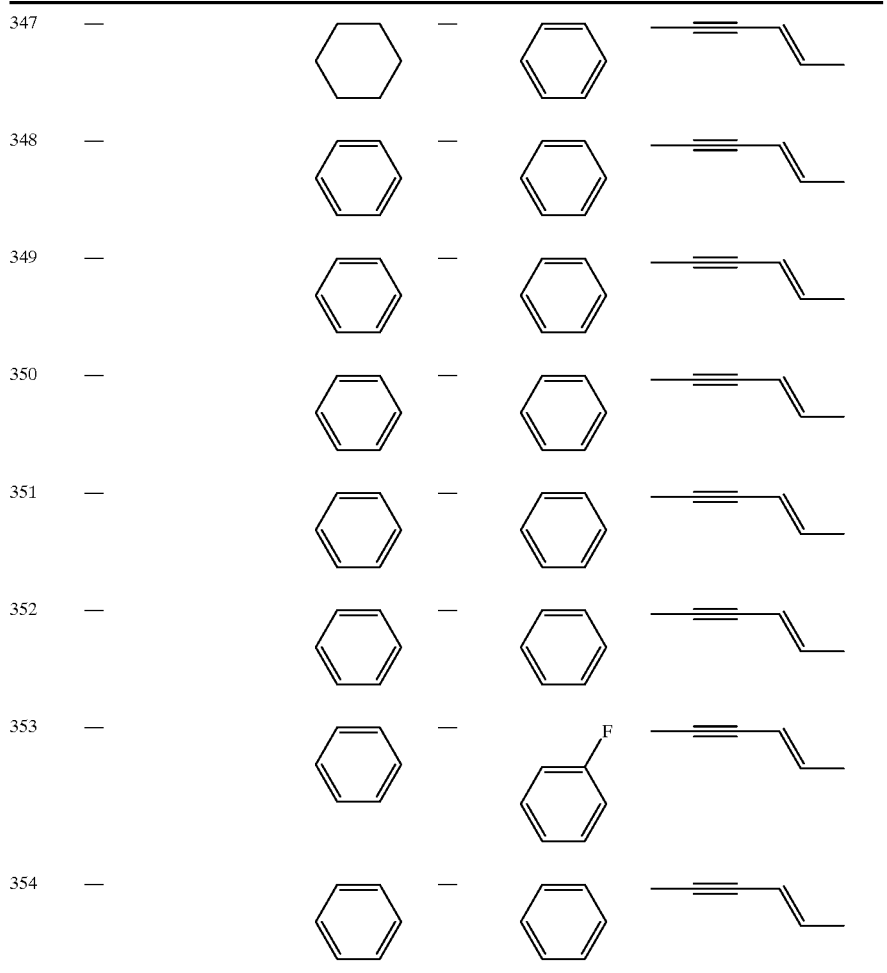

EXAMPLE 12

Use Example 1

A nematic liquid crystal composition (hereinafter sometimes referred to as liquid crystal composition A1):

4-(trans-4-propylcyclohexyl)benzonitrile 24% by weight
4-(trans-4-pentylcyclohexyl)benzonitrile 36% by weight
4-(trans-4-heptylcyclohexyl)benzonitrile 25% by weight
4-(trans-4-propylphenyl)benzonitrile 15% by weight had the following characteristics.

Clearing point (Cp): 71.7° C., threshold voltage at a cell thickness of 9 μm ($V_{th}$) 1.78 V, Δε: 11.0, Δn: 0.137, viscosity at 20° C. ($\eta_{20}$): 27.0 mPa·s To this liquid crystal composition A1 in an amount of 85% by weight was mixed 15% by weight of the trans-4-(trans-4-pentylcyclohexyl)-1-(4-cyano-1-E-butene-3-yne-1-yl)cyclohexane (Compound No. 34) obtained in Example 1 to prepare liquid crystal composition B1, and its physical properties were determined to be as follows:

Clearing point (Cp): 90.0° C., threshold voltage at a cell thickness of 9 μm ($V_{th}$): 1.73 V, Δε: 11.2, Δn: 0.145, viscosity at 20° C. ($\eta_{20}$): 27.4 mPa·s While this composition was left in a freezer at −20° C. for 30 days, either separation of crystals and development of smectic phase were not observed.

EXAMPLE 13

Use Example 2

Liquid crystal composition B2 was prepared in the same manner as in Example 12 with the exception that the 4-(trans-4-propylcyclohexyl)-1-(4-cyano-1,3-butadiyne-1-yl)benzene (Compound No. 62) obtained in Example 2 was used instead of the compound of No. 34, and its physical properties were determined to be as follows:

Clearing point (Cp): 88.4° C., threshold voltage at a cell thickness of 9 μm ($V_{th}$): 1.60 V, Δε: 12.1, Δn: 0.177, viscosity at 20° C. ($\eta_{20}$): 25.6 mPa·s While this composition was left in a freezer at −20° C. for 30 days, either separation of crystals and development of smectic phase were not observed.

EXAMPLE 14

Use Example 3

Liquid crystal composition B3 was prepared in the same manner as in Example 12 with the exception that the compound of No. 246 was used instead of the compound of No. 34.

While this composition was left in a freezer at −20° C. for 30 days, either separation of crystals and development of smectic phase were not observed.

Comparative Example 1

As comparative compound to those of the present invention, compound (a) which is expressed by the formula (13) described above wherein R is pentyl group was actually synthesized, and its physical properties were determined in the same manner as in the Examples described above. The results were as shown in Table 2 below.

In the Table 2, physical properties of known compounds which are expressed by the formula (b), (c), or (d) which is the same as the formula (a) described above except that CN group at right side terminal is replaced by Cl, $CHF_2$, or $CF_3$, as other comparative compounds; and physical properties of the compound of No. 34 used in Example 12, compound of No. 62 used in Example 13, and compound of No. 246 used in Example 14 as examples of the compounds of the present invention are shown together.

Among the physical properties, $\Delta\epsilon$, $\Delta n$, and $\eta_{20}$ indicate extrapolated values, and physical properties of known compounds expressed by the formulas (a) to (d) are transcribed from those described in the literature.

the formula (a) to (d)) in the temperature range in which the compounds exhibit nematic phase;

about the same (comparison between the compound of No. 34 and the compound expressed by the formula (a)), or considerably large (comparison between the compound of No. 62 and the compound expressed by one of the formulas (a) to (d)) in $\Delta n$; and larger than the compound expressed by the formula (a) which has the largest value among the comparative compounds in $\Delta\epsilon$.

Further, as to viscosity ($\eta_{20}$), whereas the compounds of the present invention exhibit a higher value than that of the comparative compounds, when the viscosity is such an extent, viscosity of liquid crystal compositions is not so increased even when the compounds of the present invention are used as their component, and thus it does not become specific problems in actual uses.

As described above, since the compounds of the present invention exhibit a large $\Delta n$, it is possible to make the thickness of liquid crystal cells small by using the compound as component of liquid crystal compositions. Also, liquid

TABLE 2

| Compound | | Phase transition temperature | $\Delta\epsilon$ | $\Delta n$ | $\eta 20$ (mPa.s) |
|---|---|---|---|---|---|
| No. 34 | $C_5H_{11}$—◯—◯—CH=CH—C≡C—CN | C.42.8.N.212(dec. >170).I | 12.3 | 0.190 | 31.9 |
| No. 62 | $C_3H_7$—◯—◯—C≡C—C≡C—CN | C.71.3.N.dec. >150 | 24.0 | 0.404 | 17.7 |
| No. 246 | $C_2H_5$—◯—◯—C≡C—CH=CH—CN | C.57.1.N.155.7.I | 16.3 | 0.304 | 55.3 |
| (a) | $C_5H_{11}$—◯—◯—C≡C—CN | C.49.7.N.128.9.I | 19.0 | 0.224 | 13.9 |
| (b) | $C_5H_{11}$—◯—◯—C≡C—Cl | C.66.N.70.I | — | — | — |
| (c) | $C_5H_{11}$—◯—◯—C≡C—$CHF_2$ | C.37(.N.34).I | 7.8 | 0.148 | — |
| (d) | $C_5H_{11}$—◯—◯—C≡C—$CF_3$ | C.108.I | — | 0.169 | — |

From the results shown in Table 2, it can be understood that the compounds of No. 34, No. 62, and No. 246 which are examples of the compounds of the present invention are equal compared with comparative compounds expressed by one of the formulas (a) to (d) (comparison between the compound of No. 62 and the compound expressed by the formula (a)), or considerably wide (comparison between the compound of No. 34 and the compound expressed by one of crystal compositions having an increased response speed against the change in electric field and increased steepness can be obtained by using the present compounds as component since the compounds of the present invention exhibit a large $\Delta\epsilon$. Further, when the compounds of the present invention are used as component of liquid crystal compositions, the compositions exhibit an excellent miscibility at low temperatures. Besides, the present compounds are chemically and physically stable since they are not decomposed or react with other components.

As described above, liquid crystalline compounds of the present invention have a sufficiently large Δn and a large Δε, are excellent in miscibility with other liquid crystalline compounds, are low in viscosity, and are chemically and physically stable novel liquid crystalline compounds.

INDUSTRIAL APPLICABILITY

Accordingly, liquid crystal compositions which are improved particularly in response speed against the change in electric field and steepness, and liquid crystal display devices fabricated by using the liquid crystal composition can be provided by using the liquid crystalline compounds of the present invention as component of liquid crystal compositions.

What is claimed is:

1. A conjugated nitrile derivative expressed by the general formula (1)

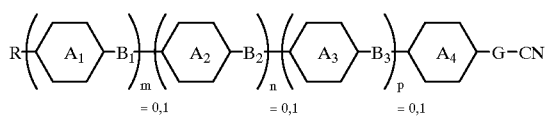

wherein rings $A_1$, $A_2$, $A_3$, and $A_4$ independently represent 1,4-cyclohexylene, 1,4-phenylene in which one or two hydrogen atoms on the ring may be replaced by fluorine atom, 1,3-dioxane-2,5-diyl, or pyrimidine-2,5-diyl; $B_1$, $B_2$, and $B_3$ independently represent a covalent bond, 1,2-ethylene, 1,2-ethenylene, 1,2-ethynylene, oxymethylene, methylenoxy, carbonyloxy, or 1,4-butylene group; G represents the formula (2), (3), or (4)

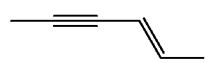

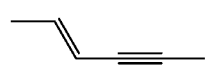

R represents an alkyl group having 1 to 10 carbon atoms, a fluoroalkyl group having 1 to 10 carbon atoms, a halogen atom, or cyano group provided that in the alkyl group or fluoroalkyl group, one or not-adjacent two or more methylene groups or fluoromethylene groups may be replaced by oxygen atom or 1,2-ethenylene group; and m, n, and p are independently 0 or 1.

2. The conjugated nitrile derivative according to claim 1 wherein m=n=p=0.

3. The conjugated nitrile derivative according to claim 1 wherein m=n=0, and p=1.

4. The conjugated nitrile derivative according to claim 1 wherein m=0, and n=p=1.

5. The conjugated nitrile derivative according to claim 1 wherein m=n=p=1.

6. The conjugated nitrile derivative according to claim 3 wherein G is the group expressed by the formula (2).

7. The conjugated nitrile derivative according to claim 6 wherein $A_4$ is 1,4-cyclohexylene.

8. The conjugated nitrile derivative according to claim 6 wherein $A_4$ is 1,4-phenylene ring in which one or two hydrogen atoms on the ring may be replaced by fluorine atom.

9. The conjugated nitrile derivative according to claim 7 wherein $A_3$ is 1,4-cyclohexylene, and $B_3$ is a covalent bond.

10. The conjugated nitrile derivative according to claim 3 wherein G is the group expressed by the formula (3).

11. The conjugated nitrile derivative according to claim 10 wherein $A_4$ is 1,4-cyclohexylene.

12. The conjugated nitrile derivative according to claim 10 wherein $A_4$ is 1,4-phenylene ring in which one or two hydrogen atoms on the ring may be replaced by fluorine atom.

13. The conjugated nitrile derivative according to claim 11 wherein $A_3$ is 1,4-cyclohexylene, and $B_3$ is a covalent bond.

14. The conjugated nitrile derivative according to claim 12 wherein $A_3$ is 1,4-cyclohexylene, and $B_3$ is a covalent bond.

15. The conjugated nitrile derivative according to claim 3 wherein G is the group expressed by the formula (4).

16. The conjugated nitrile derivative according to claim 15 wherein $A_4$ is 1,4-cyclohexylene.

17. The conjugated nitrile derivative according to claim 15 wherein $A_4$ is 1,4-phenylene ring in which one or two hydrogen atoms on the ring may be replaced by fluorine atom.

18. The conjugated nitrile derivative according to claim 16 wherein $A_3$ is 1,4-cyclohexylene, and $B_3$ is a covalent bond.

19. The conjugated nitrile derivative according to claim 17 wherein $A_3$ is 1,4-cyclohexylene, and $B_3$ is a covalent bond.

20. The conjugated nitrile derivative according to claim 4 wherein G is the group expressed by the formula (2).

21. The conjugated nitrile derivative according to claim 20 wherein $A_4$ is 1,4-cyclohexylene.

22. The conjugated nitrile derivative according to claim 20 wherein $A_4$ is 1,4-phenylene ring in which one or two hydrogen atoms on the ring may be replaced by fluorine atom.

23. The conjugated nitrile derivative according to claim 4 wherein G is the group expressed by the formula (3).

24. The conjugated nitrile derivative according to claim 23 wherein $A_4$ is 1,4-cyclohexylene.

25. The conjugated nitrile derivative according to claim 23 wherein $A_4$ is 1,4-phenylene ring in which one or two hydrogen atoms on the ring may be replaced by fluorine atom.

26. The conjugated nitrile derivative according to claim 4 wherein G is the group expressed by the formula (4).

27. The conjugated nitrile derivative according to claim 26 wherein $A_4$ is 1,4-cyclohexylene.

28. The conjugated nitrile derivative according to claim 26 wherein $A_4$ is 1,4-phenylene ring in which one or two hydrogen atoms on the ring may be replaced by fluorine atom.

29. The conjugated nitrile derivative according to claim 5 wherein G is the group expressed by the formula (2).

30. The conjugated nitrile derivative according to claim 29 wherein $A_4$ is 1,4-cyclohexylene.

31. The conjugated nitrile derivative according to claim 29 wherein $A_4$ is 1,4-phenylene ring in which one or two hydrogen atoms on the ring may be replaced by fluorine atom.

32. The conjugated nitrile derivative according to claim 5 wherein G is the group expressed by the formula (3).

33. The conjugated nitrile derivative according to claim 32 wherein $A_4$ is 1,4-cyclohexylene.

34. The conjugated nitrile derivative according to claim 32 wherein $A_4$ is 1,4-phenylene ring in which one or two hydrogen atoms on the ring may be replaced by fluorine atom.

35. The conjugated nitrile derivative according to claim 5 wherein G is the group expressed by the formula (4).

36. The conjugated nitrile derivative according to claim 35 wherein $A_4$ is 1,4-cyclohexylene.

37. The conjugated nitrile derivative according to claim 35 wherein $A_4$ is 1,4-phenylene ring in which one or two hydrogen atoms on the ring may be replaced by fluorine atom.

38. A liquid crystal composition comprising at least one conjugated nitrile derivative defined in any one of claims 1 through 37.

39. A liquid crystal composition, comprising, as a first component, at least one conjugated nitrile derivative defined in any one of claims 1 through 37, and comprising, as a second component, at least one compound selected from the group consisting of the compounds expressed by any one of the general formulas (5), (6), and (7)

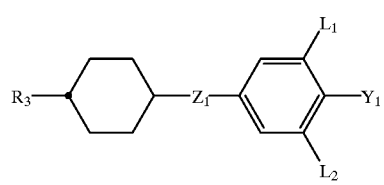
(5)

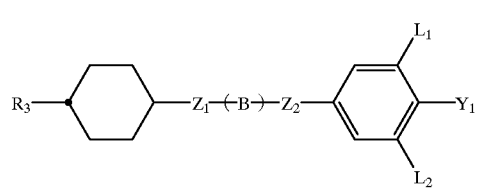
(6)

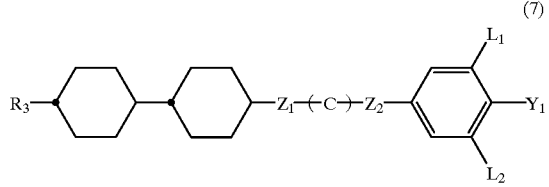
(7)

wherein $R_3$, $Y_1$, $L_1$, $L_2$, $Z_1$, and $Z_2$ may be the same or different from one another among the formulas; $R_3$ represents an alkyl group having 1 to 10 carbon atoms in which alkyl group, one or not-adjacent two or more methylene groups may be replaced by oxygen atom or —CH=CH—, and any hydrogen atom may be replaced by fluorine atom; $Y_1$ represents fluorine atom, chlorine atom, $OCF_3$, $OCF_2H$, $CF_3$, $CF_2H$, $CFH_2$, $OCF_2CF_2H$, or $OCF_2CFHCF_3$; $L_1$ and $L_2$ independently represent hydrogen atom or fluorine atom; $Z_1$ and $Z_2$ independently represent 1,2-ethylene group, 1,4-butylene group, —COO—, —$CF_2$—, —$OCF_2$—, —CH=CH—, or a covalent bond; B represents trans-1,4-cyclohexylene, or 1,3-dioxane-2,5-diyl, or 1,4-phenylene in which hydrogen atom on the ring may be replaced by fluorine atom; and C represents trans-1,4-cyclohexylene, or 1,4-phenylene in which hydrogen atom on the ring may be replaced by fluorine atom.

40. A liquid crystal composition, comprising, as a first component, at least one conjugated nitrile derivative defined in any one of claims 1 through 37, and comprising, as a second component, at least one compound selected from the group consisting of the compounds expressed by the general formula (8) or (9)

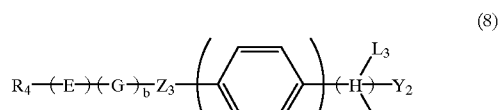
(8)

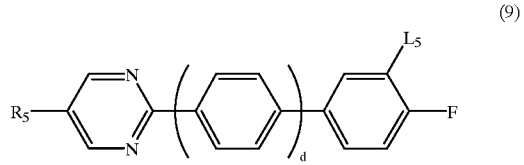
(9)

wherein $R_4$ and $R_5$ independently represent an alkyl group having 1 to 10 carbon atoms in which alkyl group, one or not-adjacent two or more methylene groups may be replaced by oxygen atom or —CH=CH—, and any hydrogen atom may be replaced by fluorine atom; $Y_2$ represents —CN group or —C≡C—CN; E represents trans-1,4-cyclohexylene, 1,4-phenylene, 1,3-dioxane-2,5-diyl, or pyrimidine-2,5-diyl; G represents trans-1,4-cyclohexylene, 1,4-phenylene in which hydrogen atom on the ring may be replaced by fluorine atom, or pyrimidine-2,5-diyl; H represents trans-1,4-cyclohexylene or 1,4-phenylene; $Z_3$ represents 1,2-ethylene group, —COO—, or a covalent bond; $L_3$, $L_4$, and $L_5$ independently represent hydrogen atom and or fluorine atom; b, c, and d are independently 0 or 1.

41. A liquid crystal composition, comprising, as a first component, at least one conjugated nitrile derivative defined in any one of claims 1 through 37, comprising, as a second component, at least one compound selected from the group consisting of the compounds expressed by any one of the general formulas (5), (6), and (7)

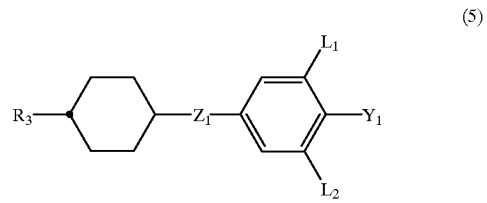
(5)

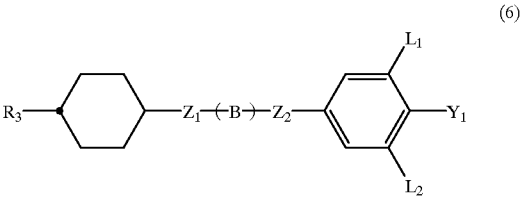
(6)

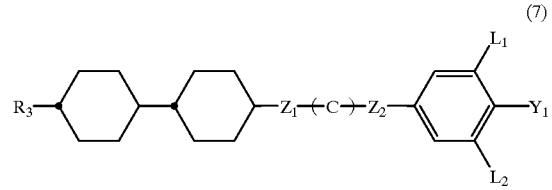
(7)

wherein $R_3$, $Y_1$, $L_1$, $L_2$, $Z_1$, and $Z_2$ may be the same or different from one another among the formulas; $R_3$ represents an alkyl group having 1 to 10 carbon atoms in which alkyl group, one or not-adjacent two or more methylene groups may be replaced by oxygen atom or —CH=CH—, and any hydrogen atom may be replaced by fluorine atom; $Y_1$ represents fluorine atom, chlorine atom, $OCF_3$, $OCF_2H$, $CF_3$, $CF_2H$, $CFH_2$, $OCF_2CF_2H$, or $OCF_2CFHCF_3$; $L_1$ and $L_2$ independently represent hydrogen atom or fluorine atom; $Z_1$ and $Z_2$ independently represent 1,2-ethylene group, 1,4-butylene group, —COO—, —CF$_2$O—, —OCF$_2$—, —CH=CH—, or a covalent bond; B represents trans-1,4-cyclohexylene or 1,3-dioxane-2,5-diyl, or 1,4-phenylene in which hydrogen atom on the ring may be replaced by fluorine atom; and C represents trans-1,4-cyclohexylene, or 1,4-phenylene in which hydrogen atom on the ring may be replaced by fluorine atom, and comprising, as a third component, at least one compound selected from the group consisting of the compounds expressed by any one of the general formulas (10), (11), and (12)

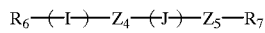 (10)

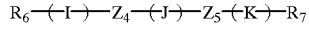 (11)

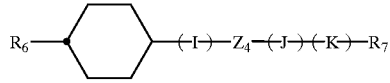 (12)

wherein $R_6$, $R_7$, I, J, and K may be the same or different from one another among the formulas; $R_6$ and $R_7$ independently represent an alkyl group having 1 to 10 carbon atoms in which alkyl group, one or not-adjacent two or more methylene groups may be replaced by oxygen atom or —CH=CH—, and any hydrogen atom may be replaced by fluorine atom; I, J, and K independently represent trans-1,4-cyclohexylene or pyrimidine-2,5-diyl, or 1,4-phenylene in which hydrogen atom and on the ring may be replaced by fluorine atom; $Z_4$ and $Z_5$ independently represent —C≡C—, —COO—, —CH$_2$CH$_2$—, —CH=CH—, or a covalent bond.

42. A liquid crystal composition, comprising, as a first component, at least one conjugated nitrile derivative defined in any one of claims 1 through 37, comprising, as a second component, at least one compound selected from the group consisting of the compounds expressed by the general formula (8) or (9) recited in claim 40, and comprising, as a third component, at least one compound selected from the group consisting of the compounds expressed by any one of the general formulas (10), (11), and (12) recited in claim 41.

43. A liquid crystal composition, comprising, as a first component, at least one conjugated nitrile derivative defined in any one of claims 1 through 37, comprising, as a part of a second component, at least one compound selected from the group consisting of the compounds expressed by any one of the general formulas (5), (6), and (7) recited in claim 39, comprising, as another part of the second component, at least one compound selected from the group consisting of the compounds expressed by the general formula (8) or (9) recited in claim 40, and comprising, as a third component, at least one compound selected from the group consisting of the compounds expressed by any one of the general formulas (10), (11), and (12) recited in claim 41.

44. A liquid crystal composition comprising the conjugated nitrile derivative defined in claim 1 and an optically active compound.

45. A liquid crystal display device comprising the liquid crystal composition defined in claim 44.

* * * * *